(12) United States Patent
Jain et al.

(10) Patent No.: US 11,328,796 B1
(45) Date of Patent: May 10, 2022

(54) TECHNIQUES FOR SELECTING COHORTS FOR DECENTRALIZED CLINICAL TRIALS FOR PHARMACEUTICAL RESEARCH

(71) Applicant: Vignet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 16/800,933

(22) Filed: Feb. 25, 2020

(51) Int. Cl.
| | | |
|---|---|---|
| *G16H 10/20* | (2018.01) | |
| *G16H 10/60* | (2018.01) | |
| *G06K 9/62* | (2022.01) | |
| *G06F 9/54* | (2006.01) | |
| *G06N 20/00* | (2019.01) | |

(52) U.S. Cl.
CPC .............. *G16H 10/20* (2018.01); *G06F 9/54* (2013.01); *G06K 9/6267* (2013.01); *G06N 20/00* (2019.01); *G16H 10/60* (2018.01)

(58) Field of Classification Search
CPC ........ G16H 10/20; G16H 10/60; G06N 20/00; G06F 9/54; G06K 9/6267
USPC .......................................................... 705/2–4
See application file for complete search history.

(56) References Cited

U.S. PATENT DOCUMENTS

| | | |
|---|---|---|
| 5,547,878 A | 8/1996 | Kell |
| 5,832,474 A | 11/1998 | Lopresti et al. |
| 6,029,144 A | 2/2000 | Barrett et al. |
| 6,514,200 B1 | 2/2003 | Khouri |
| 6,574,622 B1 | 6/2003 | Miyauchi et al. |
| 6,663,846 B1 | 12/2003 | McCombs et al. |
| 6,879,970 B2 | 4/2005 | Shiffman et al. |
| 7,054,782 B2 | 5/2006 | Hartlaub |
| 7,113,917 B2 | 9/2006 | Jacobi et al. |

(Continued)

FOREIGN PATENT DOCUMENTS

| | | |
|---|---|---|
| WO | WO 1995012812 | 5/1995 |
| WO | WO2013144769 | 10/2013 |
| WO | WO 2016110804 | 7/2016 |

OTHER PUBLICATIONS

Cancer.gov [online], "NCI Dictionary of Cancer Terms," Jan. 9, 2020, retrieved on Mar. 13, 2020, retrieved from URL<https://www.cancer.gov/publications/dictionaries/cancer-terms/def/research-study>, 1 page.

(Continued)

*Primary Examiner* — Mark Holcomb
(74) *Attorney, Agent, or Firm* — Fish & Richardson P.C.

(57) ABSTRACT

In some implementations, one or more computing devices receive data indicating selection criteria for a cohort through an interface. The one or more computing devices determine a first set of candidates classified as having attributes that satisfy the selection criteria. The one or more computing devices also determine a second set of candidates that satisfy a subset of the selection criteria and are determined to not satisfy a same one or more criteria of the selection criteria. The one or more computing devices provide output data through the interface that includes (i) data indicating the first set of candidates, (ii) data indicating the second set of candidates, and (iii) data indicating the one or more selection criteria not satisfied by the members of the second set of candidates.

21 Claims, 19 Drawing Sheets

(56) References Cited

U.S. PATENT DOCUMENTS

| | | |
|---|---|---|
| 7,251,609 B1 | 7/2007 | McAlindon et al. |
| 7,415,447 B2 | 8/2008 | Shiffman et al. |
| 7,752,059 B2 | 7/2010 | Sweeney et al. |
| 7,809,601 B2 | 10/2010 | Shaya et al. |
| 7,809,660 B2 | 10/2010 | Friedlander et al. |
| 7,930,262 B2 | 4/2011 | Friedlander et al. |
| 7,937,275 B2 | 5/2011 | Schoenberg |
| 8,032,545 B2 | 10/2011 | Setimi |
| 8,065,180 B2 | 11/2011 | Hufford et al. |
| 8,380,531 B2 | 2/2013 | Paty et al. |
| 8,433,605 B2 | 4/2013 | Hufford et al. |
| 8,527,486 B2 | 9/2013 | Wittig et al. |
| 8,533,029 B2 | 9/2013 | Hufford et al. |
| 8,583,453 B2 | 11/2013 | Plummer et al. |
| 8,606,595 B2 | 12/2013 | Udani |
| 8,684,922 B2 | 4/2014 | Tran |
| 8,707,392 B2 | 4/2014 | Birtwhistle et al. |
| 8,966,548 B2 | 2/2015 | Busse et al. |
| 8,990,250 B1 | 3/2015 | Chowdry et al. |
| 9,020,971 B2 | 4/2015 | Bayliss et al. |
| 9,286,442 B2 | 3/2016 | Csoma et al. |
| 9,495,651 B2 | 11/2016 | O'Sullivan et al. |
| 9,514,655 B1 | 12/2016 | Nusbaum et al. |
| 9,659,254 B2 | 5/2017 | Achin et al. |
| 9,813,318 B2 | 11/2017 | Lyoob et al. |
| 10,231,622 B2 | 3/2019 | Soyao et al. |
| 10,304,000 B2 * | 5/2019 | Birnbaum ............. G06N 5/046 |
| 10,452,816 B2 | 10/2019 | Kidd et al. |
| 10,455,262 B2 | 10/2019 | Rieger et al. |
| 10,510,438 B2 | 12/2019 | Frazier et al. |
| 10,546,339 B2 | 1/2020 | Jiao et al. |
| 10,580,531 B2 | 3/2020 | Jiao et al. |
| 10,628,553 B1 | 4/2020 | Murrish et al. |
| 10,636,525 B2 | 4/2020 | Jiao et al. |
| 10,650,474 B2 | 5/2020 | Jiao et al. |
| 10,672,519 B2 | 6/2020 | Jiao et al. |
| 2002/0099570 A1 | 7/2002 | Knight |
| 2002/0143595 A1 | 10/2002 | Frank et al. |
| 2003/0065669 A1 | 4/2003 | Kahn et al. |
| 2003/0130871 A1 | 7/2003 | Rao et al. |
| 2004/0059697 A1 | 3/2004 | Forman |
| 2004/0172447 A1 | 9/2004 | Miller |
| 2004/0175700 A1 | 9/2004 | Geesaman |
| 2004/0210457 A1 | 10/2004 | Sameh |
| 2005/0165626 A1 | 7/2005 | Karpf |
| 2006/0184493 A1 | 8/2006 | Shiffman et al. |
| 2007/0179361 A1 | 8/2007 | Brown et al. |
| 2007/0250429 A1 | 10/2007 | Walser et al. |
| 2007/0294110 A1 * | 12/2007 | Settimi ................ G16H 10/60 705/3 |
| 2008/0010945 A1 | 1/2008 | McKenna et al. |
| 2008/0140444 A1 | 6/2008 | Karkanias |
| 2008/0294459 A1 * | 11/2008 | Angell ................ G16H 50/20 705/2 |
| 2009/0163183 A1 | 6/2009 | O'Donoghue et al. |
| 2009/0299766 A1 | 12/2009 | Friedlander et al. |
| 2010/0088245 A1 | 4/2010 | Harrison et al. |
| 2010/0218132 A1 | 8/2010 | Soni et al. |
| 2010/0250285 A1 | 9/2010 | Shelton |
| 2012/0035954 A1 | 2/2012 | Yeskel |
| 2012/0059735 A1 | 3/2012 | Su et al. |
| 2012/0065987 A1 | 3/2012 | Farooq et al. |
| 2012/0310670 A1 | 12/2012 | Pruitt |
| 2013/0262140 A1 * | 10/2013 | Friedlander ............ G16H 50/70 705/3 |
| 2013/0332190 A1 * | 12/2013 | Hoffman ................ G16H 10/20 705/3 |
| 2014/0067596 A1 | 3/2014 | McGovern et al. |
| 2014/0195297 A1 | 7/2014 | Abuelsaad et al. |
| 2014/0278474 A1 | 9/2014 | McClure et al. |
| 2014/0297311 A1 | 10/2014 | Jackson |
| 2014/0316793 A1 | 10/2014 | Pruit |
| 2014/0350954 A1 | 11/2014 | Ellis et al. |
| 2015/0073830 A1 * | 3/2015 | Hill ........................ G16H 10/60 705/3 |
| 2015/0178473 A1 | 6/2015 | Hufford et al. |
| 2015/0178474 A1 | 6/2015 | Hufford et al. |
| 2015/0193588 A1 * | 7/2015 | Nemoto ................ G06F 19/00 705/2 |
| 2015/0228041 A1 * | 8/2015 | Naley .................... G06Q 50/22 705/2 |
| 2015/0347682 A1 | 12/2015 | Chen et al. |
| 2015/0356582 A1 | 12/2015 | Turner, Jr. |
| 2016/0086505 A1 | 3/2016 | Hanlon |
| 2016/0098541 A1 * | 4/2016 | Haskell .................. G06F 19/00 705/2 |
| 2016/0140322 A1 * | 5/2016 | Menon .................. G16H 10/20 705/2 |
| 2016/0180053 A1 | 6/2016 | Fuertinger et al. |
| 2016/0357944 A1 | 12/2016 | Iyer et al. |
| 2017/0020444 A1 | 1/2017 | Lurie |
| 2017/0039341 A1 | 2/2017 | Shklarski et al. |
| 2017/0076049 A1 | 3/2017 | Miller |
| 2017/0235893 A1 * | 8/2017 | Cox ........................ G16H 40/67 705/2 |
| 2017/0235912 A1 | 8/2017 | Moturu et al. |
| 2018/0025125 A1 | 1/2018 | Crane et al. |
| 2018/0039726 A1 | 2/2018 | Boissel |
| 2018/0046780 A1 | 2/2018 | Graiver et al. |
| 2018/0056130 A1 * | 3/2018 | Bitran ................ A63B 24/0075 |
| 2018/0068083 A1 * | 3/2018 | Cohen .................... G16H 50/20 |
| 2018/0089376 A1 | 3/2018 | Tucker et al. |
| 2018/0150523 A1 | 5/2018 | Shiffman et al. |
| 2018/0242860 A1 | 8/2018 | LeBouef et al. |
| 2019/0006025 A1 | 1/2019 | Li |
| 2019/0012434 A1 | 1/2019 | Frazier |
| 2019/0080785 A1 | 3/2019 | Li |
| 2019/0122266 A1 | 4/2019 | Ramer et al. |
| 2019/0140892 A1 | 5/2019 | Jain et al. |
| 2019/0206521 A1 * | 7/2019 | Walpole ................ G16H 10/20 |
| 2020/0058382 A1 * | 2/2020 | Birnbaum ............. G06N 20/00 |
| 2020/0065879 A1 | 2/2020 | Hu et al. |
| 2020/0211679 A1 | 7/2020 | Pellini et al. |
| 2020/0211680 A1 * | 7/2020 | Sablinski ............... G16H 10/20 |
| 2020/0243167 A1 * | 7/2020 | Will ...................... G06N 5/003 |
| 2020/0350041 A1 | 11/2020 | Li |
| 2020/0357490 A1 | 11/2020 | Kartoun et al. |
| 2020/0411199 A1 | 12/2020 | Shrager et al. |

OTHER PUBLICATIONS

Flatiron.com [online], "OncoTrials," May 14, 2018, retrieved on Mar. 13, 2020, retrieved from URL <https://flatiron.com/oncology/clinical-trials/>, 4 pages.

Flatiron.com [online], "Press Release: Flatiron Health Announces Three Publications Studying a Feasible, Reliable, Scalable and Meaningful Real-World Progression Endpoint for Oncology Research," Aug. 22, 2019, retrieved on Mar. 13, 2020, retrieved from URL<https://flatiron.com/press/press-release/real-world-progression-2019/>, 4 pages.

Komen.org [online], "Types of Research Studies," Mar. 11, 2015, retrieved on Mar. 13, 2020, retrieved from URL<https://ww5.komen.org/BreastCancer/DifferentTypesofResearchStudies.html>, 5 pages.

Med.Standford.edu [online], "Cohort Discovery," retrieved on Mar. 13, 2020, retrieved from URL <https://med.stanford.edu/starr-tools/cohort-discovery.html>, 3 pages.

Michaeljfox.org [online], "Fox Trial Finder," retrieved on Mar. 13, 2020, retrieved from URL<https://www.michaeljfox.org/trial-finder>, 4 pages.

Miksad et al., "Small But Might: The Use of Real-World Evidence to Inform Precision Medicine," Clinical Pharmacology & Therapeutics, Jul. 2019, 106(1):87-90.

Mixpanel.com [online], "What is cohort analysis?," retrieved on Mar. 13, 2020, retrieved from URL <https://mixpanel.com/topics/cohort-analysis/>, 11 pages.

Murphy et al., "Visual Query Tool for Finding Patient Cohorts from a Clinical Data Warehouse of the Partners Healthcare System," Presented at Proceedings of AMIA Symposium, 2000:1174.

(56) References Cited

OTHER PUBLICATIONS

Nickelled.com [online], "Chapter 5: Top cohort analysis tools and resources," Dec. 12, 2018, retrieved on Mar. 13, 2020, retrieved from URL<https://www.nickelled.com/cohort-analysis/tools/>, 17 pages.
Pennic, "Life Image, Medel.ai Integrates to Support AI-Driven Clinical Trails," Nov. 6, 2018, retrieved from URL<https://hitconsultant.net/2018/11/06/life-image-medel-ai-partner-ai-driven-clinical-trails/#.Xmr7yqhKhZc>, 4 pages.
Rogers et al., "Composer: Visual Cohort Analysis of Patient Outcomes," Applied Clinical Informatics, Mar. 2019, 10(2):278-285.
Wikipedia.org [online], "Clinical trial," Feb. 17, 2020, retrieved on Mar. 13, 2020, retrieved from URL<https://en.wikipedia.org/wiki/Clinical_trial>, 18 pages.
Wikipedia.org [online], "Observational study," Feb. 17, 2020, retrieved on Mar. 13, 2020, retrieved from URL<https://en.wikipedia.org/wiki/Observational_study>, 4 pages.
Wikipedia.org [online], "Research," Mar. 7, 2020, retrieved on Mar. 13, 2020, retrieved from URL<https://en.wikipedia.org/wiki/Research>, 17 pages.
Grilo et al. "Pretreatment Patient Factors Predicting Attrition From a Multicenter Randomized Controlled Treatment Study for Panic Disorder," Comprehensive Psychiatry, Nov./Dec. 1998, 39(6):323-332.
U.S. Non-Final Office Action in U.S. Appl. No. 16/800,952, dated Sep. 1, 2020, 16 pages.
Ekonomou et al., "An Integrated Cloud-based Healthcare Infrastructure", IEEE Third International Conference on Cloud Computing Technology and Science, 2011, pp. 532-536.
FDA.gov [online], "FDA Offers Guidance to Enhance Diversity in Clinical Trials, Encourage Inclusivity in Medical Product Development", published on Nov. 9, 2020, retrieved on Mar. 11, 2021, retrieved from URL<https://www.fda.gov/news-events/press-announcements/fda-offers-guidance-enhance-diversity-clinical-trials-encourage-inclusivity-medical-product>, 3 pages.
Foxnews.com [online], "FDA Issues Final Guidance to Improve Diversity in Clinical Trials", published on Nov. 9, 2020, retrieved on Mar. 11, 2021, retrieved from URL<https://www.foxnews.com/health/fda-issues-final-guidance-improve-diversity-clinical-trials>, 7 pages.
Hammond et al., "Connecting Information to Improve Health", Health Affairs, Feb. 2010, 7 pages.
Opb.org [online], "OHSU's COVID-19 Study Accused of Racial Bias", Published on Jun. 6, 2020, retrieved on Mar. 11, 2021, retrieved from URL<https://www.opb.org/news/article/key-to-oregon-ohsu-covid-19-study-accused-of-racial-bias/>, 8 pages.
Oregonlive.com [online], "OHSU ends massive coronavirus study because it underrepresented minorities, university says", published on Aug. 27, 2020, retrieved on Mar. 11, 2021, retrieved from URL<https://www.oregonlive.com/coronavirus/2020/08/ohsu-drops-massive-coronavirus-study-because-minorities-didnt-sign-up-university-says.html>, 4 pages.
Statsoft, "Neural Networks", published in 2002, retrieved on Apr. 14, 2004, retrieved from URL<http://www.obgyn.cam.ac.uk/cam-only/statsbook/stneunet.html>.
U.S. Final Office Action in U.S. Appl. No. 16/800,952, dated Jan. 19, 2021, 24 pages.
DeAngelis, "Patient Monitoring, Big Data, and the Future of Healthcare," Wired.com, Aug. 6, 2014, retrieved at URL<https://www.wired.com/insights/2014/08/patient-monitoring-big-data-future-healthcare/>, 6 pages.
Dias et al., "Wearable Health Devices—Vigtal Sign Monitoring, Systems and Technologies," Sensors, Jul. 25, 2018, 18(8):2414.
Hayhurst, "How Network Monitoring Keeps Healthcare Devices and Patients Safe," HealthTech, May 7, 2020, retrieved at URL<https://healthtechmagazine.net/article/2020/05/how-network-monitoring-keeps-healthcare-devices-and-patients-safe>, 8 pages.
Kakria, "A Real-Time Health Monitoring System for Remote Cardiac Pateints Using Smartphone and Wearable Sensors," International Journal of Telemedicine and Applications, Nov. 12, 2015, vol. 2015, Article ID 373474, 11 pages.
Lenane, "Continuous Heart Monitoring Key to Identifying Cause of Cryptogenic Stroke," Diagnostic and Interventional Cardiology, Nov. 16, 2015, retrieved at URL<https://www.dicardiology.com/article/continuous-heart-monitoring-key-identifying-cause-cryptogenic-stroke>, 4 pages.
PaloAltoNetworks.com, "Monitor Device Health," Panorama Administrator's Guide Version 8.1, last updated Jun. 17, 2020, retrieved at URL<https://docs.paloaltonetworks.com/panorama/8-1/panorama-admin/manage-firewalls/device-monitoring-on-panorama/monitor-device-health.html>, 3 pages.
Phaneuf, "Latest Trends in Medical Monitoring Devices and Wearable Health Technology," BusinessInsider.com, Jan. 31, 2020, retrieved at URL<https://www.businessinsider.com/wearable-technology-healthcare-medical-devices>, 8 pages.
Smith et al., "Performance Measurement for Health System Improvement: Experiences, Challenges and Prospects," Proceedings of WHO European Ministerial Conference on Health Systems, Jun. 25-27, 2008, Tallinn, Estonia, 28 pages.
Tucker, "Five of the Best Health Monitoring Devices," TheGuardian.com, Aug. 21, 2016, retrieved at URL<https://www.theguardian.com/technology/2016/aug/21/five-best-cardio-health-monitoring-devices>, 9 pages.
U.S. Office Action in U.S. Appl. No. 16/877,162, dated Jul. 6, 2020, 12 pages.
Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.

\* cited by examiner

TECHNIQUES FOR SELECTING COHORTS FOR DECENTRALIZED CLINICAL TRIALS FOR PHARMACEUTICAL RESEARCH

BACKGROUND

Many research studies involve observing cohorts of subjects and performing data analysis to draw conclusions from the observations. In many cases, the step of defining a cohort can be a difficult and time-consuming manual task. For example, data of various types and from disparate sources may need to be assessed to determine the suitability of each individual candidate. In addition, even after a cohort is defined, there is a significant chance that some of the cohort members may not follow the steps required for the research study, which may not allow all of the data needed for the study to be generated.

SUMMARY

In some implementations, a computer system is configured to use machine learning techniques to enhance the process of defining and managing cohorts for scientific research. The system can provide tools that perform or assist in many aspects of research, including the selection or definition of cohorts. For example, the system can provide a search interface that enables a user to query a database of candidate subjects to identify subjects that match a set of selection criteria, e.g., inclusion criteria specifying conditions needed to be included in the cohort. Through the interface, the system can provide an indication of candidates that match the criteria. The system can also indicate groups of candidates that lack one or more requirements, but could comply with the selection criteria if certain further actions are taken. The system can use the database and machine learning models to suggest actions to obtain an appropriate cohort. For example, the system can assist the user in defining selection criteria, for example, by suggesting criteria or changes to criteria based on results from a database and predictions of models trained using examples of previous research studies. Similarly, the system can assess the level of difficulty of helping individuals or groups to reach eligibility for a research study.

The system can be used to generate customized communications and interactions for members of a cohort and candidates for a cohort. For example, the system can initiate customized communications and interactions for members of a cohort that are predicted, using one or more models, to increase the likelihood of a desired outcome, such as completion of a study, providing data, maintaining a behavior, and so on. As another example, the system can identify the differences between the data profiles of candidates and a set of selection criteria, such as missing data or characteristics that do not align with the selection criteria. The system can then identify candidates that do not meet the selection criteria that are predicted to be most capable of becoming able to meet the selection criteria. The system can generate communications or interactions customized for individual candidates and respectively tailored to enable the candidates to meet the selection criteria.

In some implementations, the system can use the analysis of prior studies and the contents of a database to design or suggest research questions and other research study parameters (e.g., size, duration, scope, data collection activities, data types collected, etc.). From analysis of the database, the system can identify the types of subjects available and their attributes, as well as expected behaviors and actions of the subjects. The system can also identify the types of data that are available or are readily able to be collected for a study. From this information, the system can predict research areas or even specific research questions that can be studied given the pool of candidates, the content of the database, and predicted behavior of the candidates. For example, the system can use tracked data for prior research studies to train one or more models to predict study parameters (e.g., the types of subjects needed, types of data collection needed, etc.) for establishing different study results. The system can then use the models to identify which research areas or questions are predicted to have a high confidence of being able to be addressed given the contents of a database. The system can then suggest these study types or study parameters as a new study or an alteration of an existing study.

As discussed further below, machine learning techniques can be used to automate and improve various aspects of program management based on identifying patterns within underlying data used for management. For example, techniques can be used to improve cohort outreach by increasing a population of candidate participants that are likely to satisfy selection criteria for a cohort. As another example, techniques can be used to provide improve cohort data analysis by using pattern recognition techniques to identify refinements to examination techniques, identify user behavioral patterns likely to impact research data quality, or provide recommendations of new research questions that may be of interest to a researcher. The techniques disclosed herein can leverage pattern recognition techniques to identify gaps between the data sets available for individuals and the needs of a research study.

During the cohort selection process for a new research study, the system generate predictions that can be used to determine a precise level of participant eligibility with respect to a set of cohort selection criteria. The system can apply machine learning models trained to identify patterns present within participant data accessible from an associated database. The participant data can include, for example, participant attributes (e.g., demographic information, diagnostic history), participant activity patterns (e.g., actions performed in prior research studies, exercise data, interaction data), as well as study-level data, such as historical study data (e.g., prior study outcomes, prior study design parameters), among others. The system classifies candidate participants (or groups of participants with similar attributes) using patterns recognized by the machine learning models with respect to eligibility for the cohort to be selected. For example, participants (or groups of participants) having attributes that satisfy all cohort selection criteria can be classified as being fully eligible, whereas other participants that satisfy some (but not all) cohort selection criteria can be classified by a level of partial eligibility.

The system can also provide an interface through which the researcher can interact with eligibility classifications so that the researcher can more effectively perform cohort selection. For example, the system can evaluate a researcher's search query to determine that cohort selection criteria is not likely to be satisfied, and in response, provide a recommendation to modify the cohort selection criteria to improve overall eligibility (e.g., increasing the number of participants that satisfy all cohort selection criteria), identify the level of eligibility for participants that satisfy some (but not all) selection criteria, among others. Data and recommendations presented through the interface can be updated in real-time so that the researcher can perform cohort selection with a greater level of interaction. For example, if the research adds a new key term for a search query, the system can update the processing of retrieved from the database in real-time to reflect updated eligibility classifications based on the new key term.

Another function of the system is to aid in the design of a new research study. The system can do this by, for example, making predictions about the likelihood of a successful outcome for a study, making recommendations of changes to the study, and even predicting topics or questions for additional studies. The system can identify patterns within historical study data (e.g., previously completed research studies) to determine whether a researcher's proposed study design will succeed. For example, a researcher can input information for a proposed study, for example, into a user interface for designing or building a study. The input can include a research question to be addressed by the study or other parameters for the study (e.g., cohort size, data to be collected, devices or technology to be used in the study, duration of the study, protocols or procedures to be used, etc.). The system can use the information about prior studies (e.g., research questions and topics, study parameters, and study outcomes) to evaluate whether the study being designed is likely to achieve one or more outcomes, such as completion of the study by at least a minimum number of participants, achieving a level of statistical validity, achieving a desired level of precision, and so on. The system may generate a likelihood, for example, a confidence score, for each of one or more types of potential study outcomes. This can be done by comparing the proposed parameters for the new study being designed with the parameters of the prior studies to determine how similar the proposed parameters are to studies that achieved the outcomes or those that did not achieve the outcomes. To better assess the likelihood, the system can also examine the variability in outcomes, and the correlations among different outcomes and different study parameters or combinations of study parameters. One way the system can provide this functionality is to train a machine learning model to predict the outcome of a study based on study parameters, where training is based on the examples of prior studies and their outcomes.

The system can also use data analysis, heuristics, natural language processing, machine learning models, and other techniques to provide automated recommendations for designing a study. These can include recommendations to adjust study parameters to encompass a larger set of candidates for a cohort when more participants are needed to meet a target level (e.g., to reach a researcher's target level, a typical level for the study type, a level needed for statistical validity, etc.). The recommendations can be to adjust study parameters to encompass a smaller set of candidates, for example, to better tailor the composition of a cohort to participants that are more likely to be engaged and retained for the duration of the study. Other recommendations may be made to help align study parameters with those that are typical or expected in the field. For example, the system may evaluate the records for studies in a research area (e.g., medical studies related to a particular disease or behavior) and suggest adjusting a study duration, cohort size, set of data collected, or other study parameter to align with the parameters commonly used in that research area.

The system can provide various other recommendations, such as additional research questions for the researcher to consider, survey questions to provide participants during the research study, techniques to improve participant engagement and/or interaction during the study, among others. As discussed above, the predictions, recommendations, and data generated by the system can be presented to a researcher through an interactive user in real time so that the researcher can receive automated feedback on techniques to improve a study being designed (e.g., improving techniques used to conduct a research study, adjusting the overall research question that is investigated, increasing the likelihood of a successful outcome for the study, etc.).

The system described herein can automate research study management in a manner that addresses limitations of other research management software. For example, cohort identification in many research management software is often a manual and inefficient process that involves a researcher selecting of participants from a list aggregated across multiple tabular files, or from several systems as database exported reports. In such processes, a researcher performs manual review, analysis, and various selection of varying inclusion-based or exclusion-based parameters and criteria. As another example, the cohort selection process in research management software often does not provide the researcher with access to underlying candidate participant data that is used for eligibility determinations. As a result, while a researcher may determine that a participant is eligible or ineligible, they often do not have access to or ability to analyze the data used by software to make this determination (thereby preventing the researcher from interactively adjusting cohort selection criteria in the manner disclosed within this specification).

Additionally, the architecture of the system provides various technological improvements that can be used by research management software to predictively evaluate types of research data, such as participant data (e.g., participant attributes, participant activity patterns), historical study data (e.g., study design parameters, study outcome data), among others. For example, the techniques described herein enable the system to determine participant eligibility for a cohort with greater precision and thereby provides greater utility to a researcher compared to the generalized eligibility determine (e.g., "eligible" or "not eligible") computed using some research management software.

In one general aspect, a method performed by one or more computing devices includes: receiving, by the one or more computing devices, data indicating selection criteria for a cohort, the data being received through an interface provided by the one or more computing devices; accessing, by the one or more computing devices, a database comprising attributes of a plurality of subjects; determining, by the one or more computing devices and based on data from the database, a first set of candidates classified as having attributes that satisfy the selection criteria; determining, by the one or more computing devices and based on data from the database, a second set of candidates that are (i) not included in the first set of candidates, and (ii) classified as satisfying a subset of the selection criteria, wherein the second set of candidates are each determined to not satisfy a same one or more criteria of the selection criteria; and providing, by the one or more computing devices, output data through the interface that includes (i) data indicating the first set of candidates, (ii) data indicating the second set of candidates, and (iii) data indicating the one or more selection criteria not satisfied by the members of the second set of candidates.

In some implementations, receiving the data indicating the selection criteria includes receiving the data indicating the selection criteria from a client device over a computer network. Providing the output data that indicates the first set of candidates and the second set of candidates includes providing the output data to the client device over the computer network.

In some implementations, the method includes accessing a database comprising information indicating attributes and activities of a plurality of subjects. The database can include sensor data acquired from mobile devices associated with the subjects. The first set of candidates and the second set of candidates are determined based at least in part on the sensor data in the database.

In some implementations, the method includes generating, for each subject in a plurality of subjects, a prediction score indicative of a prediction for the subject using one or more machine learning models that have been trained based on attributes and activities of other subjects, wherein at least one of the first set of candidates or the second set of candidates is determined based at least in part on the prediction scores.

In some implementations, the method includes determining whether to include a subject in a set of candidates for a cohort based on (i) an amount of the selection criteria that subject satisfies and (ii) a prediction score for the subject that is indicative of a probability of the subject achieving a predetermined outcome, wherein the predictive score is generated using one or more machine learning models that have been trained based on attributes and activities of other subjects and data indicating whether the other subjects achieved the predetermined outcome.

In some implementations, the method includes: identifying multiple second sets of candidates, wherein each of the multiple second sets of candidates is formed of candidates that satisfy only a same proper subset of the selection criteria, wherein the different second sets of candidates satisfy different proper subsets of the selection criteria; and providing, for display along with the data indicating the first set of candidates, (i) data indicating each of the multiple second sets of candidates and (ii) an indication, for each of the multiple second sets of candidates, of one or more items of the selection criteria that are not satisfied by the members of the second set of candidates.

In some implementations, the method includes: providing data causing display of one or more interactive controls corresponding to the first set of candidates; and in response to receiving data indicating user interaction with the one or more interactive controls, adding members of the first set of candidates to a cohort.

In some implementations, the method includes: providing data causing display of one or more interactive controls corresponding to the second set of candidates; and in response to receiving data indicating user interaction with the one or more interactive controls, adding members of the second set of candidates to a cohort.

In some implementations, the method includes: providing data causing display of one or more interactive controls corresponding to the second set of candidates; and in response to receiving data indicating user interaction with the interactive control, altering the selection criteria to remove the one or more criteria not satisfied by the members of the second set of candidates.

In some implementations, the interface is a user interface. Providing the data through the interface includes providing the data for presentation in a first portion of the user interface. The method can include providing one or more interactive elements to enable selection of a representation of the first set of candidates or the second set of candidates; providing a second portion of the user interface to display information about candidates within a selected set of candidates; and in response to receiving data indicating user selection of one of the sets of candidates, providing, for display in the second portion of the user interface, a list of candidates in a selected set of candidates and attributes of the listed candidates. The information presented for display in the second portion of the user interface can include indications of predictions generated using machine learning models, such as likelihoods or classifications for individuals with respect to different outcomes.

In some implementations, the interface is an application programming interface.

In some implementations, the method includes: determining a target amount of members for the cohort; and determining that an amount of participants included in the first set of candidates is less than the target amount of cohort participants. Determining or providing an indication of the second set of candidates can be based on determining that the amount of participants included in the first set of candidates is less than the target amount of cohort participants. Other actions, such as the recommendation of changes to the selection criteria and/or actions to communicate with individuals to increase their eligibility to meet the selection criteria may additionally or alternatively be performed in response to determining that the first set of candidates does not provide the desired target amount.

In some implementations, the selection criteria are associated with a research study. The method can include obtaining log data corresponding to each candidate included in a particular set of candidates. The log data includes at least one of a health history, a demographic profile, health data collection patterns, or actions of a user when previously participating in a research study. The method can include: determining, for each candidate included in the particular set of candidates and based on the log data, a prediction whether the candidate will complete the research study if selected to be included in a cohort for the research study. For example, the prediction can include a probability score, classification, or confidence score generated by a machine learning model. The method can include providing, through the interface, an indication of the predictions determined for the particular set of candidates.

In some implementations, the data indicating the first set of candidates includes an amount of members included in the first set of candidates; and the data indicating the second set of candidates includes an amount of members included in the second set of candidates.

In some implementations, the selection criteria includes a primary cohort selection criterion and multiple secondary cohort selection criterion. Determining the second set of candidates includes: identifying a group of candidates classified as satisfying the primary cohort selection criterion; obtaining log data for each member of the group of candidates; determining, for each member of the group of candidates, an amount of the secondary cohort selection criterion that are satisfied by a particular member; and selecting, from among the group of candidates and for inclusion in the second set of candidates, members that are determined to satisfy a threshold amount of secondary cohort selection criterion.

In some implementations, the method includes: determining that an amount of members of the second set of candidates is below a predetermined threshold; and providing, through the interface, a recommendation to change one or more of the selection criteria based on determining that the amount of members of the second set of candidates is below the predetermined threshold.

In some implementations, each of the members of the second set of candidates satisfies the cohort criteria except for a particular cohort selection criterion; and providing the recommendation to change one or more of the selection criteria includes providing, through the interface, a recommendation to remove the particular cohort selection criterion.

In some implementations, the method includes: identifying a constraint of the selection criteria to alter based on the size of one or more sets of candidates lacking a same one or more selection criteria; providing data for a user interface element for altering the identified constraint; and in response to receiving data indicating user interaction with the user interface element: altering the constraint to form revised cohort selection criteria, defining new sets of candidates for the revised cohort selection criteria, and providing indications of the new sets of candidates.

In another general aspect, a method performed by one or more computing devices includes: obtaining, by the one or more computing devices, log data for a group of subjects identified in a database, wherein the log data identifies information collected for members of the group of subjects during participation in a set of previously completed research studies; identifying, by the one or more computing devices, a set of attributes shared by members of the group of subjects based on the information collected for members of the group of subjects during participation in the set of previously completed research studies; using, by the one or more computing devices, one or more machine learning models to determine one or more parameters for a research study based on the set of attributes shared by members of the group of subjects, wherein the one or more machine learning models are trained to predict parameters of research studies including types of data to be collected; and providing, through an interface, data indicating the one or more parameters for the research study.

In some implementations, the set of attributes shared by members of the group of subjects includes an attribute identifying a disease condition; and the one or more parameters for the program includes a parameter specifying evaluation criteria associated with the disease condition.

In some implementations, the set of attributes shared by members of the group of subjects includes an attribute identifying a behavioral pattern; and the one or more parameters for the program includes a parameter specifying a survey question corresponding to the behavioral pattern to be provided to members of the group of subjects.

In some implementations, the one or more parameters for the program includes a parameter specifying selection criteria for the program; and the method further includes: determining, from among the group of subjects, a subset of subjects as having attributes that satisfy the selection criteria; and providing, through the interface, data indicating the subset of subjects.

In some implementations, the log data includes a set of historical actions performed by members of the group of subjects; and determining the one or more parameters for the program includes: determining, using the one or more trained machine learning models, a set of future actions likely to be performed by members of the groups of subjects; and identifying one or more operations to be performed during the program to evaluate the set of future actions.

In some implementations, the log data includes sensor data collected by computing devices associated with members of the group of subjects during participation in the set of previously completed research studies; and determining the one or more parameters for the program includes: determining a physiological parameter that is (i) included in the sensor data collected by computing devices associated with members of the group of subjects and (ii) was monitored for members of the group of subjects during participation in the set of previously completed research studies; and identifying one or more operations to be performed during the program to evaluate the physiological parameter.

In some implementations, the one or more machine learning models comprise at least one of a neural network, a support vector machine, a classifier, a regression model, a clustering model, a decision tree, a random forest model, a genetic algorithm, a Bayesian model, or a Gaussian mixture model.

In another general aspect, a method performed by one or more computing devices includes: obtaining, by the one or more computing devices, data from a database indicating attributes or activities of a subject; generating, by the one or more computing devices and based on the data from the database, feature data indicative of the attributes or activities of the subject; providing, by the one or more computing devices, the feature data to one or more models that are based on training data indicating attributes of different subjects and actions of the different subjects; obtaining, by the one or more computing devices, an output from the one or more models that is indicative of whether the subject will perform an action; and determining, by the one or more computing devices, a suitability of the subject for inclusion in a cohort based on the output from the one or more trained machine learning models.

In some implementations, one or more models comprise one or more trained machine learning models, wherein the one or more trained machine learning models have been trained based on the training data indicating attributes of different subjects and actions of the different subjects.

In some implementations, the trained machine learning models have been trained based on training data indicating actions of the different subjects during research studies in which the different subjects were enrolled.

In some implementations, the one or more models comprise at least one of a neural network, a support vector machine, a classifier, a regression model, a clustering model, a decision tree, a random forest model, a genetic algorithm, a Bayesian model, or a Gaussian mixture model.

In some implementations, the output from the one or more models is indicative of a prediction whether the subject will perform a predetermined action in the future; and the one or more models are based on data indicating whether the different subjects performed the predetermined action.

In some implementations, the particular predetermined action includes at least one of: completion of a research study; continuing a particular type of activity for at least a minimum amount of time; use of a medical device; use of a mobile device; use of a software interface; providing a particular type of data; a type or frequency of communication; responding to a request; responding to a communication of a certain type (e.g., email, text message, phone call, etc.); performance of a physical activity; or compliance with a medication regimen.

In some implementations, the method includes providing, for display on a user interface, output data comprising: a score based on the output from the one or more models; an indicator of the determined suitability of the subject; a recommendation to include or exclude the subject from the cohort, wherein the recommendation is based on the determined suitability of the subject.

In some implementations, determining the suitability of the subject for the cohort includes comparing the output from the one or more models to a predetermined threshold.

In some implementations, the method includes selecting an action, from among a plurality of candidate actions, based on the determined suitability, wherein the selected action includes at least one of: filtering a set of candidates such that the subject is included or excluded based on the determined suitability; providing a recommendation to include or exclude the subject from the cohort; or presenting or declining to present the subject as a candidate for the cohort;

In some implementations, the output from the one or more models is a confidence score, a classification, or a probability score.

In some implementations, the method includes accessing data indicating that a research study associated with the cohort specifies performance of the action by members of the cohort. Determining the suitability of the subject is based on the data indicating that a research study associated with the cohort specifies performance of the action by members of the cohort.

In some implementations, cohort selection criteria for the cohort includes a criterion related to performing the action, and determining the suitability of the subject for inclusion in the cohort includes determining, based on the output from the one or more models, whether the user satisfies the cohort selection criteria.

In some implementations, cohort selection criteria for the cohort do not include a criterion performing the action, and determining the suitability of the subject for inclusion in the cohort includes determining, separate from eligibility according to the cohort selection criteria, whether the user is suitable for the cohort based on the output from the one or more models.

In some implementations, the set of feature scores is based on sensor data that is acquired by one or more sensors during one or more activities of the subject or that indicates one or more attributes of the subject.

In some implementations, the set of feature scores is based on records of one or more interactions of the subject with a mobile device.

In another general aspect, a method performed by one or more computing devices includes: obtaining, by the one or more computing devices, data from a database indicating attributes or activities of a subject; identifying, by the one or more computing devices and based on the data from the database, that the subject does not satisfy an selection criterion for a cohort; generating, by the one or more computing devices, a score for each of a plurality of actions to cause the subject to satisfy the selection criterion, the scores being based on data in the database indicating actions of other subjects with respect to the selection criterion; selecting, by the one or more computing devices, one or more actions from among the plurality of actions based on the scores; and initiating, by the one or more computing devices, the selected one or more actions.

In some implementations, generating the score for each of the plurality of actions includes generating the scores using one or more models that are based on data in the database indicating the actions of the other subjects with respect to the selection criterion.

In some implementations, the one or more models are trained machine learning models that have been trained to predict a likelihood of a response of an subject to one or more of the actions in the plurality of actions based on input data indicative of attributes or activities of the subject.

In some implementations, the one or more machine learning models have been trained based on data indicating progressions of one or more subjects from ineligibility for the selection criterion to eligibility for the selection criterion.

In some implementations, the one or more machine learning models have been trained based on actions of one or more subjects in response to one or more of the actions in the plurality of actions.

In some implementations, the one or more machine learning models have been trained based on examples of subjects that did not change status to eligibility in response to actions in the plurality of actions.

In some implementations, the one or more models comprise at least one of a neural network, a support vector machine, a classifier, a regression model, a clustering model, a decision tree, a random forest model, a genetic algorithm, a Bayesian model, or a Gaussian mixture model.

In some implementations, the plurality of actions are initiating communications of different types or communications through different communication channels.

In some implementations, the plurality of actions include requesting at least one of completion of a survey, an indication of consent, performance of a medical test, acquisition of a medical device, installation a software application, beginning a behavior, ending a behavior, access to mobile device data or sensor data, or records from a third-party data repository.

The details of one or more implementations are set forth in the accompanying drawings and the description below. Other potential features and advantages will become apparent from the description, the drawings, and the claims.

BRIEF DESCRIPTION OF THE DRAWINGS

In the drawings, like reference numbers represent corresponding parts throughout.

DETAILED DESCRIPTION

Figure 1:
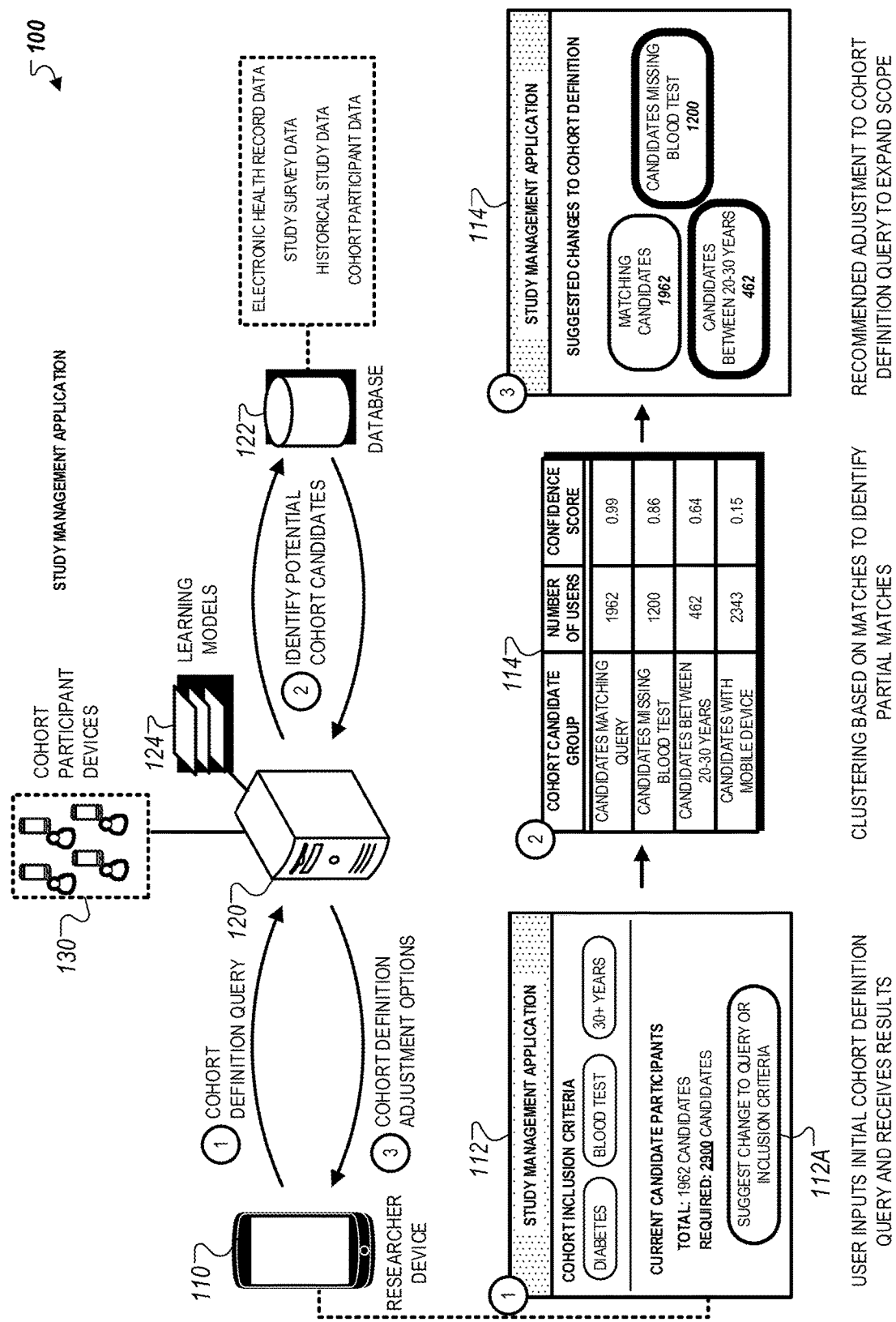
FIG. 1 illustrates an example of a technique for providing an interface that enables dynamic adjustment of cohort selection criteria for a new research study.

In general, this disclosure describes systems and techniques for applying machine learning techniques to automate and/or improve various aspects of research study management based on identifying patterns within underlying data used to for management. For example, during the cohort selection process for a new research study, the system generates predictions that can be used to determine a precise level of participant eligibility with respect to a set of cohort selection criteria. The system can apply machine learning models trained to identify patterns present within participant data accessible from an associated database. The system classifies candidate participants (or groups of participants with similar attributes) using patterns recognized by the machine learning models with respect to eligibility for the cohort to be selected. For example, participants (or groups of participants) having attributes that satisfy all cohort selection criteria can be classified as being fully eligible, whereas other participants that satisfy some (but not all) cohort selection criteria can be classified by a level of partial eligibility.

Research management software can be used to assist a researcher in designing, conducting, and evaluating a research study. Typically, a researcher develops a research question and a hypothesis to conduct an experiment to evaluate the research question. Many research studies involve identifying and enrolling a group or "cohort" of subjects for which data will be collected over a period of time. In health research, the subjects are often human subjects.

Many health research studies often involve evaluating data of cohort participants (e.g., participant data) to develop a statistical conclusion with respect to a given research question. For example, a research question for evaluating the effect of exercise on sleep activity involves investigating participants' sleep activity data in relation to exercise data for the possibility of a statistical correlation. To develop a cohort, a group of participants are often identified based on health history, demographics profile, relevant tests, queries, health data collection such as blood samples, genomic data, measurable signals, environmental considerations, behavioral and lifestyle informatics.

The techniques in this document can be used to assist in or automate various aspects of research study design. They can also be used to perform many aspects of defining and engaging with cohorts of subjects during a research study. For example, the system can use a search engine or other search functionality to identify candidates to be included in a cohort. The system can provide recommendations of subjects to include or exclude, in some implementations based on predictions of machine learning models. The system can also provide recommendations of changes to cohort selection criteria and other study parameters.

The system can identify subjects that do not satisfy cohort selection criteria and identify which subjects have the lowest burden to become eligible according to the cohort selection criteria. For example, the system can identify the "gaps" between subject data profiles and the needed characteristics for eligibility for a cohort, and then perform an automated process to identify and initiate actions to close the gaps. The actions can be personalized or tailored for individual subjects, based on the gap identified for the subject (e.g., the change needed for the subject to become eligible) and information about the subject in a database (e.g., data indicating prior behavior or responses of the subject). The actions the system initiates can involve, for example, requesting records (e.g., electronic health records (EHR) or electronic medical records (EMR)), initiating data collection by a mobile device of a subject, initiating communications with a client device (e.g., causing a survey or other interaction to be presented), etc. The actions can include encouraging behavior change by a subject (e.g., changes in sleep, diet, exercise, etc.) to bring the subject into eligibility for inclusion in a cohort.

The techniques in this document can be used to design and carry out various types of research studies, including observational studies, prospective cohort studies, case-control studies, randomized controlled trials (RCTs), clinical trials, observational trials, interventional trials, treatment trials, prevention trials, screening trials, and so on. The techniques can be used to define study parameters and select cohorts for studies that involve further data collection, in which cohort members provide data for a period of time after the study begins. The techniques can also be used to define study parameters and select cohorts for studies that are based on previously collected or generated data.

The cohort selection tools of the system can provide automated detection of individuals satisfying inclusion criteria or exclusion criteria for clinical trials, in real-time.

Today, only 5% of the US population participates in clinical research. With the rise of new software tools that make research faster, cheaper, and more accessible and with a forward-looking FDA digital health team, the time is ripe for a clinical trial paradigm shift. One of the advantages of the systems described herein is the ability to assist in software-enabled clinical trials, e.g., clinical trials that involve mobile applications, web interactions, and other software. The systems described herein can be used for remote clinical research, such as when participants in a study are located remotely from the researchers and may be dispersed throughout a country or even across the world. The system provides the scale and precision for clinical grade applications, including use in clinical trials.

The platform and services discussed herein are designed to make clinical trials and registries more accessible and less costly. This can be done by replacing patient visits at investigator sites with technology-enabled interactions at more convenient locations, including patients' homes. Growing numbers of biopharma, life science companies, contract research organizations (CROs), and non-profit researchers need a virtual research platform to capture clinical study data in between clinic visits, as well as during or instead of clinic visits. The platform supports an integrated suite of user-friendly, highly configurable applications that support electronic consent (e.g., "eConsent"), electronic patient-reported outcomes (ePRO)/electronic clinical outcome assessment (eCOA), patient engagement, telehealth virtual visits, site data capture, and medical device and consumer sensor connection. The platform enables researchers to modernize clinical research for customers, participants, and sites, and makes virtual research approaches the standard in studies and registries.

FIG. 1 illustrates an example of a technique for providing an interface that enables dynamic adjustment of cohort selection criteria for a new research study. In this example, a system 100 enables a researcher to receive feedback in real-time while selecting a cohort for a new research study. As discussed in greater detail below, the system 100 provides an interface 112 through which the researcher can submit cohort selection criteria and receive search results for candidate participants identified to satisfy the cohort selection criteria. The researcher can also receive other results indicating groups of participant candidates that are partially eligible and may also be worth considering. In this way, the researcher is provided with information enabling him/her to make adjustments in real-time to cohort selection criteria to improve eligibility for the research study.

The system 100 includes a researcher device 110, a computer system 120 (e.g., a server system), and multiple participant devices 130 that exchange data communications over a network. The researcher device 110 is configured to run a study management application through which a researcher can design and manage new, ongoing, and completed research studies. The computer system 120 accesses a database 122 storing data for participants associated with the participant devices 130 (as well as other types of data). The computer system 120 also has access to machine learning models 124 that are applied to generate predictions associated with a research study, as described throughout. The participant devices 130 are each configured to run a study participation application through which the participants can access content associated with a research study.

In the example shown in FIG. 1, the computer system 120 initially receives a query from a researcher device 110. The query includes keywords associated with the cohort selection criteria. In the example shown in FIG. 1, the query includes three keywords that are each associated with a unique cohort selection criterion (e.g., being diagnosed with a disease condition, medical history including a laboratory test, and participant age range). In this example, the cohort selection criteria is used to seek candidate participants that have been diagnosed with diabetes, have at least one blood test in their medical history file, and are older than 30 years old. The cohort selection criteria, in this example, may be related to a research study for evaluating the effect of exercise on measured glucose levels for middle-aged individuals diagnosed with diabetes.

The computer system 120 identifies potential cohort candidates that may potentially satisfy the cohort selection criteria. In performing this identification, the computer system 120 accesses data stored in the database 122. The accessed data can include information for individuals that have participated in previously conducted research studies, individuals that have agreed to participate in a research campaign, or individuals who have otherwise consented to their health data being used for research purposes.

As shown in FIG. 1, in response to receiving the query, the computer system 120 identifies a total of 1,962 candidates that are determined to satisfy the three cohort selection criteria specified by the request. That is, the computer system 120 determines, based on accessing the database 122, that 1,962 individuals have been diagnosed with diabetes, obtained at least one blood test, are older than thirty years old, and are available for selection in the cohort for the new research study. However, because this number is below the required 2,900 number of candidates that the researcher requires for the research study, an interface element 112A is displayed to the researcher to receive additional analysis regarding a change to the query or cohort selection criteria.

Once a researcher selects interface element 112A, the computer system 120 accesses the database 122 to identify additional participant candidates that partially satisfy the cohort selection criteria. The additional participant candidates were not included in the initial 1,962 candidates since the computer system 120 determined that their respective attributes did not satisfy all three cohort selection criteria specified in the query. In other words, the attributes of the additional participant candidates satisfies one or two of the three cohort selection criteria.

For example, as shown in table 114, the computer system 120 clusters additional participants into three groups in addition to the original group that was identified as being eligible for cohort selection. The first additional group includes candidates that satisfy the diabetes and age criteria, but do not have a blood test on file. The second additional group includes candidates that satisfy the diabetes and blood test criteria, but are younger than 30 years old. The computer system 120 also identifies a third additional group of participants that satisfy a criteria that may not have been explicitly specified by the query, such as the possession of a mobile device. In this example, the third group of participants is identified based on an automated determination that access to a mobile device may be important for the cohort selection process. Table 114 also identifies the number of candidates that are identified for each group. For instance, the initial group includes 1,962 participants, while the second, third, and forth groups include 1,200, 462, and 2,342 candidates, respectively.

When identifying additional candidates, the computer system 120 also evaluates corresponding participant data using machine learning models to compute a confidence score for each group. The confidence scores can be used as a way to prioritize selection of candidates from amongst the different groups. For example, the confidence scores can represent a predicted likelihood that selection of candidates included a particular group would help achieve study objectives.

As shown in table 114, the value of the confidence score computed for the second group (e.g., candidates missing blood test) is higher than the value of the confidence score computed for the third group (e.g., candidates aged between 20-30 years old) since the age criteria is given greater importance or weight relative to the blood test criteria. For instance, because candidates can obtain a blood test after they enroll in the study (but they are unable to change their age), the computer system 120 applies a greater significance to satisfying the age criteria. Likewise, while access to a mobile device may improve the likelihood that a participant will complete study response surveys, the value of the confidence score for this group is the lowest as the grouping has no bearing on the research objective to evaluate the effect of exercise on blood glucose levels of individuals with diabetes.

The computer system 120 generates updated results for the query and displays them through interface 116 for user selection. As shown, the interface 116 identifies three groups that are identified to include candidates that potentially satisfy the cohort selection criteria specified in the query submitted through interface 112. The interface 116 identifies the initial group of 1,962 candidates (which satisfy the cohort selection criteria), as well as two additional groups determined to have confidence scores that satisfied a threshold value (e.g., 0.60). In this example, though the fourth group was identified by the computer system 120 in table 114, this group is not identified in interface 116 since selection of candidates within this group for the cohort would diminish the research objective of the study.

In some implementations, the interface 116 can include other types of recommendation data in addition to (or as an alternative to) the identification of additional candidates that fully or partially satisfy the cohort selection criteria. In some instances, the interface 116 can identify suggestions for replacement cohort selection criteria that broaden the scope of eligibility of candidates. For example, the interface 116 may display a suggestion to expand age from 30 years or older (as specified in the original query) to 25 years or older. This change would allow candidates from the second group to be fully eligible for cohort selection. As another example, the interface 116 may display a suggestion to remove the blood test criteria since a large number of individuals may become eligible if this criteria were removed and instead placed as a condition for participation in the research study that would occur after cohort selection.

One of the major challenges in beginning a research study is selecting and enrolling a group of individuals to participate in the study. This cohort typically needs to provide data and comply with study protocols for a significant amount of time, for example, often weeks, months, or even years. Unlike many search systems, the computer system 120 can not only identify individuals that match selection criteria, but also provide additional assistance in the event that the number of matches is less than a desired amount. The computer system 120 can also evaluate whether individuals that match the selection criteria would provide an effective cohort, e.g., whether they can be expected to be engaged and retained in the study. The computer system 120 can also identify individuals that and groups of individuals that only partially match the selection criteria. The computer system 120 can provide recommendations that indicate how the selection criteria can be adjusted to expand the cohort and/or steps can be taken to improve the eligibility for individuals that do not satisfy all of the selection criteria.

A common challenge for cohort selection is that the group of available individuals known to fully satisfy the selection criteria is too small. For example, the total number of individuals matching the selection criteria may be less than a minimum threshold, which may be set by a user or determined by the computer system 120. In many cases, the cohort needs to have at least a minimum number of participants in order to meet norms or requirements in the research field, to provide statistical validity to results from the study, and so on. Even if the minimum number of participants is identified from profiles in the database 122, there is often a need to add additional participants for example, to add individuals of certain demographic backgrounds to improve statistical validity, to provide headroom or over-provisioning in the cohort to account for attrition among participants, and so on.

To address these challenges and assist in the selection of an effective cohort, the computer system 120 identifies, in addition to a group that meets all selection criteria, groups of individuals that only partially meet the selection criteria. For example different groups of individuals are identified, where each group includes individuals that each fail to satisfy the same subset of the selection criteria while each satisfying the rest of the selection criteria.

In this way, the computer system 120 can act as a search engine or search system to identify individuals that satisfy the selection criteria. The computer system 120 also provides analysis and recommendation functions to show how the selection criteria can be changed to encompass an appropriate group of individuals. The computer system 120 can also identify which individuals or groups of individuals that are not currently eligible are best suited to becoming eligible to meet the selection criteria. The computer system 120 can automatically interact with these individuals to collect needed data (e.g., survey responses, consent agreements, etc.), recommend behavior or other changes, or otherwise encourage individuals to become eligible for a particular research study.

As noted above, individuals may fail to be eligible for a given research study for different reasons. Each research study may have its own set of selection criteria specifying what is needed to participate. This may include a certain health status or disease status. Naturally, a study focusing on the effects of sleep on diabetes would need participants who have diabetes and who are able to provide data such as blood glucose measurements, sleep tracking data, and so on. When the computer system 120 searches for potential members in the cohort, one group may have all the characteristics and capabilities desired for the study. The computer system 120 also identifies other groups that lack different elements of the selection criteria. For example, a second group may include individuals that have diabetes and provide blood glucose data, but which do not provide sleep tracking data. A third group may include users that have diabetes and provide sleep tracking data but do not provide blood glucose data. A fourth group may include users that have diabetes but do not provide sleep or blood glucose data, or for which the ability to track that data is unknown or unverified. A fifth group may include individuals that provide tracking data for blood glucose and sleep, but which are not diagnosed as having diabetes.

The computer system 120 identifies these various groups of individuals and displays indications of the different groups of candidates on the user interface. This can quickly show a user the clusters of individuals registered in the database that could potentially participate in the cohort. Notably, it shows not only those that are exact matches, but groups that have different "near miss" profiles, where the members of each group lack a same one or more of the selection criteria. The user interface can show an indication of the size of the groups, for example, by indicating a number of members of each group, by showing visual elements representing the groups sized relative to the sizes of the groups, using color coding to indicate size with respect to a scale, and so on. Each representation of a group in the user interface can also include an indication of the one or more selection criteria that are not met by the members of that group. From this information, the user can quickly see which near-miss groups of users are registered in the database which could be brought into the cohort if certain selection criteria were modified, e.g., relaxed, removed, or otherwise changed.

The user interface can include, in conjunction with the representations of the different groups of individuals identified, one or more user interface controls to add the groups to the cohort being created. In some implementations, the representation of the group, e.g., a shape, text, or other element, can be interacted with to add a group of candidates to the cohort. For example, a region representing a group can simply be tapped, clicked, selected, or otherwise we interacted with to add the members in the group to the cohort. As additional examples, to add a group of individuals to a cohort the user may drag a representation of the group to a predefined region or click the checkbox associated with the group.

In the case of individuals that meet all of the selection criteria, the members in the group may be added automatically or simply by an action to confirm their addition to the cohort, such as clicking a representation for the group. To add other groups that do not meet all of the selection criteria, various options can be implemented. For example, the user interface may enable a user to select one of the groups and add it to the cohort, using this action as an instruction to the computer system 120 to broaden the selection criteria in the manner necessary so that it encompasses the newly selected group. As another example, selection of the group may trigger the computer system 120 to prompt the user to make a change to the criteria or confirm a change to the criteria that the computer system 120 suggests in order to encompass the new group. As another example, the user interface may be configured so that selection of a group not matching all of the selection criteria maybe used as a signal to the computer system 120 to communicate with the individuals in that group to remedy the issue that resulted in not having full eligibility for the cohort.

By providing the user interface showing the different groups of individuals identified and their varying levels of eligibility with respect to the selection criteria, the computer system 120 provides users the tools and flexibility to dynamically adjust the composition of the cohort from the search interface. The computer system 120 can also provide recommendations and context-specific, targeted guidance tailored for the specific cohort being defined. In other words, the computer system 120 can use the selection criteria for the study (including potentially the research question being addressed, the topic, the field, and so on), the identified groups, and information in the database to recommend improvements to the cohort. As discussed below, these improvements can include changes to the selection criteria, e.g. to encompass a larger number of candidates when needed, outreach to bring additional individuals into eligibility, and machine learning analysis to predict the likelihoods of individuals and groups of individuals to meet the needs of the study.

The computer system 120 can evaluate various factors to determine which changes to selection criteria to recommend. One technique is to compare size of group with the amount needed still in the cohort. The computer system 120 can identify one or more options that provide at least the minimum size needed. The computer system 120 can determine a score for each of the selection criteria, or at least those for which a group has been identified as lacking that criterion. The scores indicate the importance of that criterion with respect to the study, so the criteria predicted to be less important maybe relaxed or removed first. For example in a study about diabetes based on sleep, blood glucose, and diet in people age 35 to 55, the computer system 120 may determine that in order of importance from most important to least important the criteria would be listed as diabetes diagnosis, blood glucose data, sleep data, diet data, and participant age. Because of this, with age predicted to be least important (e.g., a change to the age requirement predicted to be least disruptive to the overall study goal), the computer system 120 can recommend a change to the age requirement to bring in at least some of the users in another group that has all of the selection criteria satisfied except for the age requirement. The computer system 120 may determine a magnitude of the change to make as well, to tailor the amount of change to the criteria to fit the characteristics of the individuals whose profiles are in the database. For example, rather than removing the age requirement entirely, the computer system 120 may recommend broadening the requirement of "between 35 to 55" to instead be a requirement of age "between 30 and 60," based on a determination by the computer system 120 at this age range expansion would include at least the minimum number of participants needed to complete the cohort. In other words, when one or more criteria are relaxed to expand the set of individuals encompassed, the computer system 120 may do so in an incremental or measured way, to reach the requirements for the size of the cohort while preserving as much as possible the original selection criteria.

Figure 2:
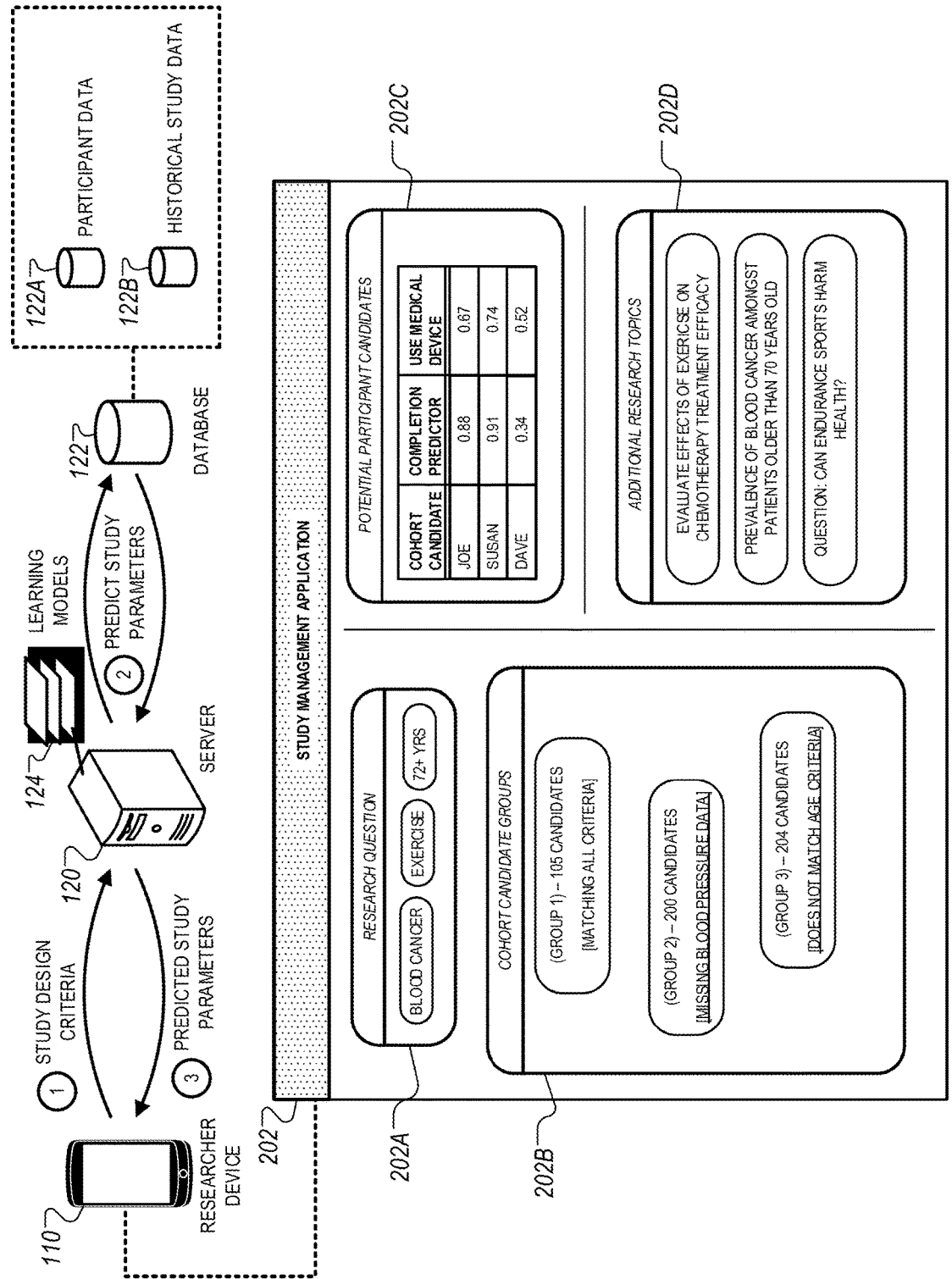
FIG. 2 illustrates an example of a technique for providing an interface that provides automated recommendations for adjusting aspects of new research study.

FIG. 2 illustrates an example of a technique for providing an interface that provides automated recommendations for adjusting aspects of new research study. In this example, the system 100 enables a researcher to receive feedback in real-time when designing a new research study. As discussed in greater detail below, the system 100 provides an interface 202 through which the researcher can submit a research question and receive data related to predicted study parameters. The data can be generated and/or modified in real-time to enable dynamic interactive design of a research study in an iterative fashion.

In the example shown in FIG. 2, the computer system 120 initially receives study design criteria from the researcher device 110. The query can be submitted through an interface element 202A presented through interface 202 of the study management application. In this example, the design criteria includes keywords representing conditions to be evaluated in the study (e.g., blood cancer, exercise activity, participant age).

The computer system 120 accesses the database 122 to predict study parameters. As shown, the computer system 120 applies the machine learning models 124 to evaluate participant data 122A and historical study data 122B. The evaluations are then used to predict study parameters that are displayed through the user interface 202. The participant data 122A includes participant-specific information (e.g., demographic information, laboratory tests, genomic data) and activity patterns associated with the participant (e.g., behavioral or lifestyle information, actions performed in previously conducted research studies, etc.). The historical study data 122B includes information for previously completed research studies, such as design parameters, outcome data, among others.

The computer system 120 predicts parameters for the design criteria specified in the query based on evaluating the participant data 122A and the historical study data 122B. For instance, in the example shown in FIG. 2, the computer system 120 predicts three types of study parameters. The first predicted study parameter involves possible participant candidates presented in interface element 202B of the interface 202. The candidate groups are identified based on clustering individual participants (as discussed in reference to FIG. 1) into groups that are likely to satisfy cohort selection criteria. As shown in FIG. 2, the computer system 120 identifies three groups. The first group ("GROUP 1") includes 105 candidates that satisfy all cohort selection criteria, the second group ("GROUP 2") includes 200 candidates that do not satisfy a criteria for having blood pressure data on file, and the third group ("GROUP 3") includes 204 candidates that do not satisfy an age requirement criteria. As discussed above, multiple groups are identified to provide the researcher with the ability to expand eligibility beyond only those candidates that match every single criteria.

The second predicted study parameter involves predictions relating to participant-level data presented in interface element 202B. As shown in FIG. 2, the computer system 120 identifies predictions for three participants "Joe," "Susan," and "Dave." The computer system 120 generates these predictions based on evaluating attributes and/or activity patterns for each corresponding participant within the database 122. For example, participants Joe and Susan are predicted to have a high completion score since their participation data in previously conducted studies show that they have successfully completed those studies. In contrast, participant Dave is predicted to have a low completion prediction score since his participant data indicates that he has dropped out of several prior research studies due to complications. The prediction data thereby provides the researcher with historical context when determining whether to select a particular participant to include in a cohort.

The third predicted study parameter involves predictions relating to additional research questions that may be related to the study design criteria specified in the query. As shown in FIG. 2, the computer system 120 predicts three research questions that have a high likelihood of being related to keywords specified in the design criteria. In this example, the computer system 120 uses language processing techniques to determine that the terms "blood cancer," "exercise," and "72+ years" are related to the general concept of exercise-related evaluation related to blood or cancer in elderly individuals. The computer system 120 accesses the historical study data 122B to identify research studies with research questions that are related to this general concept. The first example of a predicted question involves evaluating effects of exercise on chemotherapy treatment efficacy. In this example, the terms "exercise" and "chemotherapy" are identified as being relevant to query keyword "exercise" and "blood cancer." The second example of a predicted question involves evaluating the prevalence of blood cancer amongst individuals older than 70 years old, which is identified as being relevant based on the terms "blood cancer" and "individuals older than 70 years old."

The computer system 120 can use machine learning in a variety of ways. For example, machine learning models to classify individuals with respect to different outcomes. For example, models can be trained to predict, from input about an individual's attributes, whether the individual will really remain engaged in and be retained in the study until completion of the study. Models can be trained based on the examples of profile data in the database 122. Models can be trained to make predictions about a variety of outcomes, such as whether individuals will respond to different types of communication (e.g., email, SMS text messages, cell phone notifications, phone calls, etc.), whether they will answer different surveys or even individual questions, and so on.

The computer system 120 can use machine learning models to predict which of multiple "near miss" (e.g., partially eligible) groups of individuals will best for fill the needs of the study. In other words, the computer system 120 can analyze data for the study (e.g., the study question and or selection criteria) and records of prior studies to determine which selection criteria are most important or are least able to be changed. With this information, the computer system 120 can generate recommendations to relax steady selection criteria in the least disruptive manner for the research being conducted.

Machine learning models can be used to predict which selection criteria are most likely to be improved by individuals. Part of this training can capture the progression of data collection and user profile data changes in the database 122, which can show which attributes are readily changed and which are not. For example, records of responses of users recorded in the database 122 can demonstrate that obtaining a consent indication, answering a survey, or obtaining a blood test can be relatively easy to achieve, and so the models can learn to recommended groups that need these types of items as groups that can be made eligible for a cohort. For example, the models and predictions can be based on progressions of data collection over time for individuals, the computer system 120 can analyze (including training models to predict) which attributes or data collection capabilities are most easily changed. For example, a person's height is not changeable, but weight can be changed. Even so, losing weight can be very difficult, and the database may show that participants rarely lost weight when requested to do so. The computer system 120 may determine, however, that obtaining answers to a survey, or enabling a sleep tracking functionality on a phone or medical device is performed with much greater frequency. Given the information in the database, the computer system 120 can analyze the many types of information to be collected and attributes that may be requested for studies and arrange them in a hierarchy or give them scores according to the likelihood or frequency with which individuals are able to become eligible for those items. Given that user actions depend on many factors and different users respond very differently, an effective approach is to train a model based on the examples of many different individuals having different situations and attributes.

Figure 3:
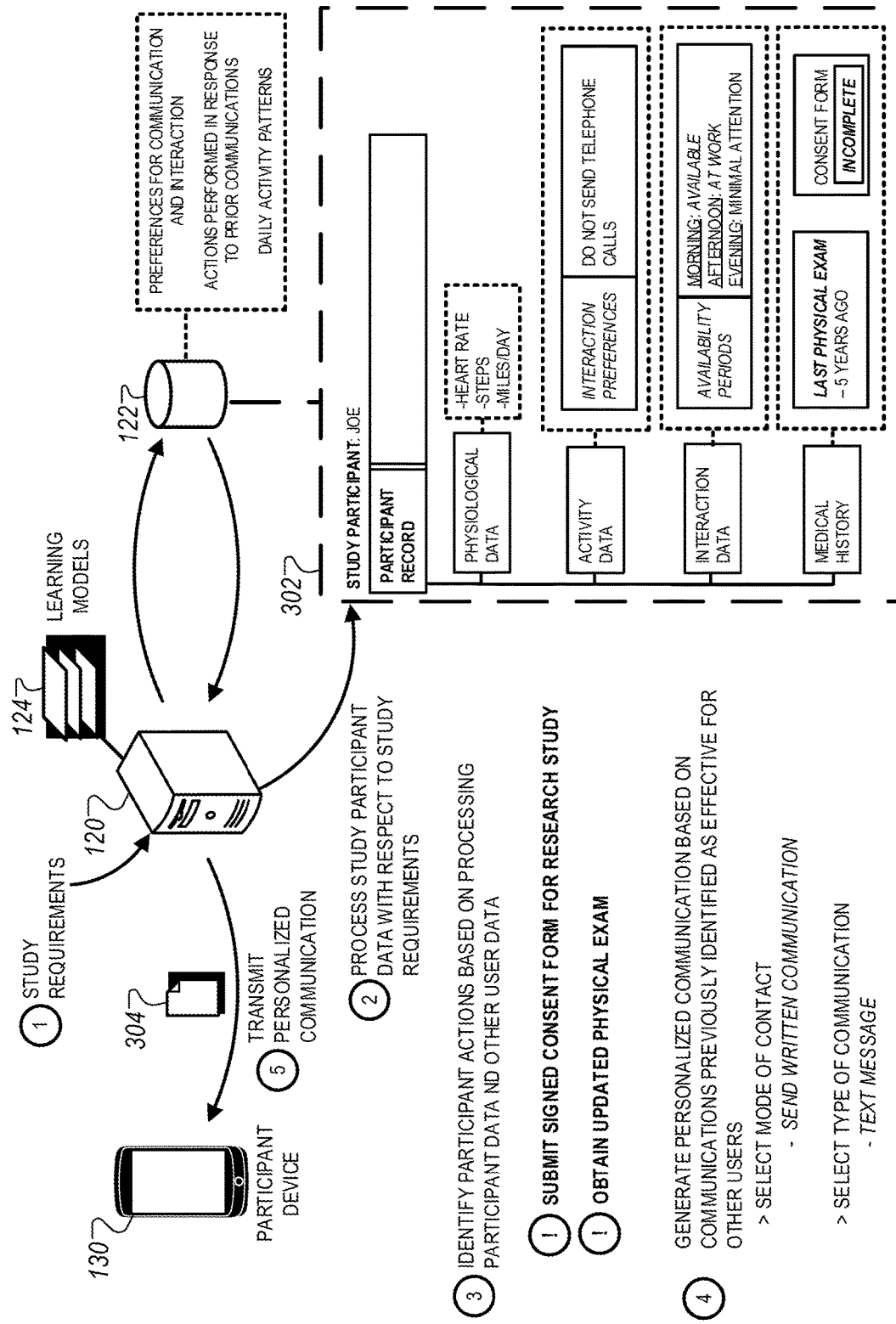
FIG. 3 illustrates an example of a technique for adjusting the management of a research study based on processing participant data.

FIG. 3 illustrates an example of a technique for adjusting the management of a research study based on processing participant data. In this example, the system 100 evaluates data corresponding to a participant enrolled in an ongoing research study. As discussed in detail below, based on this evaluation, the system 100 determines an action required to be performed by the participant to be compliant with the research study, and provides a customized notification to a participant device 130. Using this technique, the system 100 improves a likelihood that a participant will be compliant while participating in the research study by providing notifications that are customized to the specific interaction preferences of the participant.

In the example shown in FIG. 3, the computer system 120 processes a participant record 302 stored in the database 122 to determine whether participant "Joe" is compliant with participant requirements for a research study. In making this determination, the computer system 120 evaluates contents of the participant record 302 to determine whether the participant is required to perform any further actions to be compliant. The contents of the participant record 302 include heart rate data, sleep tracking data, medical history information, and participation data for other research studies for which the participant has previously participated.

The computer system 120 processes each type of data within the participant record 302 with respect to data requirements for the current research study. For example, the computer system 120 parses the participant record 302 to determine that it does not a signed consent form that is required to be signed by all participants of the research study. As another example, the computer system 120 parses medical history information to identify the date of Joe's last physical examination. In this example, the age associated with the identified date is compared to a threshold age specified for valid physical examinations for participants enrolled in the research study.

The computer system 120 identifies actions required to be performed by Joe based on processing the participant record 302. For example, the computer system 120 determines that Joe needs to complete and sign a consent form based on the participant record 302 not including any consent form for the research study. The computer system 120 also determines that Joe needs to have a new physical examination since the date of Joe's last physical examination is not valid for the research study.

The computer system 120 generates a personalized communication 304 based on identifying the actions required to be performed by Joe. In generating the personalized communication 304, the computer system 120 selects a mode of contact that makes the communication most accessible, selects the type of communication that coincides with Joe's preferences for communications, and selects a time to transmit the communication during a time that Joe is available to properly interact with the received communication. For example, the computer system 120 selects a written contact as the mode of contact (as opposed to verbal contact) given Joe's historical activity data indicating that he has previously responded to other text messages but ignored phone calls. The computer system 120 also selects a text message as the type of communication (as opposed to an email or notification message) since Joe's interaction preferences show that he has not acknowledged any prior email communications and explicitly indicated that he does not want to receive any notifications.

Additionally, the computer system 120 selects to send the communication to Joe in the morning (as opposed to the afternoon or evening) based on prior activity data indicating that the morning time is when Joe is available to engage with information. For example, the prior activity data indicates that Joe's attention level is diminished during the afternoon since he is at work and not able to access his phone. Moreover, the computer system 120 does not select the evening time since Joe's historical activity data indicates that he responded to prior messages sent to him during the evening with a diminished attention level (e.g., short text responses, or a small amount of time spent in preparing a response).

The computer system 120 then transmits the personalized communication 304 to the participant device 130 in the manner specified by the customization. Specifically, the computer system 120 sends a text message that includes two action items to be completed at 9 AM. The information accompanying the action items can also be customized based on Joe's preferences. For example, since Joe is a younger individual with an active lifestyle, the computer system 120 determines that he responds more favorably to action challenges, rather than task lists. The personalized communication 304 therefore includes a challenge to submit a consent form and complete a physical examination within 5 days.

The computer system 120 can automatically generate and send communications to prompt individuals to remedy issues that prevent their full eligibility for inclusion (e.g., initial selection to be included) in a cohort. This process can include the computer system 120 predicting which individuals are most likely to be able to reach eligibility so it can selectively contact individuals identified as most likely to respond and achieve eligibility. The computer system 120 can analyze the gaps between the attributes of individuals and the requirements of the cohort selection criteria, and then generate and carry out a campaign of personalized interactions with selected individuals to close the eligibility gaps and bring the users into eligibility to be added to the cohort.

The computer system 120 may select individuals to bring into eligibility based on the closeness of the attributes in their profiles in the database 122 to the selection criteria. In other words, the computer system 120 can use the number and type of selection criteria that individuals lack to determine if enhancement of the individual's eligibility should be attempted. In some cases, the computer system may simply select identified sets of candidates that lack the fewest selection criteria. In other cases, the computer system 120 may select individuals based on a variety factors and across different groups of cohort eligibility, for example, based on the responsiveness of each individual to communications and taking actions to complete their data profile in the database 122.

Moreover, using the examples of user attributes and other characteristics in the database 122, the computer system 120 can predict which types of users are most likely to perform which types of actions. For example younger users might be more likely to download and install an app on their phones, while older individuals who have more regular doctor appointments may be more likely to provide or obtain blood test information. The computer system 120 can use these predictions in determining which groups of users to attempt to bring into eligibility with respect to selection criteria, and even to select which individuals within a group to contact.

The communications to prompt individuals to become eligible can be personalized for the set of individuals in the database 122, or even for the groups of individuals that meet at least some of the study selection criteria. In other words, the predictions can be based on observed behavior for users in the actual pool of candidates for the study and/or based on users determined to have at least a minimum level of similarity with users in the pool of candidates being considered for the study. In this analysis, the computer system 120 can take into account how individuals have responded to requests or other communications from the computer system 120. For example, the computer system 120 can analyze which types of changes people make when requested by the system 120.

The computer system 120 can use the examples from the database 122, or machine learning models trained on this data, to select the content of messages and manner of providing the messages. For example, even when requesting the same information, such as answers to a survey or results of a blood test, the computer system 120 can select from different communication channels e.g. email, text message, paper mail, etc. The content of the message, the wording of the message, the format of the message, accompanying media or explanation, and so on can be tailored for each individual.

Another use of the computer system 120 is to perform automated selection of forms to send to individuals to evaluate whether an individual meets exclusion criteria that would prevent participation in a study. Common exclusion criteria include pregnancy and mental health conditions. Just as the computer system 120 evaluates inclusion criteria for a cohort, the computer system 120 can store and evaluate exclusion criteria to determine if an individual should be excluded. The computer system 120 can generate communications (e.g., questionnaires, surveys, etc.) to obtain data to quickly determine whether an individual satisfied inclusion criteria. Targeted, customized communications can be used to request information that will fill the gaps between what is known about an individual and what is needed to satisfy the selection criteria. The computer system 120 can similarly generate communications to request information to evaluate whether individuals have factors that would satisfy exclusion criteria.

Figure 4:
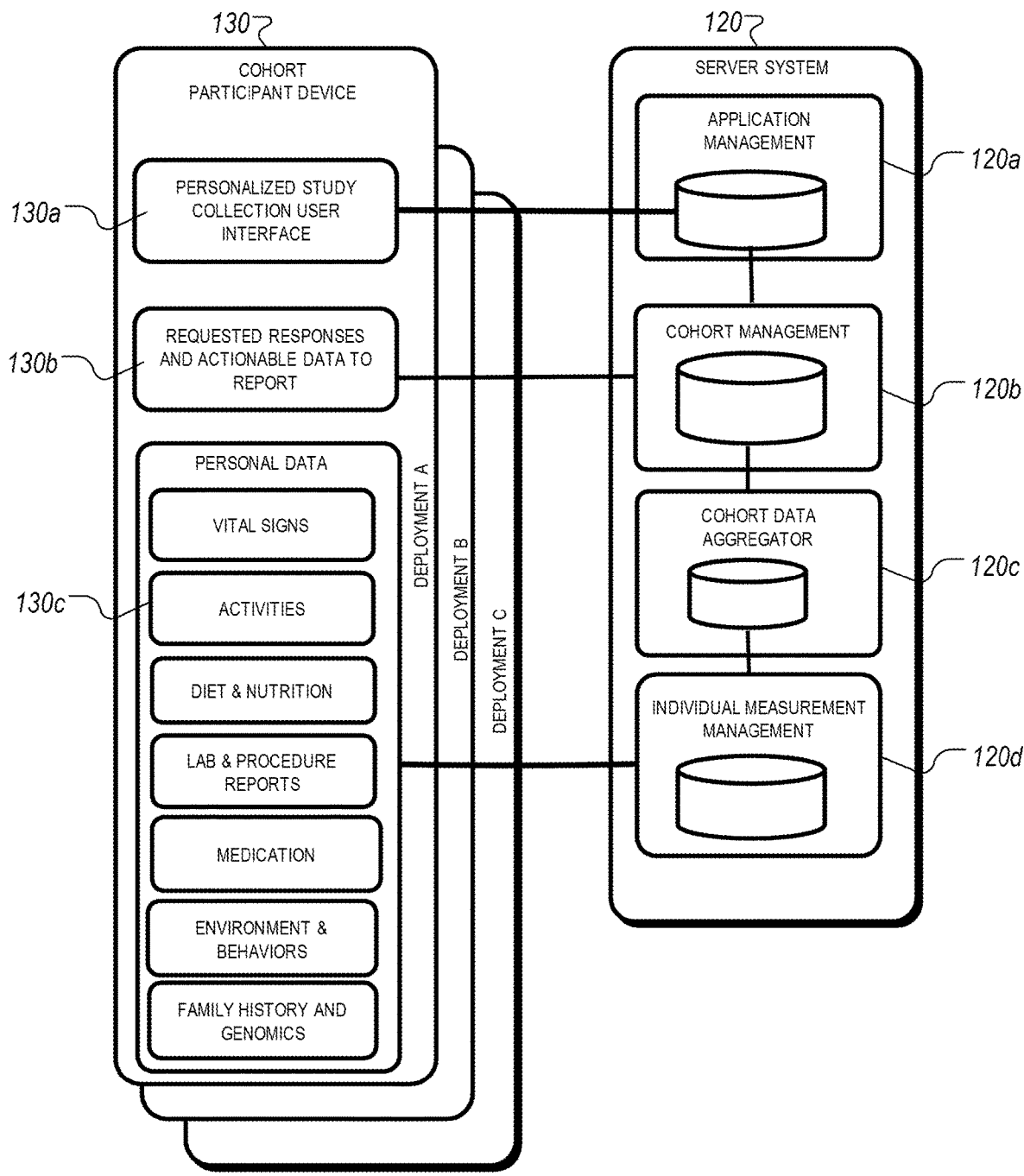
FIG. 4 illustrates an example of software components of a participant device and a server system that may be included in system depicted in FIG. 1.

FIG. 4 illustrates an example of software components of a computer system 120 and a participant device 130 that may be included in system 100 depicted in FIG. 1. In general, data communications between participant device 130 and computer system 120 permits the system 100 to perform various evaluation techniques related to a research study, such as classifying participants for recommendations related to cohort selection (as described in FIG. 6A), aggregating participant data to predict study parameters for a new research study (as described in FIG. 6B), and evaluating a participant's detected activity patterns to determine compliance behaviors (as described in FIG. 6C).

As shown in FIG. 4, the participant device 130 includes software components 130a and 130b, and stores data 130c. Component 130a is a personalized study collection user interface that allows a participant to receive communications on a given or upcoming study or sub-study. For example, the component 130a can be an interface of an application through which the participant enrolls in new research studies, accesses participant data for an enrolled studies, among others.

Component 130b allows requested responses and actionable data to be reported to the computer system 120. For example, if data is required for eligibility, a participant may receive information through the component 130b on the data they need to do to contribute and be selected for a research study (or research sub-study). The participant may interact with the component 130b to share data directly, or through varying connected devices or applications that may be housing the participant data, and may increase eligibility due to gaps in information that the server detects is required for eligibility.

Data 130c includes various types of information specific to a participant that is gathered from available data that is, for instance, accessible through the participant device 130, stored on the participant device 130, connected to the participant device 130 (e.g., a data monitoring service), or enabled by the participant device 130 for sharing (e.g., through a companion wearable device worn by the participant). Data 130c includes longitudinal data that specifies data across history of the participant that. For example, longitudinal data can be generated since inception of a particular device or application depending on longevity of the data. The data may also provide new measures of the participant's present state, and continue to provide data submitted by the participant as he/she continues to share data beyond on a re-occurring basis (e.g., data submitted by the participant as he/she participates in an enrolled research study).

Data 130c includes vital signs that specify information related to health measures. The vital signs can be generated as an outcome of blood samples, ether obtained invasively through a blood draw or noninvasively using specialized equipment. Other examples of vital signs include measures and samples can provide heart rate, resting heart rate, heart rate variability, blood oxygen level, blood glucose level, blood pressure, spirometry, ECG/EKG data, EEG data, thermometer data, stethoscope data, continuous blood pressure monitoring data, continuous glucose monitoring data, among others.

Data 130c can also specify activities in the form of events that the participant's body exhibits based on events throughout the day (e.g., movement related to exercise, generalized steps, distance traveled, or the body at rest). As an example, the events can be monitored with regards to sleep duration, sleep quality and sleep stages, along with human performance measures like vo$_2$ max, or cognitive measures related to meditation or mind excitation, studying, recall or recitation.

Other examples of data 130c include diet and nutrition related to the daily ingestion of micronutrients, such as fat, carbohydrates, sugar, proteins, and nutrients (e.g., sodium), vitamins (e.g., Vitamin A or D), and the impact they have through the participants weight, caloric intake, active energy, resting energy, and risks associated with production such as fried versus grilled and specific ingredients like gluten, enriched flour, corn syrup, hydrogenated vegetable oils like cottonseed oil, and table salt. Lab and procedure reports can also be related to electronic health record data and contain visit-based information with a health care individuals, team or payer-related details and can include allergy information, blood sample/organ biopsies as lab data, surgical procedures, visit, prescriptions and claims.

Medication data included in the data 130c can include actual usage of prescriptions, over-the-counter medicines, or holistic and illegal substances. Examples of prescriptions include general medications (e.g., pain medications), disease-related medications (e.g., diabetes-related basal/bolus insulin), or circumstance-related medications (e.g., medications used to treat pregnancy related high blood pressure related management. Over-the-counter could include cold medications, allergy, or pain low-dose medications.

Other data included in the data 130c specify environment and behaviors, such as movement and changes around the body based on the action/interactions from a lifestyle perspective For example, an individual exposed air quality in the home is dependent on the time spent at home, along with humidity, barometric pressure changes, altitude changes, loudness, and toxicities. Family history and genomics data can specify risks that may be genetically linked to the individual predisposition or current disposition such as the participant's family history of smoking, eyesight, heritage and family tree, where they lived primarily during life, any chronic illness, along with the participants and families Genomics attributes, SNPs.

The computer system 120 includes components 120a, 120b, 120c, and 120d. Component 120a references to application management, which specifies the configurations and data messaging foundational application utilities that may be used to communicate between the computer system 120 and the participant device 130. Component 120b enables cohort campaign management, including data insight dashboards presented to a researcher, configuration of participant data related to a research study, and any recommendations generated based on eligibility (as shown in FIG. 1).

Component 120c is a data aggregator that specifies the cohort as being managed data as insights derived from the participant or individual data collected through the individual measurement management. This component 120c can derives insights and recommendations for eligibility when queried by component 120b.

Component 120d enables individual measurement management. For instance, component 120d specifies individual data storage for each participant across their sources and relevant configurations for enrolled studies and engagements. The component 120d provides access to the component 120c along with transparency to the component 120b with respect to each individual participant.

Figure 5:
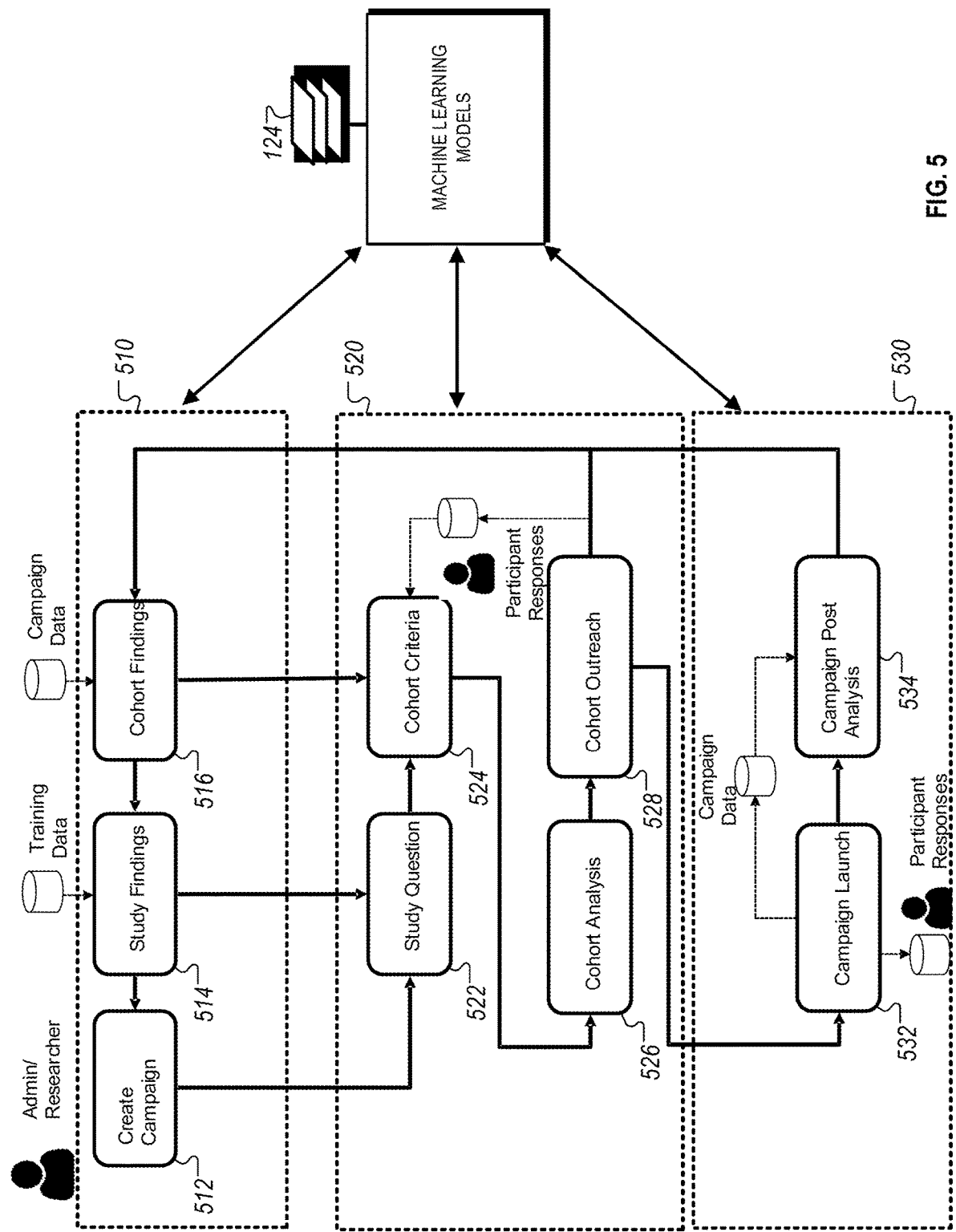
FIG. 5 illustrates examples of techniques for applying machine learning to generate predictions during different stages of a research study.

FIG. 5 illustrates examples of techniques for applying machine learning to generate predictions during different stages of a research study. In this example, machine learning models 124 can be applied at three stages of a research study.

At step 510, the machine learning models 124 are applied to either improve study design for a new research study to be conducted, or evaluate data for a recently concluded research study, as described in reference to FIGS. 2A and 2B. For example, for a new research study, a researcher initially creates a campaign at step 512. During this process, the machine learning models 124 can be applied to historical study data (e.g., data associated with completed research studies) to identify patterns and/or trends that may be useful to the researcher during the study design process. For example, as shown in FIG. 2, the researcher may be presented with automated recommendations for potential study questions based on terms identified in a research query.

For a recently concluded research study, campaign data collected during stage 530 (discussed below) is evaluated at step 516 to generate study findings at step 514. The evaluation can involve using heuristics, natural language processing, and/or other processing techniques to develop results related to the study question generated in step 522. For example, the research question can be determining whether participants experience anxiety after undergoing a certain type of surgical procedure. In this example, the machine learning models 124 can evaluate patient survey responses identified as being received after receiving the surgical procedure for the occurrence of specified keywords that are known to be associated with anxiety.

At step 520, the machine learning models 124 are applied to predict eligibility of candidates in the cohort selection process, as described in reference to FIG. 1. For example, a researcher initially designs a new research study by generating a study question (step 522), and developing a set of cohort selection criteria (step 524). A potential cohort is evaluated at step 526 by identifying desirable attributes of participants that are necessary and/or helpful to evaluate the question for the study (e.g., diagnosis of a medical condition under evaluation, a necessary diagnostic test, etc.). Once possible candidates are identified at step 528, the machine learning models 124 are applied to determine eligibility with respect to cohort criteria prior to outreach at step 527. The machine learning models 124 can be evaluated to determine whether all cohort selection criteria are satisfied (e.g., a participant is fully eligible), and if not, an eligibility level of the candidates or group of candidates (e.g., specific numbers of cohort selection criteria that are or are not met). This data can also be used to provide the researcher with recommendations, such as modifying cohort selection criteria to improve eligibility among candidates. This can include identifying which items of the candidate selection criteria are least likely to be satisfied and recommending that those constraints be removed or relaxed.

In some cases, recommendations of specific criteria to modify can be determined based on the groups of candidates. For example, the computer system 120 can evaluate the sets of candidates that lack different aspects of the cohort selection criteria. The computer system 120 can recommend specific changes to the criteria that would bring in one or more of the groups of candidates that did not fully meet the original criteria. Similarly, the computer system 120 can recommend changes that would cause the criteria to encompass part, but not all, of one or more groups that did not fully meet the original criteria.

As an additional example of recommendations, the computer system 120 can identify other actions to take to increase the number of subjects that satisfy the original criteria. For example, the computer system 120 can evaluate, for each criterion, the relative difficulty of a subject moving from non-eligibility to eligibility. Some items, such as whether a blood test result is on file, are relatively simple to change. Other items, such as a person's height or prior medical history may not be changeable at all. Various other items have more intermediate levels of difficulty to change. With this information, the computer system 120 can select one or more of the cohort selection criteria that subjects in the database are most likely able to change, taking into account the individual histories and attributes of those subjects. The computer system 120 can then provide a recommendation and user interface controls to initiate communications to candidates to make the changes needed to comply with the original criteria (e.g., have a blood test taken, complete a survey, obtain a needed medical device, etc.)

At step 530, the machine learning models 124 are applied to predict and/or evaluate the impact of study design parameters on study outcome, as described in reference to FIGS. 2A and 2B. As an example, a learning model trained to process historical actions of enrolled participants can be employed to identify a likelihood of an enrolled patient performing a non-compliant behavior that impacts study outcome (e.g., not submitting post-treatment feedback according a monitoring schedule) given the survey procedure for a study. In this example, if a certain survey technique has a high likelihood of resulting in non-compliant behavior, the system can either identify a new survey technique that is likely to produce compliant behavior (e.g., a survey that uses a simpler format that is more likely to perceived by participants as being easier to complete) or a change to the monitoring frequency (to reduce the burden imposed on participants and thereby increase the likelihood of compliance).

Once a cohort is confirmed, a campaign is launched at step 532. This can involve the researcher initiating the research study and collecting participant responses (e.g., survey responses submitted by participants). As discussed above, participant response data collected at step 532 can be processed using the machine learning models 124 to identify whether any study design parameters should be adjusted to improve study outcome. This occurs iteratively as the research study is occurring so that the researcher can implement any changes before the conclusion of the research study. In this way, if a research study is initially found to be poorly designed (e.g., high likelihood of producing non-compliant participant behaviors, or low likelihood of collecting statistically significant scientific data), then the researcher can receive automated recommendations prior to completing the research study (and thereby wasting associated time and resources).

At step 534, once a research study is completed, the machine learning models 124 can be used to process campaign data to perform post-study analysis. For example, natural language processing can be used to identify those participant responses received are likely to produce positive study outcomes and identify other participant responses where a participant neglected to properly follow survey instructions (which can then be used to improve data quality).

Figure 6:
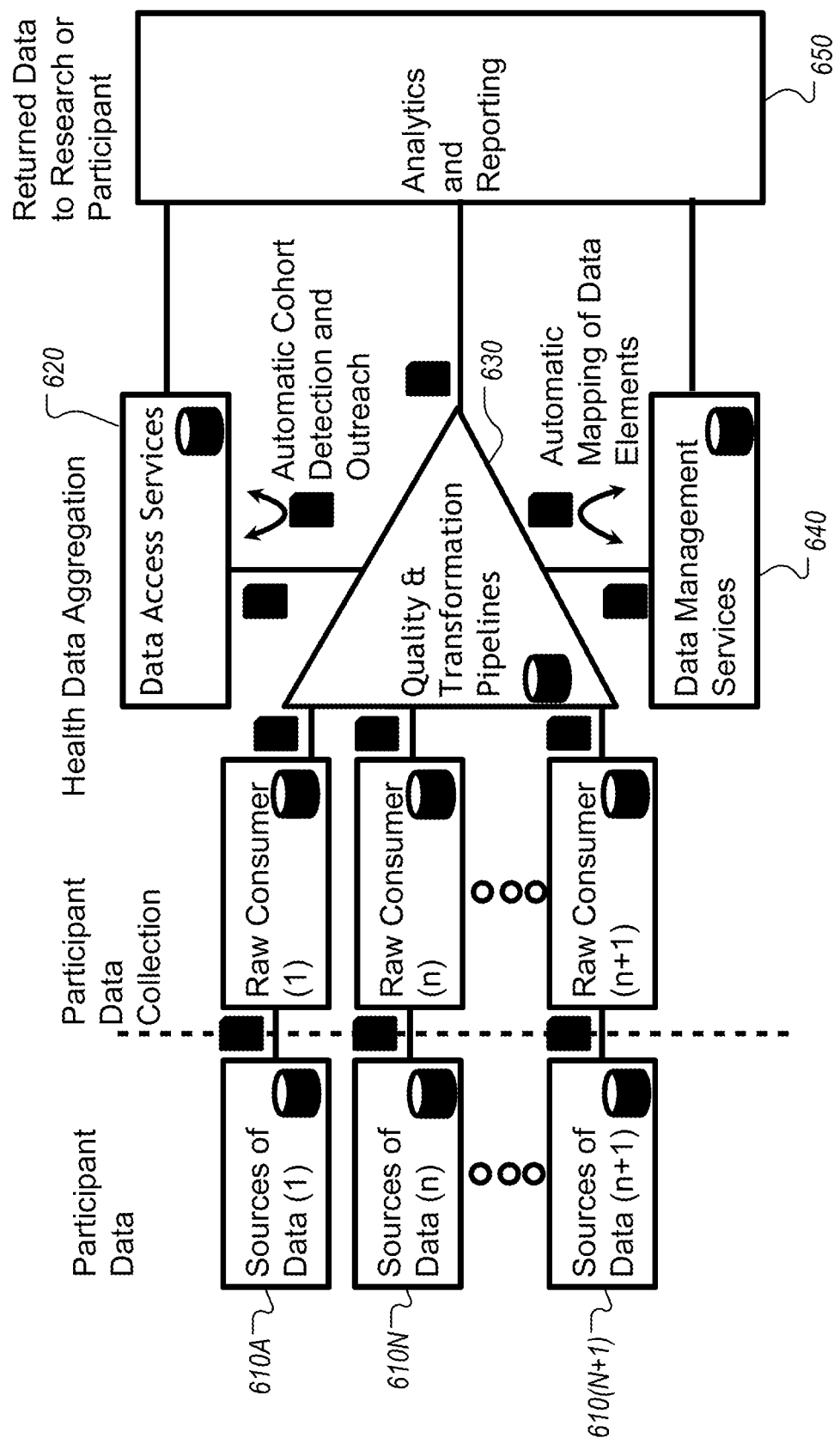
FIG. 6 illustrates an example of a data aggregation process for automated cohort selection and management.

FIG. 6 illustrates an example of a data aggregation process for automated cohort selection and management. In the example, participant data is initially obtained from a set of data sources 610A, 610N, 610(N+1). The participant data includes information residing with the participant, such as data collected from wearable devices, electronic health record data, self-reported data (e.g., survey responses), genomics data, observed data, among other types of data related to participant lifestyle, health, environment and behaviors.

Each data source is collected through varying methods, transports and languages. For example, direct-to-device data refers to data collected by the consumer directly from a data source, for instance, by connecting to a device and receiving data as its being recorded (e.g. passive sensing, Bluetooth, Wi-Fi direct), or through an interface available to the participant to interact with and respond (e.g. self-reported data).

As another example, direct-to-app data refers to data that has an integration layer between data collected by a manufacturer of the data source and an application through which the data is accessed (e.g. electronic health record data, secondary applications that source data through application programming interfaces (APIs), cloud-based data services that access manufacturer data directly or through use of storage APIs).

Data can also be obtained directly (e.g., based on submissions by a participant) or indirectly through various data access services that provide data aggregation services. For instance, participant data can be connected through multiple storage utilities where the originating source of truth may be at risk due to transformation through multiple connections. Additionally, import-related transformation techniques can be used to permit manual transfer of participant data. For instance, a participant can use the transformation techniques to bring a file into the system directly when they are the owner of the file, even though the file may have been exported by another data service.

Participant data collected through different pipelines can be aggregated for can for management and analysis. Data quality mechanisms (e.g., data access services 620, quality and transformation pipelines 630, and data management services 640) can be used to enable information exchange, and manage gaps related to data collected for the purpose of management, findings, insights and cohort detection and outreach.

Once participant data is processed and evaluated, reports 650 can be generated to be provided for output to a researcher or participant. The reports 650 can include various types of analyzed data, as discussed throughout this specification. For example, the reports can include downstream to return of results (ROR), return of information (ROI) and insights, and return of value (ROV).

Figure 7:
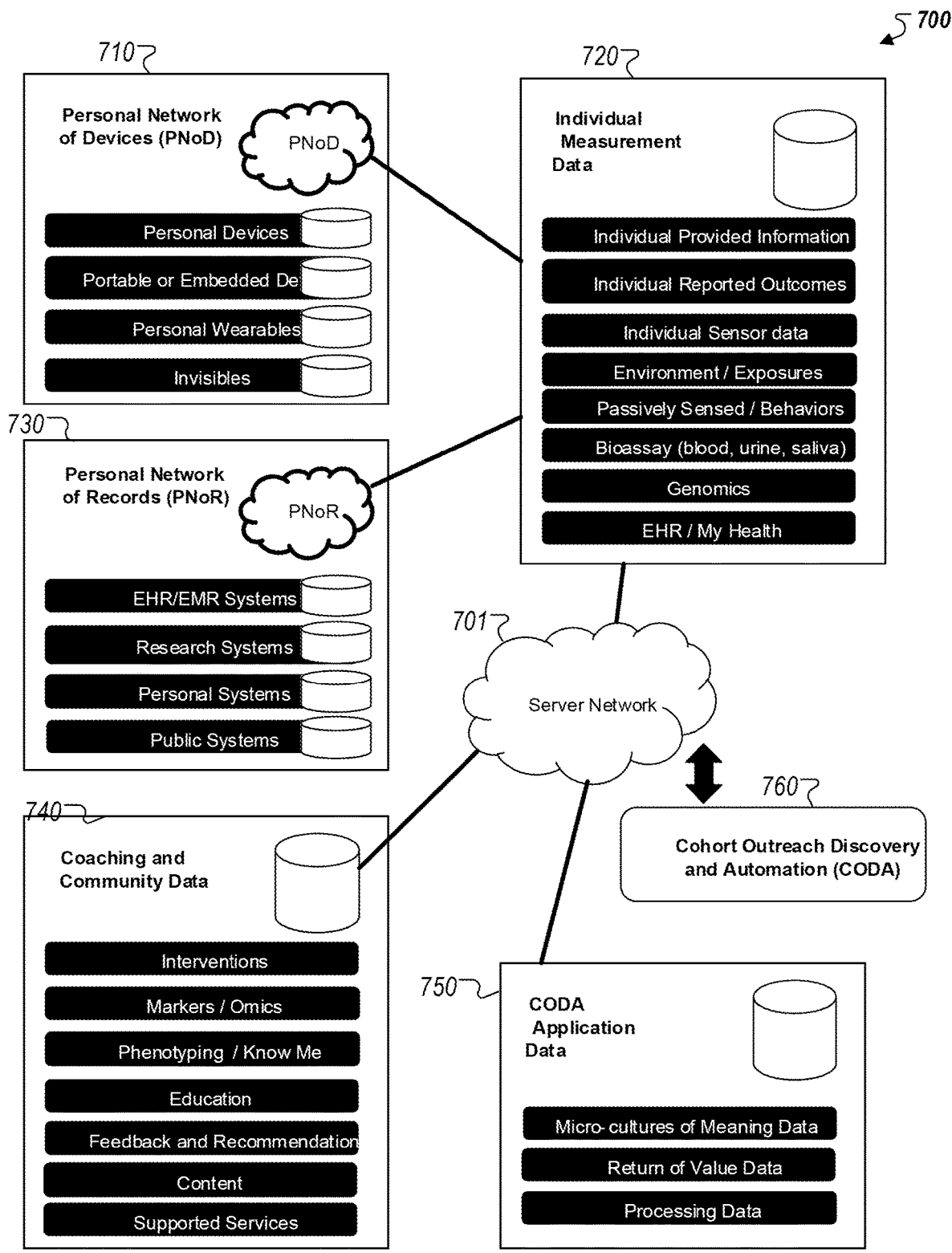
FIG. 7 illustrates an example of a data network representing input, storage, and sharing of different processes related to cohort outreach discovery and automation.

FIG. 7 illustrates an example of a data network 700 representing input, storage, and sharing of different processes related to cohort outreach discovery and automation. As shown, the data network 700 includes personal network of devices (PNoD) 710, individual measurement data 720, personal network of records (PNoR) 730, coaching and community data 740, application data 750, and a cohort outreach discovery and automation (CODA) system 760. As described throughout, the CODA system 760 accesses the individual measurement data 720, the coaching and community data 740, and the application data 750 through a server network 701. In some instances, the CODA system 760 can represent the system 100 depicted in FIG. 1.

The individual measurement data 720 includes various types of information about participants of a campaign managed by the CODA system 760. As examples, the individual measurement data 720 includes information provided by the individual, reported outcomes for the individual, sensor data, environmental or exposure data, passively sensed behavioral data, bioassay data (e.g., blood tests, urine tests, saliva tests), genomics data, or EHR data. The individual measurement data 720 is collected primarily from the two data sources shown in FIG. 7. The PNoD 710 includes devices that are managed by a participant, such as personal devices, portable or embedded devices, wearable devices, among other types of devices that are accessible by the participant. The PNoR 730 includes various devices and/or systems that store health data of the participant, such as EHR systems, research systems, personal systems, and public systems.

The coaching and community data 740 and CODA application data 750 represent other types of data sources that can be used in eligibility determinations and/or outcome determinations developed by the CODA system 760. As examples, the coaching and community data 740 can specify interventions (e.g., health interventions), marker data (e.g., genomics data), phenotyping data, education information, feedback and/or recommendations provided to a participant, content accessed by a participant. The CODA application data 750 can include micro-culture data, value data, and processing data.

In the example shown in FIG. 7, machine learning is utilized to automatically identify the appropriate participants for each study to be conducted, and determine statistically relevant scoring of collected participants data described throughout this specification. The scoring can be used for various eligibility determinations, such as eligibility for a cohort to be defined, eligibility for a new study to be conducted, eligibility for a health campaign. Additionally, the scoring can be used to automatically measure outcomes, such as the likelihood of a patient successfully completing a study, the likelihood of a patient exhibiting a certain type of behavioral pattern (e.g., using a mobile device to interact with patient surveys, compliance with specified requirements with a study, etc.).

The machine learning models employed in eligibility determinations and outcome measurements can be trained using survey questions designed by researchers that create studies. Once trained, the machine learning models can be employed to derive additional questions based on the training questions and patterns recognized in participant data collected through the data network 700. For example, if participant data indicates a high percentage of survey responses related to exercise-related stress, then the machine learning models can derive new survey questions that focus on identifying user lifestyles that tend to produce exercise-related stress. As another example, if participant data indicates that a large number of participants in an insomnia study that are identified to have high cholesterol, then a new research question may be derived to evaluate the effects of high cholesterol on insomnia. In this way, the machine learning models can use training data (e.g., research questions and/or research questions designed by researchers) and patterns within collected data to develop new questions for investigation by the researchers.

In some implementations, the data network 700 can include multiple machine learning models based on the inputs and feedback provided through the individual measurement data 720, coaching and community data 740, and CODA application data 750. For example, unsupervised learning and random forest models can be employed to provide advantages in reducing input preparation. This technique can provide recommendations and predictors to participants, researchers, and coaches based on where the participants are most likely to succeed or have the highest risk in terms of setbacks. Public community data specified in the coaching and community data 740 can also be used for genomics to identify gene traits along with standard human performance training test. In such instances, the CODA system 760 can use additional training data and perform a more supervised operation in terms of deviations and predictive trends.

Figure 8:
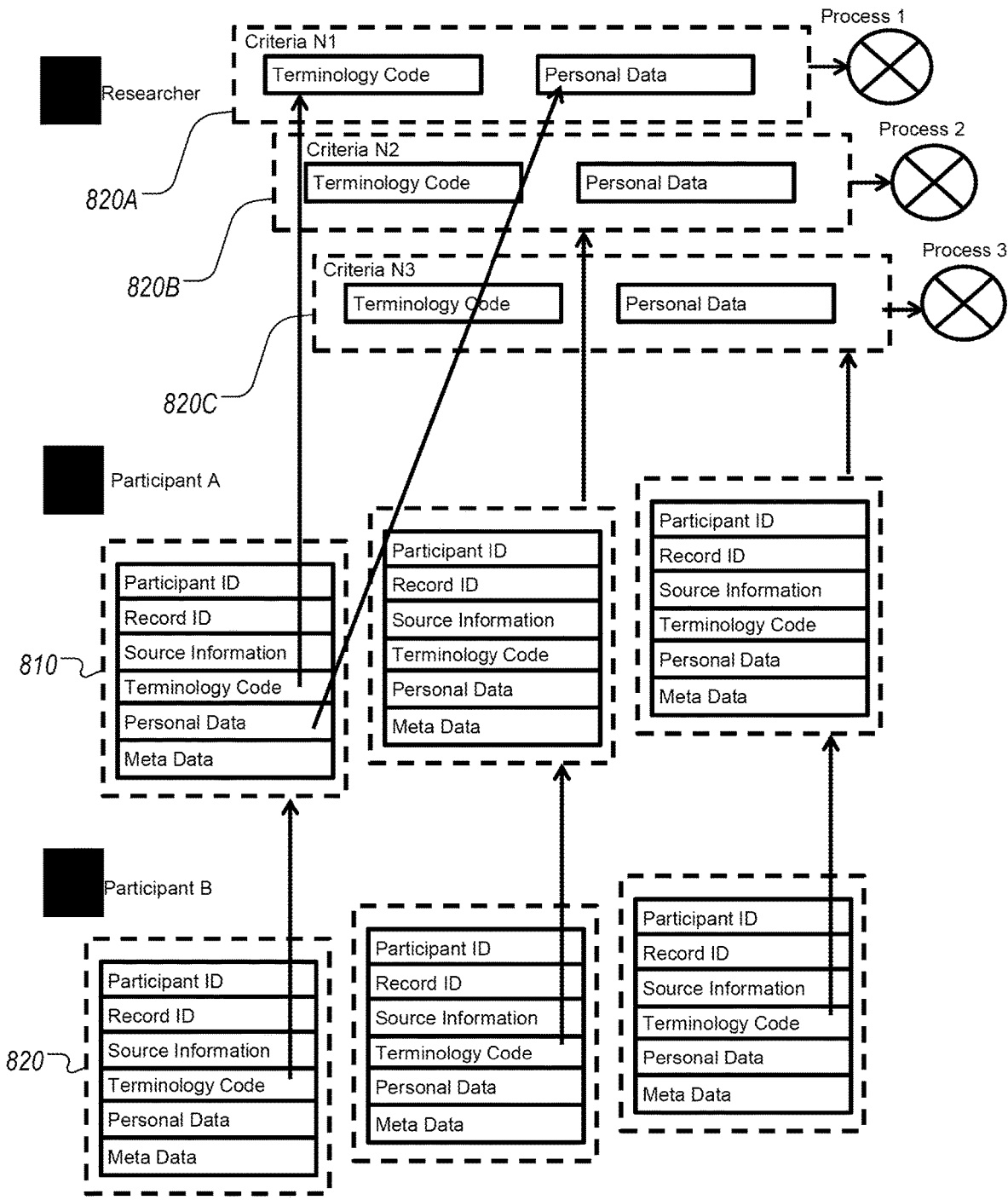
FIG. 8 illustrates examples of participant file scoring for campaign management.

FIG. 8 illustrates examples of participant file scoring technique for campaign management. As shown, the participant file scoring technique generally involves managing data requests to participants and campaign engagement through a participant file that is managed both for distribution by a server (e.g., the computer system 120), and for local requests by a researcher device (e.g., the researcher device 110) for optimized data exchange.

In the example depicted in FIG. 8, a processing mechanism of comparison, relevancy scoring, and eligibility determination for participant files 810 and 820 are updated for two participants A and B, respectively. In this example, a researcher creates criteria from the eligibility needs of a particular research question. Each criterion is saved as an array of data. Arrays 820A, 820B, and 820C include a terminology code and corresponding data (e.g. personal data). The arrays 820A-820C enable comparison of data for eligibility determinations. For example, if the personal data within file 810 indicates that the participant is a smoker, then the system can determine that the participant is not eligible for cohort with a criterion that participants be non-smokers. In some instances, comparisons may yield non-binary determinations, such as a likelihood that the patient is likely to exhibit a certain behavioral pattern that tends to favor or disfavor eligibility. For example, if a criterion specifies a participant frequently use a mobile device to access content when participating in a study, then the candidate participant's likelihood of using a mobile device may favor eligibility (e.g., highly likely to use a mobile device) or disfavor eligibility (e.g., less likely to use a mobile device).

Additionally, the arrays 820A-820C allow the ability to determine and/or manage how many participants match a subset of criteria. For example, forty percent of set of candidates can be identified to satisfy a subset of criteria associated with medical history. Additionally, terminology lookup within the arrays 820A-820C can be used, for example, to compute rank difficulty in acquiring data, determine whether new data will impact previously collected data, determine if the data compared was outside of specified limits, and provide information on whether data is required or can be excluded from eligible candidates.

The metadata and source information included within files 810 and 820 can also be utilized to fill gaps without requesting additional data. For example, if information related to a specific measure is available in another format that can be transposed through laboratory notes or terminology, this information can be recaptured based on conversion factors entered by the participants (e.g., translating steps into distance, converting systolic and diastolic blood pressure measurements into a normalized mean arterial pressure, etc.).

Figure 9A:
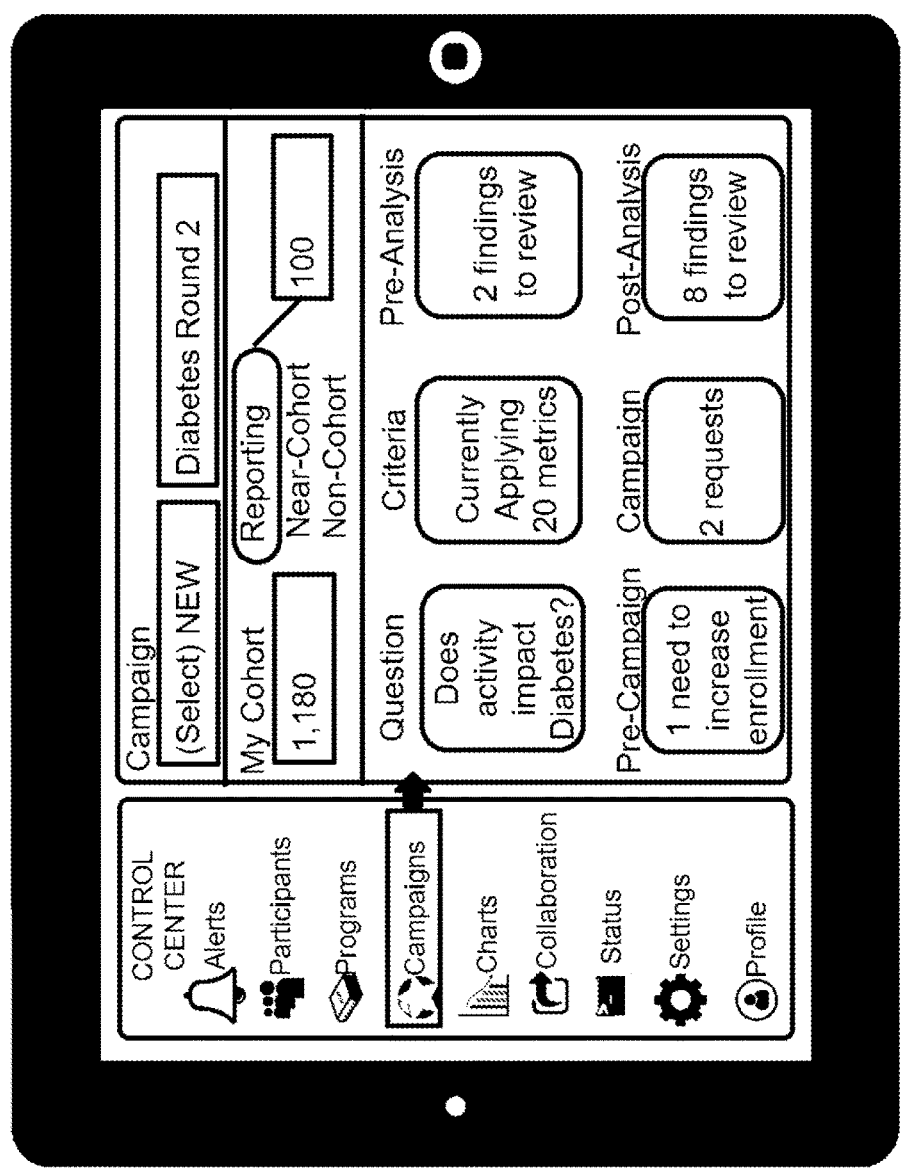
FIGS. 9A and 9B illustrate examples of interfaces for designing survey questions for a new campaign.
Figure 9B:
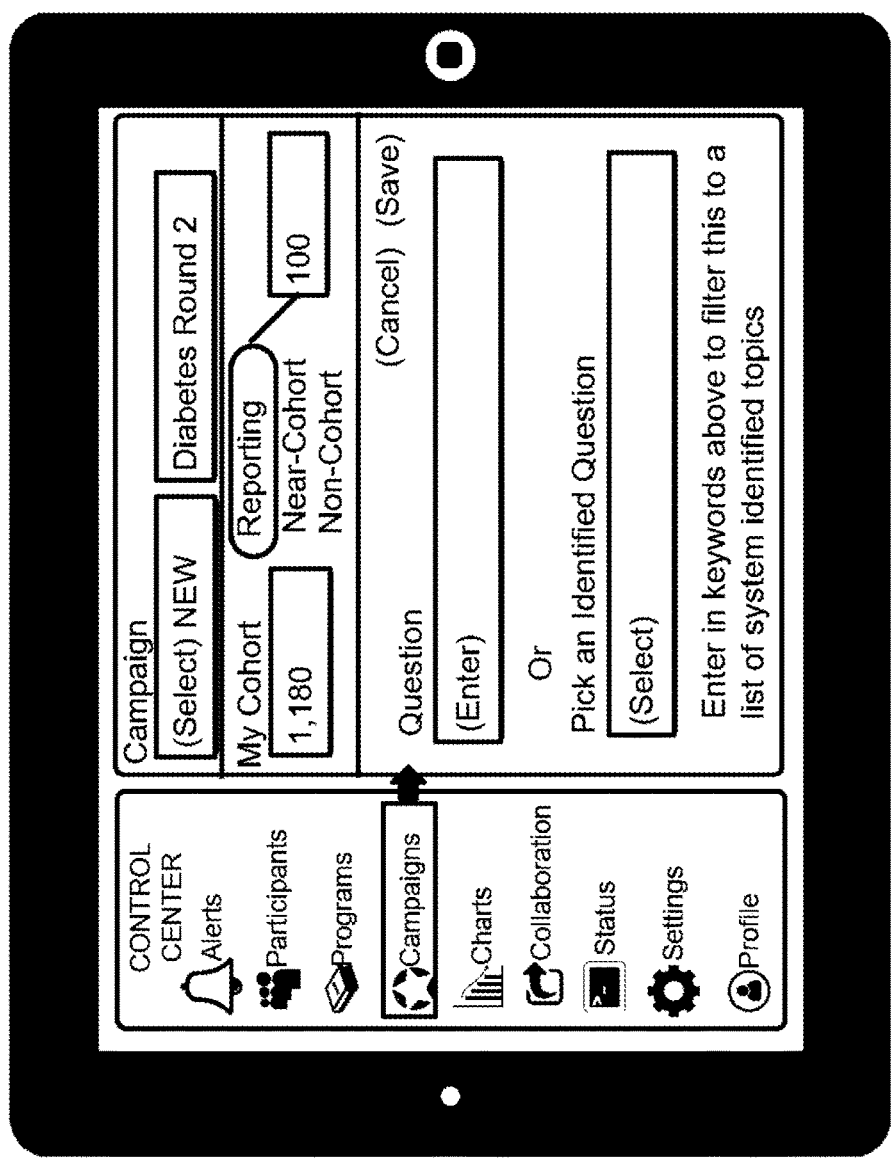

FIGS. 9A and 9B illustrate examples of interfaces 900A and 900B for designing survey questions for a new campaign. The interfaces 900A and 900B can be presented through an application (e.g., the study management application depicted in FIG. 1) through which a research can perform various types of operations related to program management. In some instances, the application can be associated with a companion application is distributed to participants and enables generalized engagement in relation to studies and sub-studies for observation and collection of personal data. For example, participants can use the companion application to access and complete surveys that are designed by a researcher through the study management application. As another example, participants can use the companion application to collect biometric data (e.g., heart rate, exertion, step count, etc.) related to an ongoing research study.

Referring initially to FIG. 9A, an interface 900A that can be used by a researcher to create and manage a campaign is depicted. During campaign creation, the researcher is able to select or specify a new campaign (e.g., a campaign related to studying diabetes). During the new campaign creation process, the interface 900A enables workflow processes corresponding to launching a campaign, such as specifying a question, monitoring criteria, pre-analysis review, pre-campaign review, campaign roll-out operations, and post-analysis review.

In the example shown in FIG. 9A, interface 900A can be used by a research to create a new campaign for studying individuals with diabetes. In this example, 1,180 participants are selected to be a part of the cohort, of which 100 participants are identified as near-cohort (e.g., satisfying only a subset of selection criteria) or non-cohort (e.g., not satisfying key selection criteria). The researcher specifies a research question relating to how a given activity impacts diabetes and identifies twenty metrics to be monitored and evaluated.

Referring now to FIG. 9B, an interface 900B that can be used by a researcher during a question identification is depicted. In this example, a researcher can enter a research question, a partial research question, or a keyword that helps them identify a set of system-generated questions (e.g., questions identified by the system as being relevant based on applying machine learning models to identify patterns within participant data). For example, the researcher can insert a keyword "heart condition," and in response, the system can generate automated research questions that relate to heart disease and diabetes, such as evaluating the effects of diabetes on resting heart rate, or the effects of diabetes on elevated blood pressure during exercise activity. In this example, the automated questions can be generated based on accessing participant data of the 1,180 participants potentially included in the cohort, and then identifying patterns, trends, or other data indicators that relate to the keyword "heart condition." For instance, the questions related to heart rate can be identified as being relevant based on 85% of the 1,180 having heart rate data included in participant data.

In some instances, the researcher can specify criteria related to questioning to narrow the scope of automated questions generated by the system. For example, the researcher can specify an age range of participant data, a global region from which participant data is collected, and a behavioral pattern specified in the participant data (e.g., history of consuming fast food). In this example, the criteria is used to filter the participant data that is used by the system to generate automated questions.

Figure 10A:
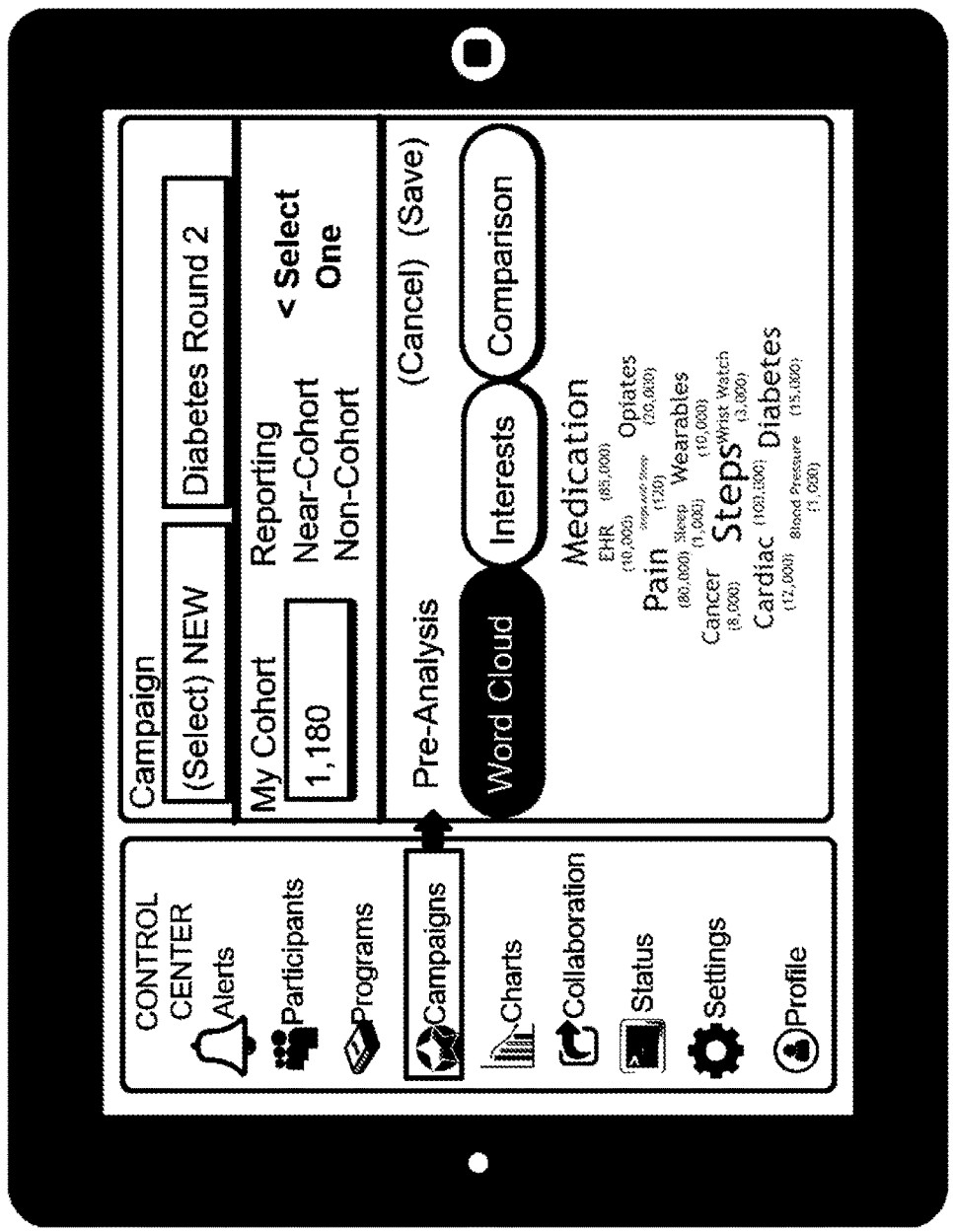
FIGS. 10A-10C illustrate examples of interfaces for cohort outreach and analysis for an existing campaign.
Figure 10B:
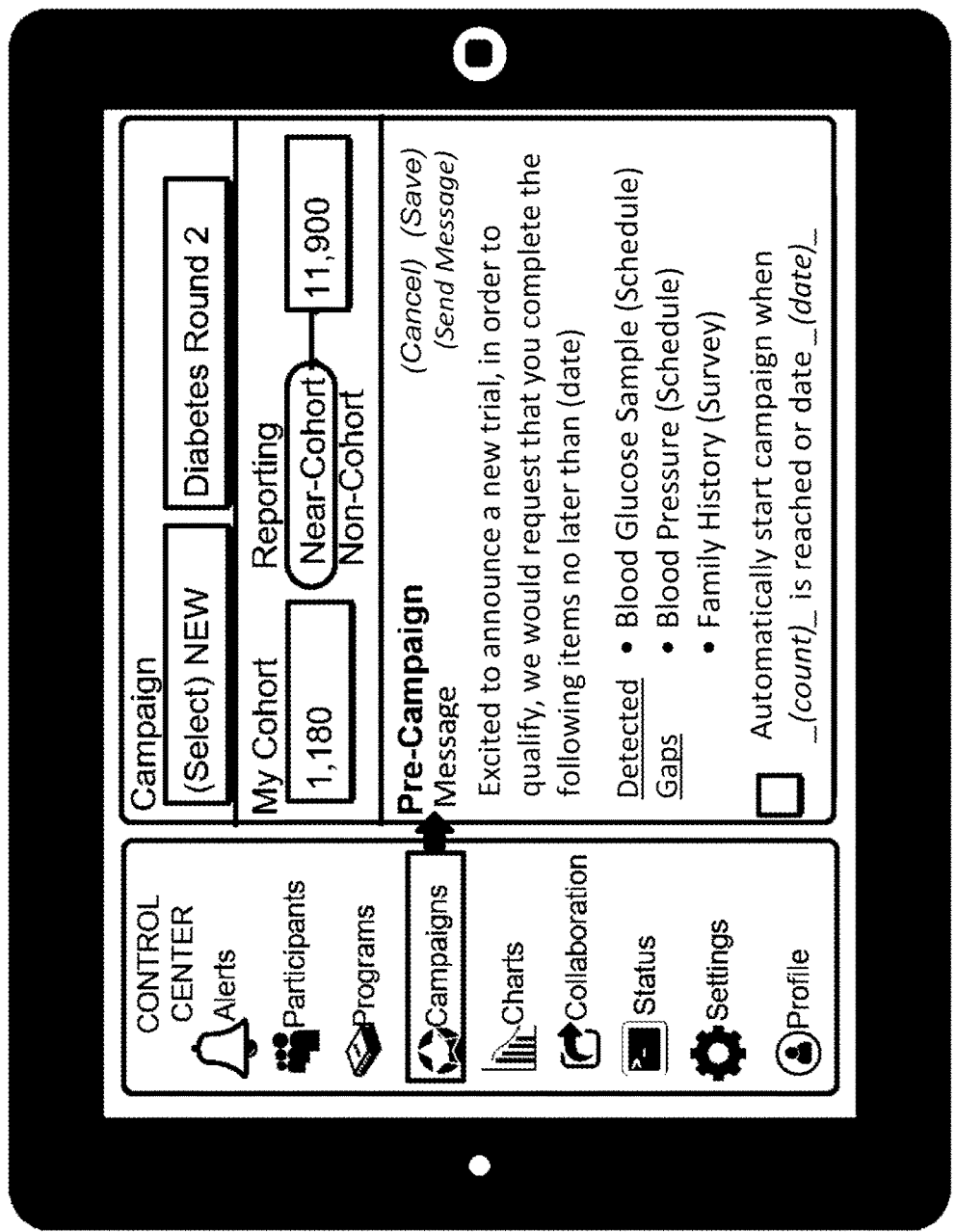
Figure 10C:
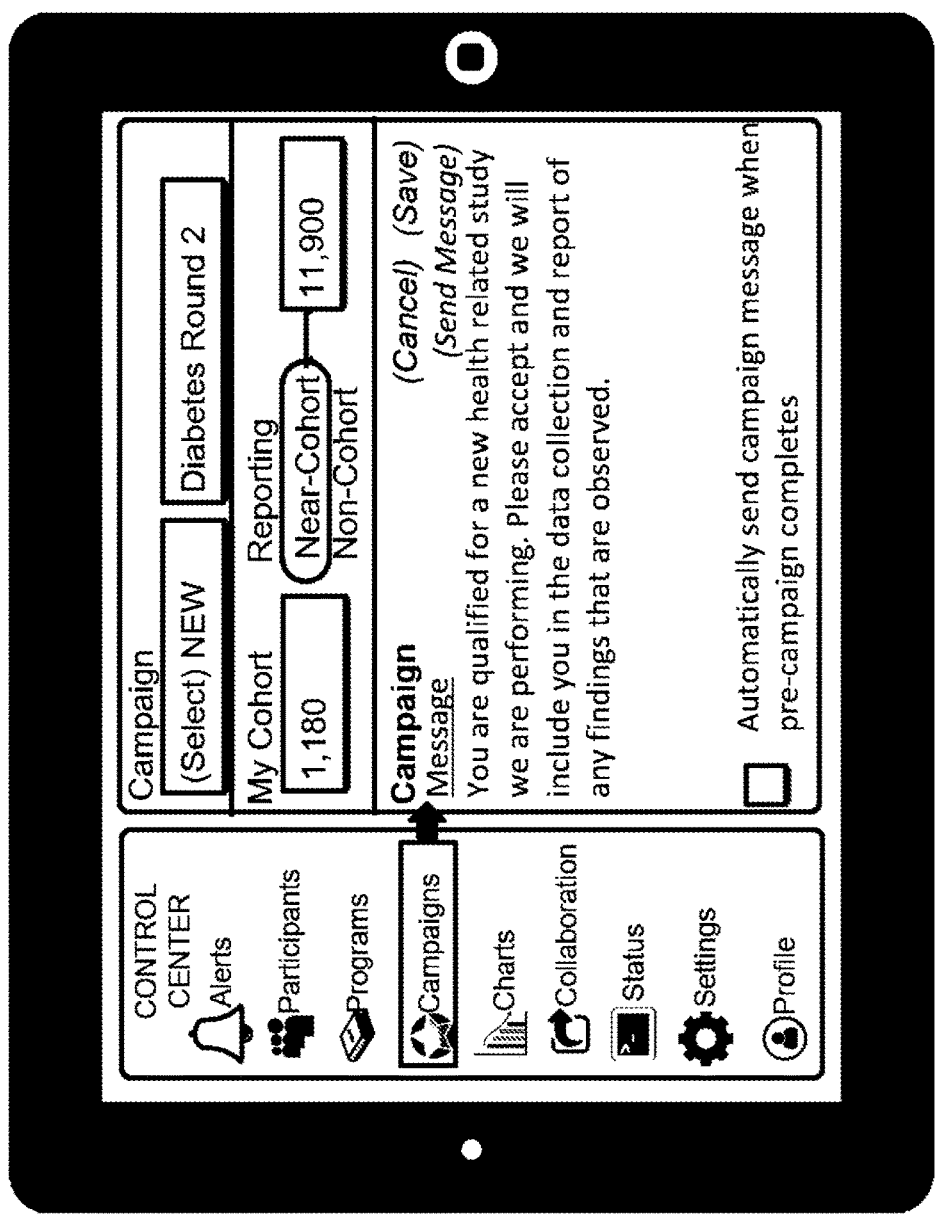

FIGS. 10A-10C illustrate examples of interfaces 1000A-C for cohort outreach and analysis for an existing campaign. The interfaces 1000A-C can be presented through an application (e.g., the study management application depicted in FIG. 1) through which a research can perform various types of operations related to program management.

Referring initially to FIG. 10A, an interface 1000A for performing cohort analysis for a campaign is depicted. In this example, the interface 1000A can be used to analyze data for candidates before a cohort is selected for the study. To identify relevant candidates, the research can specify keywords indicating that a candidate participant would satisfy the selection criteria for the cohort. As shown in FIG. 10A, examples of keywords can include "medication," "pain," "steps," "diabetes," "cardiac," "cancer," "wearables," "opiates," "sleep," "blood pressure," among others. In other instances, the researcher can also specify candidate participant interests that are used to predict user behaviors during the research study (e.g., likelihood of using a mobile device to view exercise activity content, likelihood of using a wearable device during exercise activity).

Referring now to FIG. 10B, an interface 1000B for performing cohort outreach for a campaign is depicted. In this example, the interface 1000B can be used to prepare a message that is sent to all relevant candidates (e.g., candidates identified to satisfy all selection criteria, and participants identified to satisfy a subset of selection criteria). As shown, the message identifies detected gaps in the cohort (e.g., blood glucose sample (schedule), blood pressure (schedule), family history (survey)) so that near-cohort candidates can manually specify whether they meet the detected gaps (e.g., if their participant data is incomplete and does not completely reflect their medical history information).

Referring now to FIG. 10C, an interface 1000C for configuring message delivery for a campaign is depicted. In this example, the interface 1000C can be used to send a confirmation message to candidates that satisfy some or all selection criteria for a cohort. As discussed above, once configured, the message can be delivered to participant devices and provides a way for candidates to confirm participation in the research study by being included in the cohort.

Figure 11:
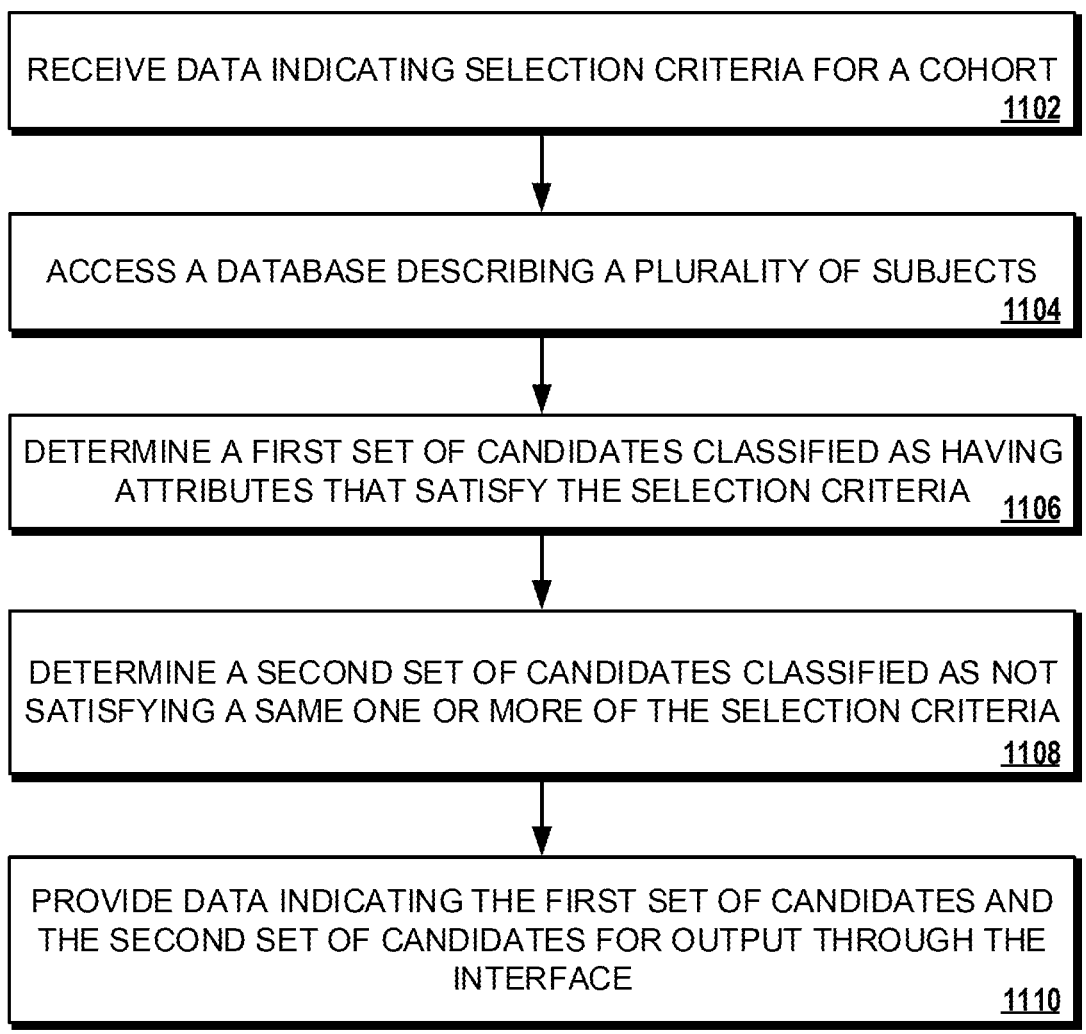
FIG. 11 illustrates an example of a process that can be used to identify and select candidates for a cohort.

FIG. 11 illustrates an example of a process 1100 that can be used to identify and select candidates for a cohort. The process 1100 can be performed by one or more computing devices, such as one or more server computers, one or more client devices, or a combination of server and client devices. As an example, the process 1100 may be performed by the computer system 120.

The process 1100 can be used in an interface for creating and managing research studies. More generally, the process 110 can be used in a database query processing system or search engine system to search for and provide information about candidates for a cohort. For example, the process 1100 can be used to identify and provide information about groups of individuals that satisfy a set of selection criteria and so are fully eligible for inclusion in the cohort. In addition, the process 1100 can provide information about other groups of individuals that do not match all of the selection criteria (e.g., near-miss or nearly-matching individuals). These other groups might be prompted to become eligible or might be eligible if the selection criteria were changed. The system provides information about these cohort candidate groups, such as the size of each group and how well they respectively satisfy the selection criteria (see element 202B of FIG. 2). The system can thus enable a user to quickly see which selection criteria are most limiting and which groups within the participant pool can be added to make up for a shortfall in cohort size, whether by relaxing the selection criteria or by communicating with individuals to encourage them to become eligible.

The process 1100 can be used to provide data for an interface used for selecting a cohort for a research study or for other purposes. The interface may be a user interface, such as through a mobile application, desktop computer application, web application, web page, etc. The techniques can also be used to provide data through an application programming interface (API).

In general, the process of selecting individuals for a cohort can be an iterative process. The computer system 120 may repeatedly perform the actions of the process 1100 over time to identify changes in the sets of candidates available. Similarly, the computer system 120 may adjust the identified candidates as data in the database 122 changes, as selection criteria or study parameters change, and so on.

Briefly, the process 1100 can include, among other operations, receiving data indicating cohort selection criteria through an interface (1102), accessing a database 122 including information about a plurality of subjects (1104), determining a first set of candidates classified as satisfying the selection criteria (1106), determining a second set of candidates classified as not satisfying a same one or more of the selection criteria (1108), and providing data indicating the first set of candidates and the second set of candidates for output through the interface (1110).

In more detail, the process 1100 can include receiving data indicating selection criteria for a cohort through an interface (1102). The data can be received through an interface provided by the one or more computing devices. The computer system 120 can receive data indicating cohort selection criteria through a user interface, such as interface 112. The selection criteria may be received through an API in some cases. For studies that are in the process of being designed, stored selection criteria for the study can be retrieved from the database 122 or from another data storage system.

As an example, the selection criteria can include keywords that identify desired attributes for candidates, such as, a diagnosed medical condition (e.g., diabetes), physiological test data completed (e.g., blood test), a desired age requirement (e.g., older than 30 years old).

The selection criteria can be entered or obtained in various ways. In some implementations, such as the example shown in FIG. 1, the cohort selection criteria is received in the form of a search query. For example, the user may provide a natural language search query that specifies desired characteristics for cohort members, e.g., "people between age 18 and 65 that have high blood pressure." As another example, the system may receive a structured query (e.g., formed according to a structured query language (SQL)) through a user interface or API, where the structured query specifies the criteria for selecting members of the cohort. As another example, the system can provide data for a user interface with selectable controls that allow a user to build a set of selection criteria. The user interface may provide drop down elements with different types of attributes, allowing a user to select the from among age ranges, health status, disease types and stages, demographic groups, and so on to build the set of criteria.

In some implementations, the system extracts or derives the selection criteria from user inputs or text or other data about a study. For example, the system can provide a user interface to receive a research question to be evaluated in a study being designed, e.g., a question such as "What are the effects of exercise and sleep quality on management of type II diabetes in individuals over 55?" From this question or other natural language text, the system can identify keywords that are used to define selection criteria for the cohort to be used in addressing this question. In this example, the inferred selection criteria may be that cohort members should (1) make exercise data available, (2) make sleep tracking data available, (3) be diagnosed with type II diabetes, and (4) be 55 years old or older. The system can store metadata that maps different keywords (e.g., words and/or multi-word phrases) to information in the database 122 and/or types of selection criteria to facilitate this process. In addition, or as an alternative, the system can use machine learning to train a natural language processing model based on the examples of other research questions for other studies (or text more generally) and corresponding selection criteria used in those other studies.

In some implementations, the system can derive selection criteria based on study parameters that a user has set for a study. For example, if a user designs study protocols to acquire daily step tracking data, the system may include a selection criterion that step tracking data is needed for inclusion in the cohort. The process of selecting candidates for a cohort can be iterative, with the groups of candidates being updated and changed in response to changes in any of various aspects of the study (e.g., the research question, data to be collected, types of devices to be used, the techniques for data collection, etc.)

The process 1100 includes accessing a database (e.g., database 122) that includes data describing attributes of a plurality of subjects (1104). In some implementations, the subjects described in the database 122 can be a diverse set of people. In some cases, the information can be included for hundreds, thousands, tens of thousands, hundreds of thousands, or millions of people. The individuals described in the database 122 can be people who have participated in research studies in the past and/or have indicated in participating in the future. In some cases, the database 122 may include information about people treated by a hospital system, people who are part of a longitudinal data collection campaign, or other groups of people.

The attributes indicated in the database 122 can include any of various types of information that describe or characterize the state of the subject, and the attributes can be derived from many different sources. The attributes can describe, for example, physical characteristics (e.g., weight, age, maintenance status, health status, physiological measures, genomics data, proteomics data, etc.). A wide range of electronic health records (EHR) and electronic medical records (EMR) can be included, allowing an indication of medications of individuals (e.g., currently used, previously used, prescribed, etc.), diseases or conditions that individuals have been diagnosed with, blood test results and other medical test results, etc. The attributes can be self-reported by a subject, provided by a third party (e.g., an administrator, a coach, a technician, a doctor, a researcher, a supervisor, etc.), provided by one or more devices (e.g., medical equipment, phones, wearable devices, devices that interact with the subject or monitor the subject, etc.).

As an example, attributes can include vital signs or baseline indicators of health status (e.g., heart rate, respiratory rate, blood pressure, oxygen saturation, respiratory rate, respiratory effort, capillary refill time, temperature, etc.). Other attributes include height, weight, strength measurements, endurance measurements, blood chemistry measurements, genomics data (e.g., data indicating whether the subject has or lacks certain genes or certain classes of genes, indications of which form of a gene is present, etc.), proteomics data (e.g., data indicating the identification, localization, and functional characteristics of proteins of a subject). Subject attributes can include whether a person has been diagnosed with a disease or other condition (e.g., cancer, diabetes, heart disease, chronic obstructive pulmonary disease (COPD), etc.), the current status of the disease (e.g., disease stage or classification, effects or limitations due to the condition, a severity or level of progression of the disease), whether the person has received treatment and what type of treatment, and so on. Attributes may indicate the structure and/or functional capability of any structures or systems of the body. Subject attributes can include mental and psychological indicators such as anxiety levels, pain levels, scores for various personality traits, and so on. The database 122 can include data generated for the subjects over a period of time, and can include information about activities or attributes of the subject at multiple points in time.

The attributes can include attributes that reflect behavior or activities of the individuals. This can include aspects such as diet, exercise, sleep, social activities, etc. The computer system 120, or another system, can track or monitor the attributes and activities of subjects over time and collect information obtained. For example, the computer system 120 may communicate with various other devices to track different aspects of an activity (e.g., type of activity, duration of the activity, intensity of the activity, results of the activity, effects of activity on the subject, etc.) Individual instances of activities may be tracked and/or composite measures of activities (e.g., frequency, average characteristics, etc.) can be tracked. Subjects can be monitored to detect changes in attributes as well.

Among the types of information in the database 122 can be indications of which types of data are available for a subject. For example, the database 122 can indicate which technological tools, such as devices (e.g., scale, blood pressure monitoring device, exercise tracker, glucometer, etc.) and software (e.g., mobile applications, etc.) individuals have. As another example, the database 122 can indicate which types of data the different individuals have provided and/or consented to be shared.

In some implementations, the data in the database 122 may include sensor data collected by one or more sensing devices and sent to the computer system 120. The sensor data may include data collected while the subject, e.g., person, is engaged in a particular activity, in particular, activities such as training activities or assessments. The status data may include data self-reported by the subject, data collected from others, data from sensors, etc.

In some implementations, data in the database 122 can include one or more of heart rate data of the subject, oxygen saturation data of the subject, data indicating an exercise distance that the subject ran or walked, data indicating an exercise intensity that was performed by the subject, or data indicating a duration of an exercise that was performed by the subject. As discussed above, these can be current or recent values (e.g., the most recently measured) and/or prior values (e.g., a series of historical measurements taken at different times). These various data types and other may be collected using multiple sensors and/or devices.

The activities tracked by the computer system 120 can include actions that involve or are performed by the subject. The context of the activities (e.g., the location, date, time day, resources allowed, whether performed in a group or alone, who supervised or instructed the activity, etc.) can be tracked and recorded as well.

The computer system 120 can track attributes or activities of each of multiple subjects over a period of time, as well as changes in the multiple subjects over the period of time. The computer system 120 can train various types of models based on the data in the database 122, as discussed further below. By tracking many variables (e.g., subject attributes, subject activities, context of the subject and activities, etc.) for many subjects and storing the data in the database 122, the computer system 120 can obtain a rich data set with which to discover elements that have relevance to the potential actions of the subjects, including their levels of engagement and retention for participating in research studies. This data, whether used for machine learning training or through direct analysis and extraction of relationships by the computer system 120, can be used to identify which features are predictive of different types of outcomes (e.g., different actions by the subjects or outcomes of subjects during research studies) and to generate models that can be used to make predictions based on those features.

The process 1100 can include determining a first set of candidates classified as satisfying the selection criteria for the cohort (1106). The computer system 120 can use the information in the database 122 to identify a set of candidates identified as satisfying the cohort selection criteria. For example, the system can perform a search for individuals that meet each of the requirements of the selection criteria and thus are fully eligible to be included in the cohort. Individuals that are determined to satisfy the selection criteria are then classified (e.g., assigned to the class or group) as meeting the selection criteria.

The computer system 120 may use various techniques to facilitate search and retrieval and to improve efficiency. These can include translating the selection criteria into a structured or standardized form for comparison with standardized data in the database 122. As another example, the computer system 120 may use a translation layer or translation process to convert from the selection criteria to the data in the database 122. For example, the selection criteria may specify that exercise data is required. One option is for the database 122 to include fields to indicate whether exercise data is available for each individual. Another option is for a translation component to identify, from among the types of data in the database 122, which data would satisfy the exercise requirement (e.g., counts, phone accelerometer data, and self-reported exercise data). Any individual that has at least one of these qualifying types of data may be considered to satisfy the exercise data requirement. Similarly, mapping data may be generated and stored to specify which data types available among the many types of sensor data, tracking data, self-reported data, etc. would satisfy different requirements. The computer system 120 can then use mapping data to determine which data records satisfy the exercise requirement and then which individuals have at least one of the qualifying data types available.

In some cases, machine learning models can be used to determine whether an individual likely satisfies a cohort selection criteria. For example, models can be trained to predict whether a user is likely to have an attribute based on input data indicating other attributes in the database 122. The computer system 120 can generate predictions for individuals based on data for the individuals in the database 122 using the models, and then use the predictions to evaluate whether one or more of the selection criteria are satisfied.

For example, in a case where selection criteria require individuals to have been diagnosed with diabetes, have had at least one blood test in the last year, and are aged over 30 years old, members in the first set of candidates would have all of these features indicated in the database 122. The candidates can be identified by processing participant data (e.g., participant attributes, participant activity patterns) that are specified in the database 122. As discussed above, the database 122 can include data obtained from various data sources, such as electronic health record data, study survey data, mobile devices, medical devices, among other sources.

The process 1100 can include determining a second set of candidates classified as not satisfying a same one or more of the selection criteria (1108). The computer system 120 can use the information in the database 122 to identify another set of candidates identified as satisfying some (but not all) cohort selection criteria. This second set includes individuals that are not included in the first set of candidates and only satisfy a subset (e.g., a proper subset that includes fewer than all of the selection criteria) of the selection criteria.

For instance, for selection criteria that includes diabetes, a blood test, and age over 30 years old, the second of candidates can represent a group of individuals that are each satisfy the first two criteria (e.g., diabetes and blood test) but each do not satisfy the third (e.g., they are less than age 30). As another example, the second group may include candidates that each satisfy the first and third criteria (e.g., have diabetes and are over 30 years old) but each do not have blood test information available. In some implementations, many different second groups can be defined, each representing different combinations of the selection criteria being satisfied.

As discussed herein, the second set of candidates are identified in circumstances where the cohort selection criteria does not produce the necessary number of candidates to be included in a cohort for a research study. For instance, in the example shown in FIG. 1, a research study requires 2,900 candidates, but the number of candidates identified to satisfy the cohort selection criteria is 1,962 participants. In this scenario, the computer system 120 uses clustering techniques to identify additional groups of candidates that partially identify the cohort selection criteria (e.g., groups with participants having attributes that satisfy one or two of the three criteria). Of course, the identification and presentation of multiple sets of candidates, each set representing different levels of match to the selection criteria, need not be limited to the case when the number of fully eligible individuals does not satisfy a minimum. In some implementations, multiple sets of candidates are identified and shown even when no minimum number of cohort members is defined or even when the minimum number of eligible cohort members has been found.

In performing searches over the database 122, there are potentially many different groups of candidates that can be identified, each satisfying a different combination of the selection criteria. The computer system 120 can select from among the many possible groups a subset of them to display based on a number of factors. For example, there may be 15 sets of candidates that are missing different combinations of the selection criteria, and the computer system 120 may selectively provide information about only a predetermined number of the sets, e.g., 5 nearly matching sets of candidates, based on an evaluation of the needs of the study and the relevance of the groups to the selection criteria. Various factors in this selection are discussed below.

One factor is how close each subset of selection criteria is to the full set of selection criteria. Generally, the computer system 120 is configured to prefer to define and display sets of candidates that are closest to eligibility, meaning that the sets represent groups of individuals with the lowest amount of selection criteria not met. For example, sets of candidates that fail to satisfy only one selection criterion can be preferred over sets of candidates that fail to satisfy multiple selection criteria.

Another factor is an analysis of the importance of the selection criteria that are not satisfied by the respective sets of candidates. This can include an analysis of how changeable an element is or how easy it is to correct a missing element. For example, among selection criteria of diabetes, a blood test, and age greater than 30 years old, diabetes may be considered to be the most important and hardest to change. Age greater than 30 may be considered the next most important and difficult to change, while having blood test results is relatively easy to change. As a result, the omission of blood test information from an individual's user profile information in the database 122 may be considered the least disruptive to the goals of the study and the easiest to correct. Thus, the computer system 120 may prefer to show the group that has diabetes and has an age greater than age 30, rather than groups that omit elements needed for selection. The user can recognize that the burden of obtaining a blood test, or perhaps simply agreeing to share blood test results, is quite light and so the members of this second set of candidates may be relatively easily brought into full eligibility. Indeed, as discussed herein, the computer system 120 can even initiate communication with these individuals to encourage them to complete the blood test requirement, either automatically in response to detecting the need for a study being designed or in response to a user's request for the system 120 to expand the pool of eligible individuals.

Another factor in selecting groups to present is the size of the groups. A set that is larger will generally be more useful than a set that is smaller, when the groups have roughly similar levels of match to the selection criteria. This analysis can take into account the size needed for the cohort, as well as potentially the difference between the fully eligible first set of candidates. For example, if a cohort has a target size of 3,000 individuals and 2,000 individuals are in the first set of candidates, the computer system 120 can prioritize sets of candidates that would fill a significant portion of the 1,000-person gap remaining (e.g., sets of candidates with 500 people or more). Of course, since the computer system 120 can perform multi-factor analysis, the computer system 120 can identify combinations of groups that together would complete the cohort, allowing the computer system 120 to present and recommend combinations of sets of candidates that provide the highest likelihood of reaching full eligibility and/or could be encompassed within the selection criteria with the smallest or least disruptive changes to the selection criteria.

The computer system 120 can use these and other factors to generate scores for different combinations of selection criteria, rank the combinations according to the scores, and then selectively provide representations of the groups according to the rankings. Similarly, the information can be arranged (e.g., placed, formatted, etc.) in a user interface according to the scores or rankings. The system 120 can also use the scores and rankings to generate recommendations. For example, the combination assigned the score indicating the highest relevance can be recommended for inclusion in the cohort being defined, either by outreach to the candidates in the second set of candidates to remedy the lacking criteria and/or to adjust the selection criteria to encompass the members of the second set of candidates.

The process 1100 can include providing data for output through the interface (1110). The computer system 120 provides data indicating the first set of candidates and data indicating the second set of candidates for output through interface 116. As discussed in reference to FIG. 1, the data be in the form of user interface elements that identify candidates that satisfy all selection criteria (e.g., eligible candidates), and candidates that partially satisfy all selection criteria (e.g., partially eligible candidates). The user interface elements can identify a number of candidates that are included in each grouping to indicate how many potential candidates can be added for different changes to the selection criteria.

In some implementations, the output data indicating the first set of candidates indicates an amount of individuals included in the first set of candidates. The data indicating the second set of candidates can indicate an amount of individuals included in the second set of candidates. Amounts can be indicated in various ways, such as providing a number, using color coding for different ranges of amounts, sizing representations of sets of candidates in proportion to each other (e.g., with larger user interface elements indicating larger sets of candidates), etc.

The computer system 120 can cause interactive user interface controls to be displayed, to allow a user to act on the sets of candidates to change study parameters including cohort membership. For example, the computer system 120 can provide data causing display of one or more interactive controls corresponding to the first set of candidates, e.g., a control for adding this set to the cohort. In response to receiving data indicating user interaction with the one or more interactive controls, the computer system 120 can add members of the first set of candidates to the cohort for the study being designed.

As another example, the computer system 120 can provide data causing display of one or more interactive controls corresponding to the second set of candidates. These controls can be designed to add, or attempt to add, some or all of the members of the second set of candidates to the cohort. In response to receiving data indicating user interaction with the one or more interactive controls for the second set of candidates, the computer system 120 can add members of the second set of candidates to the cohort. The controls may be used to add these candidates through different options. For example, one option is to remove the selection criteria that caused the candidates in the second set to be excluded, and a user may select this option. For example, in response to receiving data indicating user interaction with the interactive control for a second set of candidates, the computer system 120 can alter the selection criteria to remove the one or more criteria not satisfied by the members of the second set of candidates. Another option is for the user's selection to trigger the computer system 120 to initiate outreach to the members of the second set, to encourage them to remedy the lacking element(s) that prevented full eligibility. Then, as different individuals respond to the prompts from the computer system 120 (e.g., sent as e-mails, mobile application interfaces, surveys, consent forms, etc.), the computer system 120 can automatically add them to the cohort.

In some implementations, the computer system 120 determines a target amount of members for the cohort. This target amount may be input by a user (e.g., a researcher designing a study), may be a default value set by the computer system 120, may be determined by the computer system 120 based on the cohort sizes of other studies involving similar research topics, may be calculated by the computer system 120 in order to provide a desired level of accuracy or precision, or determined in another manner. The computer system 120 can determine whether the amount of participants included in the first set of candidates provides at least the target amount of members. If the amount is greater than or equal to the target amount, the computer system 120 may optionally determine to not provide information about other groups that do not meet all selection criteria. If the amount is determined to be less than the target amount of cohort participants, the computer system 120 may identify and provide information about sets of candidates that are not fully eligible in response. For example, the computer system can help the user fill the rest of the cohort by providing information about the second set of candidates, and potentially also providing recommendations for altering the selection criteria and/or prompting members of the second set of candidates to take specific actions to become eligible.

The computer system 120 can determine that an amount of individuals in the second set of candidates is below a threshold, e.g., a predetermined threshold representing a minimum size for the cohort. In response to the determination, the computer system 120 can provide a recommendation to change one or more of the selection criteria. For example, the individuals in the second set of candidates may satisfy the cohort criteria except for a particular cohort selection criterion. The computer system 120 can provide a recommendation to remove the particular cohort selection criterion not satisfied by the individuals in the second set of candidates.

The computer system 120 may identify a constraint of the selection criteria to recommend to be altered. The constraint may be selected or identified based on the size of one or more sets of candidates lacking a same one or more selection criteria. The computer system 120 can provide data for a user interface element for altering the identified constraint. This may be, for example, a button, hyperlink, or other control that, when clicked, alters the selection criteria. In response to receiving data indicating user interaction with the user interface element, the computer system 120 can alter the constraint to form revised cohort selection criteria, define new sets of candidates for the revised cohort selection criteria, and provide indications of the new sets of candidates.

The indications of the sets of candidates can be coordinated with presentation about other information about the candidates, including information about individual candidates within the sets. For example, the output indicating the first set and second set can be provided in a first portion of a user interface. The user interface can include one or more interactive elements to enable selection of a representation of the first set of candidates or the second set of candidates. The user interface can also include a second portion to display information about candidates within a selected set of candidates. When a user selects one of the sets of candidates, the computer system 120 can provide, for display in the second portion of the user interface, a list of candidates in a selected set of candidates and attributes of the listed candidates. In some implementations, this information can include predictions (e.g., classifications, confidence scores, likelihood scores, etc.) with respect to one or more outcomes. For example, rows representing individuals can be provided, and columns can include likelihood scores or other predictive measures for whether the individuals will respectively have outcomes such as remaining in the study, providing a certain type of data, responding to a certain type of request or message, appropriately using a medical device, participating in calls or appointments, etc. These predictions for an individual can be based on the historical actions of the individual, taking into account the individual's prior responses and patterns. In addition, or as an alternative, the prediction can be based on one or more machine learning models that are trained based on examples of attributes and outcomes of various individuals. This can allow predictions for an individual even when there is no prior history for the individual, because of the relationships the model has learned based on characteristics of similar individuals and how they have acted.

Once a user has selected one or more of the sets of candidates for inclusion in the cohort, the computer system 120 can initiate an enrollment process for the selected candidates. This can include sending communications to devices associated with the individuals, sending requests for responses or other information, initiating data tracking, and otherwise initiating the study for selected cohort members who complete enrollment.

In some implementations, the cohort selection process is used to select a cohort for ongoing or prospective monitoring, so that data gathered after the cohort is defined is used for the study. This is not a requirement, however, and the same cohort selection and management techniques can be used to select cohorts for studies that are retrospective or based on prior collected data. For example, the system can be used to select a cohort of individuals whose records of prior actions or health characteristics can be used for analysis to answer a research question. In this scenario, the results of a study based on retrospective or already collected data may be generated and provided immediately or very soon after the study is defined. Even when generating studies for prospective data collection, this feature can also provide a mechanism for researchers to try out study parameters and obtain sample results, effectively simulating a study based on prior data in the process of designing the study to preview potential results of the study as currently designed. The study parameters and cohort selection criteria can then be changed to iteratively refine the study, each time providing an updated preview or simulation based on past data. Once the researcher is satisfied with the study parameters, the system can be used select a cohort for further prospective data gathering, for example, a larger study or a follow-up study to confirm the expected findings expected from the analysis of data in the database 122.

In some implementations, the data outputted through the interface 116 can include recommendations generated by the system 100 in response to processing participant data stored in the database 122 in response to receiving the cohort selection criteria. For example, as shown in FIG. 1, the recommendation can include a notification to the researcher to make an adjustment to the selection criteria (e.g., removing a specific criterion) to increase the number of eligible candidates. In some instances, the recommendations can also include confidence scores computed by the system to represent a predicted likelihood that a given candidate group satisfies the selection criteria. For example, a confidence score with a value of "0.99" can represent a 99% likelihood that members of a candidate group are eligible for selection in a cohort, while a confidence score with a value of "0.15" can represent a 15% likelihood that members of a candidate group are eligible for selection in a cohort. The values of confidence scores can be based on, for example, the number of selection criteria that are identified as being satisfied by members of a candidate group, the nature of the attributes used to make an initial eligibility determination (e.g., variability or uncertainty among the source data), among other types of determinations.

In some implementations, the data indicating the selection criteria is received from a client device over a computer network. The output data that indicates the first set of candidates and the second set of candidates can include output data provided to the client device over the computer network. The database 122 can include sensor data acquired from mobile devices associated with the subjects. The first set of candidates and the second set of candidates can be determined based at least in part on the sensor data in the database 122.

The determinations whether individuals satisfy the selection criteria can be made based at least in part on processing performed using models, such as machine learning models. For example, a prediction score can be generated for each subject in a plurality of subjects. Each prediction score can be indicative of a prediction made for the corresponding subject using one or more machine learning models that have been trained based on attributes of other subjects. At least one of the first set of candidates or the second set of candidates may be determined based at least in part on the prediction scores.

The computer system 120 can determine whether to include a subject in a set of candidates for a cohort based on (i) an amount of the selection criteria that subject satisfies and (ii) a prediction score for the subject that is indicative of a probability of the subject achieving a predetermined outcome. For example, to increase the likelihood of success of the cohort, groups may be filtered based on machine learning predictions about the future actions of individuals, such as whether the individuals will participate with a desired level of engagement and/or will continue participating (e.g., be retained) through the completion of the study. The predictive scores can be generated using one or more machine learning models that have been trained based on attributes and/or activities of other subjects, as well as data indicating whether the other subjects achieved the predetermined outcome. By filtering cohorts with this type of prediction, a larger percentage of enrolled members of cohorts can be retained, allowing for greater efficiency and reduced overhead. For example, rather than requiring 25% headroom in a cohort (e.g., enrolling 1,250 individuals for a cohort that needs 1,000 members), a cohort with less headroom (e.g., 5% or 10%, or another value, depending on the accuracy of the predictive models) can be used.

In some implementations, the computer system 120 identifies multiple second sets of candidates, wherein the different second sets of candidates satisfy different proper subsets of the selection criteria. Each of the multiple second sets of candidates can be formed of individuals that satisfy only a same proper subset of the selection criteria (e.g., each of the members of a second set all lack the same one or more of the selection criteria). Information about the multiple second sets of candidates can be provided for display along with the data indicating the first set of candidates. For example, the provided data can include (i) data indicating each of the multiple second sets of candidates and (ii) an indication, for each of the multiple second sets of candidates, of one or more items of the selection criteria that are not satisfied by the members of the second set of candidates. The size of each of the second sets of candidates can also be indicated.

In some implementations, the selection criteria are associated with a research study, e.g., a study being designed. The computer system 120 can obtain log data corresponding to each candidate included in a particular set of candidates, where the log data comprises at least one of a health history, a demographic profile, health data collection patterns, or actions of a user when previously participating in a research study. The log data may represent data obtained over time, e.g., records resulting from repeated measurements and data collection actions for each of the individuals described in the database 122. The computer system 120 can determine, for each candidate in a group and based on the log data, a score representing a predicted likelihood that the candidate will complete the research study if selected to be included in a cohort for the research study. For example, the computer system 120 can use the data in the database 122 about an individual to determine feature values that serve as inputs to one or more machine learning models. Similarly, the computer system 120 can use the data from the database 122 to perform pattern matching with profiles or ranges of values associated with individuals that have completed other studies. Rule-based models, statistical models, and other types of models can be used. The computer system 120 can provide output data indicating the scores determined for the particular set of candidates. Similarly, the computer system 120 may use the score to filter out candidates from being included in a cohort, for example, by removing one or more individuals from consideration based on predictions for the individuals indicating less than a minimum likelihood of complying with study requirements (e.g., providing needed data, attending appointments, using a mobile device or other technology, etc.) or continuing to the end of the study.

The computer system 120 may use the parameters of the study being designed to tailor the predictions regarding outcomes for individuals. For example, each study may have its own set of protocols and requirements, so that different studies require different levels of active engagement by participants. For example, some studies may require in-person meetings and others may not. Similarly, different studies require different types of data to be collected using different techniques. Predictions of likelihoods of outcomes can be based on the study protocols and requirements, so that the predictions of outcomes for a study are tailored for the particular types of actions and the overall burden imposed by that study.

For example, a machine learning model can be configured to receive, as input, (i) feature scores that indicate the study requirements (e.g., study duration, types of responses needed from subjects, types of hardware and software used, type and frequency of data collection, etc.) and (ii) feature scores that indicate a variety of attributes of an individual (e.g., demographic information, survey responses, and other data about the individual), including potentially actions that the individual has performed in the past (e.g., successfully completing appointments, failing to complete appointments, use of a medical device or an application, participation in a prior study, etc.). From these inputs, the machine learning model may provide one or more scores that indicate likelihood of the user performing different actions. For example, there may be a score predicting a likelihood of being retained in the study until the end, a score predicting a likelihood of the individual providing a particular type of data, a score predicting a likelihood of the individual responding to e-mail or another type of communication, and so on. The machine learning model may be, for example, a neural network, a support vector machine, a classifier, a regression model, a reinforcement learning model, a clustering model, a decision tree, a random forest model, a genetic algorithm, a Bayesian model, or a Gaussian mixture model. The machine learning model may be trained by using the many individuals whose data is in the database 122 as training examples. For example, for participants of prior studies, the computer system 120 can use the database 122 to determine outcomes for those participants, the study requirements for the studies they participated in, and the attributes of the participants. The outcomes can then be used as training targets for different training iterations to adjust the parameters of the machine learning model (such as weights for an artificial neural network) to predict the outcomes.

Figure 12:
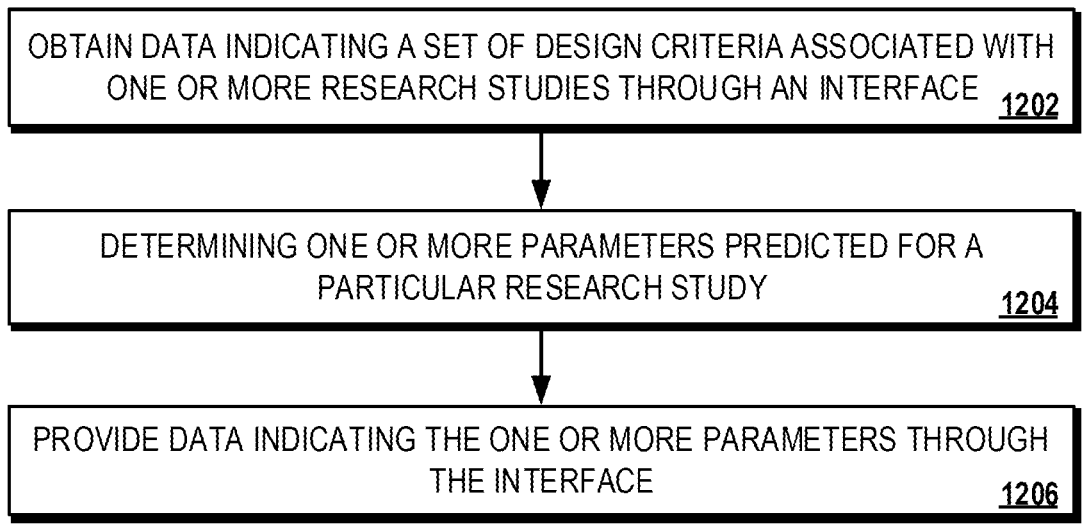
FIG. 12 illustrates an example of a process for adjusting aspects of a research study.

FIG. 12 illustrates an example of a process 1200 for adjusting aspects of research study. The process 1200 can be performed by one or more computing devices, such as one or more server computers, one or more client devices, or a combination of server and client devices. As an example, the process 1200 may be performed by the computer system 120.

Briefly, the process 1200 can include the operations of obtaining data indicating a set of design criteria associated with one or more research studies through an interface (1202), obtaining data indicating attributes of individuals available to participate in a research study (1204), determining one or more parameters predicted for a particular research study (1206), and providing data indicating the one or more parameters through the interface (1208).

In more detail, the process 1200 can include obtaining data indicating a set of design criteria associated with one or more research studies through an interface (1202). The computer system 120 can obtain data indicating design criteria associated with a research study. As shown in FIG. 2, the design criteria can be specified in a query 201A submitted by a researcher through an interface 202. For example, the design criteria can include keywords representing conditions to be evaluated in the study (e.g., blood cancer, exercise activity, participant age). In some instances, the computer system 120 can identify the design criteria based on processing text within research study documents uploaded through the interface 202 (e.g., research proposal document).

The process 1200 can include obtaining data indicating attributes of individuals available to participate in a research study (1204). The computer system 120 can obtain data indicating attributes associated with participants enrolled in a study (e.g., participants selected for a cohort for a research study) or attributes of participants that are eligible to enroll in the study but necessarily participating in it (e.g., participants of other research studies having attributes that make them eligible for a target research study). As discussed throughout, participant attributes can include various types of identifying information, such as demographic information, blood samples, genomic data, behavioral or lifestyle information, among other types of information. The participant data can include historical data (e.g., data for participants collected in prior concluded research studies) as well as ongoing data (e.g., participant data collected while a target research study is being conducted).

The process 1200 can include determining one or more parameters predicted for a particular research study (1206). Various types of study parameters can be predicted (e.g., duration, type of data collected, frequency for data collection, types of communications with participants, etc.). The computer system 120 can determine one or more predicted parameters 201B for a target research study by applying the trained machine learning models 124. As shown in FIG. 2B, the computer system 120 can use the machine learning models 124 to identify patterns within the participation data 122A and historical study data 122B. For example, the machine learning models 124 can identify actions that participants enrolled in a target study have previously performed in completed research studies, which is then used to determine a high likelihood of subsequent non-compliance during the target study. As another example, the machine learning models 124 can identify prior unsuccessful study outcomes for studies that have similar design parameters as a target study to determine a high likelihood of a subsequent unsuccessful study outcome for the target study. In some other examples, the machine learning models 124 can specifically identify current design parameters of a target study that may benefit from refinement (e.g., questionnaire format, monitoring frequency of participants, required actions for participants, etc.).

The machine learning models can be trained perform different types of predictions. The machine learning models can be trained based on different data sets to make the different predictions. For example, models can be trained to predict study parameters based on input indicating the research questions or topics of the study. The models can be trained with examples of the questions and topics of prior studies that completed successfully, as well as the techniques, protocols, and parameters of those studies. Thus, the models can learn the types of data to be collected and the techniques to be used for different areas. For example, in response to input feature data indicating that a research topic involves diabetes, the model may provide output predicting that the study should include glucose monitoring, blood pressure monitoring, and include periodic blood tests.

Another type of prediction can help adjust study parameters to improve engagement and retention. For example, models can be trained based on the attributes of individuals in prior studies, the actions the individuals needed to perform in those studies, and the rates of success of individuals in completing the studies or the rates of success of the studies as a whole. The model can be configured to receive input indicating characteristics of a cohort (e.g., demographic attributes and other cohort statistics) and requirements on cohort members (e.g., data collection needed, types of data needed, types of hardware or software used, etc.), and to output a prediction that the study will be successful.

As another example, the models can be trained to receive cohort statistics and provide outputs that indicate likelihoods that the cohort can successfully complete the study with different parameters, e.g., a duration of 1 month, a duration of 3 months, collection of step tracking data, collection of sleep data, etc. In this way, the models may provide scores for each of multiple potential study elements or study parameters. This data can be provided for display to a user to assist the user in designing a study. The information may also be used by the computer system 120 to provide recommendations of study parameters to use (e.g., elements to include in the study) and recommendations of parameters to avoid (e.g., warnings that certain current parameters may lead to low likelihoods of successfully completion of a study.

In the examples discussed above, the predicted study parameters represent recommendations to change the existing design parameters for a study. In other instances, the predicted study parameters can represent suggestions for a researcher to design a new study in a particular manner based on the participant data 122A and the historical study data 122B. For example, the machine learning models 124 may identify a specific survey type that is most likely to be completed by enrolled participants, a specified monitoring frequency that was successfully applied in other research studies, the type of follow-up notifications to provide to enrolled participants, among others.

The process 1200 can include providing data indicating the one or more parameters through the interface. The server system can provide data indicating the predicted study parameters 204 to the researcher device 110 through the interface 202. As shown in FIG. 2, the predicted study parameters 204 are displayed as information presented through interface elements 202C and 202D. In FIG. 2, design parameters are predicted for a new research study for which a cohort has not yet been selected. Interface element 202C thereby identifies a list of recommended cohort candidates to select based on evaluating how likely a particular cohort candidate will complete the research study (e.g., based on how often the particular cohort candidate completed previous studies) and how likely the particular cohort candidate will use a medical device to be compliant with the requirements set forth by the research study (e.g., based on participant data indicating a frequency by which the particular cohort candidate uses a medical device).

Figure 13:
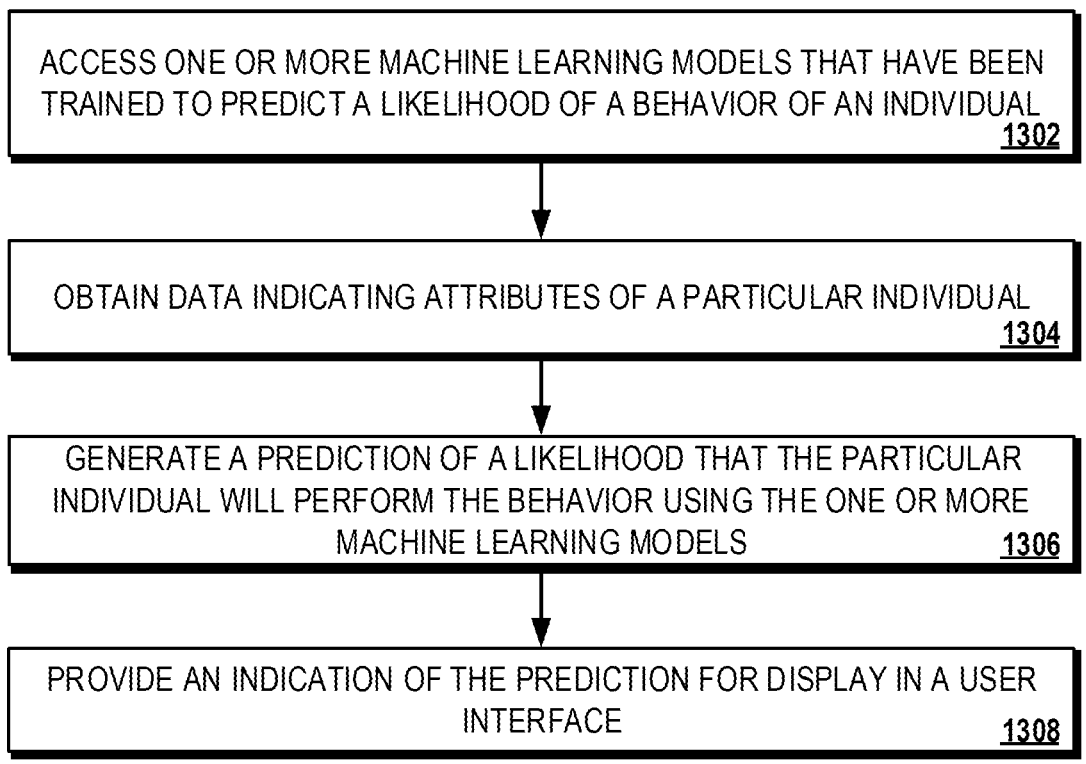
FIG. 13 illustrates an example of a process for applying machine learning to participant attributes to predict participant compliance during an ongoing research study.

FIG. 13 illustrates an example of a process 1300 for applying machine learning to participant attributes to predict participant compliance during an ongoing research study. The process 1300 can be performed by one or more computing devices, such as one or more server computers, one or more client devices, or a combination of server and client devices. As an example, the process 1300 may be performed by the computer system 120.

Briefly, the process 1300 can include the operations of accessing one or more machine learning models that have been trained to predict a likelihood of a behavior of an individual (1302), obtaining data indicating attributes of a particular individual (1304), generating a prediction of a likelihood that the particular individual will perform the behavior using the one or more machine learning models (1306), providing an indication of the prediction for display in a user interface (1308).

In more detail, the process 1300 can include accessing one or more machine learning models that have been trained to predict a likelihood of a behavior of an individual (1302). The computer system 120 can access the machine learning models 124, which, as discussed throughout, can be trained to predict a behavior of an individual based on participant data for individuals and historical information behavior of the individuals. As examples, training data can include data identifying inputs submitted by individuals through a user device when participating in prior research studies (e.g., input provided in a research study survey), behaviors and/or actions performed in association with prior research studies (e.g., whether an individual was compliant in meeting the requirements set forth for participants), or other factors that may affect an individual's behavior or preference (e.g., an individual's age reflecting a familiarity or preference for a certain type of content presentation through his/her user device).

The process 1300 can include obtaining data indicating attributes of a particular individual (1304). The computer system 120 can obtain data indicating attributes for an individual that is included for a cohort for a research study and is indicated to be participating in the research study. As discussed throughout, the attributes can identify actions that the individual has performed while participating in the research study, inputs submitted by the individual (e.g., completed surveys, feedback forms, etc.), or other types of identifying information (e.g., demographic profile, medical history, genomics information, etc.).

The process 1300 can include generating a prediction of a likelihood that the particular individual will perform the behavior using the one or more machine learning models (1306). The computer system 120 may generate a prediction of a likelihood that the particular individual will perform a certain behavior using the machine learning models 124. The behavior may vary depending on the type of prediction being performed. For example, in some instances, the computer system 120 predicts a likelihood that the particular individual will complete a participant survey to be subsequently provided to the individual while the research studying is being conducted. In this example, the prediction can be based on historical activity data indicating whether the particular individual has completed surveys in research studies that he/she has previously participated, a user's preferences for different survey types. In other instances, the computer system 120 predicts a likelihood that the particular individual will successfully complete the entire research study (e.g., that the individual will not drop out of the research study). In this example, the prediction can be based on historical data indicating the completion rates of other individuals in similar research studies, or specifically, historical data of the individual's participation in previous research studies.

The process 1300 can include providing an indication of the prediction for display in a user interface (1308). The computer system 120 can provide an indication of the prediction for display through the user interface 202. For example, as shown in FIG. 2, the prediction can be displayed in the table included in interface element 202C (e.g., completion predictor, use of medical device). As another example, the prediction can be provided as a notification through the interface 202 that notifies a researcher that a particular individual is not likely to complete a response survey. In this example, the notification may include an option for the researcher to modify the response survey (e.g., modify the questions included in the response survey, or the type of user input requested for completion) to improve the predicted likelihood of completion.

Figure 14:
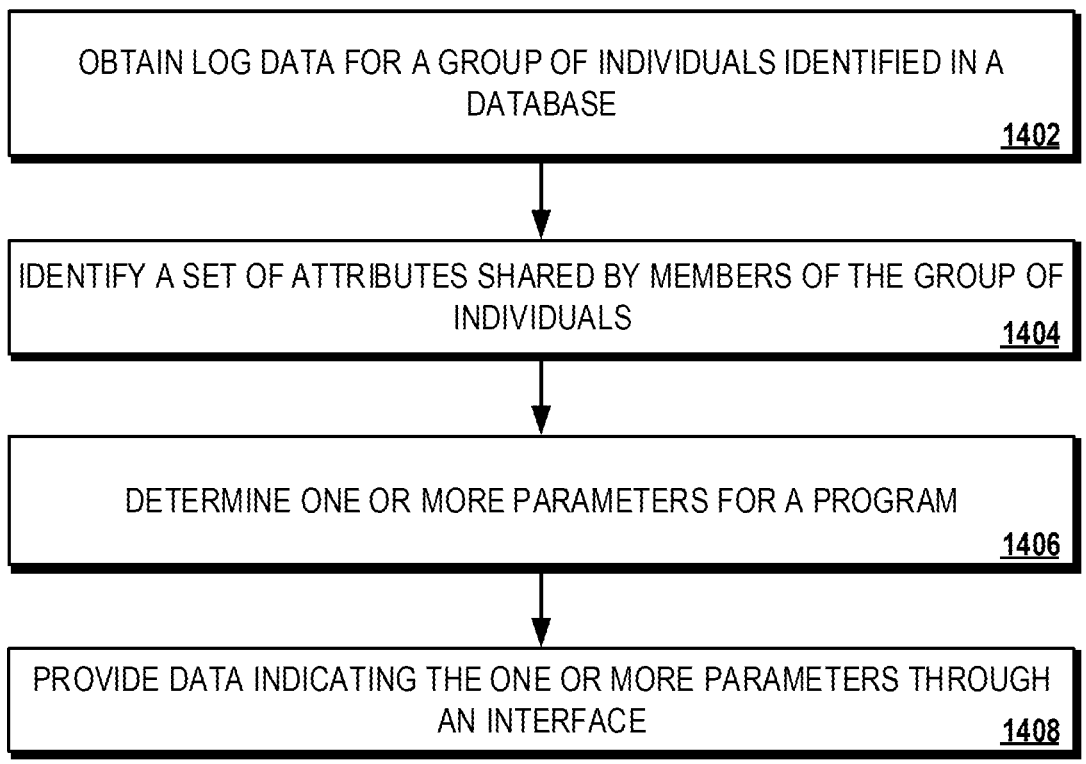
FIG. 14 illustrates an example of a process for determining parameters for a program based on attributes shared by members of a group.

FIG. 14 illustrates an example of a process 1400 for determining parameters for a program based on attributes shared by members of a group. The process 1400 can be performed by one or more computing devices, such as one or more server computers, one or more client devices, or a combination of server and client devices. As an example, the process 1400 may be performed by the computer system 120.

Briefly, the process 1400 can include the operations of obtaining log data for a group of subjects identified within a database (1402), identifying a set of attributes shared by members of the group of subjects within the log data (1404), determining one or more parameters for a program (1406), providing data indicating the one or more parameters through an interface (1408).

In more detail, the process 1400 can include obtaining log data for a group of subjects identified within a database (1402). The computer system 120 can obtain log data for a group of subjects identified within the database 122. The log data identifies information collected for members of the group of subjects during participation in a set of previously completed programs (e.g., research studies, data collection campaigns, etc.). For example, the log data can include EHR data, study survey data, historical study data, and cohort participant data for participants that were included cohorts for a set of previously completed research studies.

The process 1400 can include identifying a set of attributes shared by members of the group of subjects within the log data (1404). The computer system 120 can identify a set of attributes shared by members of the group of subjects based on the information collected for members of the group of subjects during participation in the set of previously completed programs. As examples, the attributes can include responses that participants provided in response to being provided with survey questions during a research study, actions performed by participants in response to being presented with content through an application, activities related to a research study (e.g., taking a medication, performing exercise-related activities, compliance with requirements specified by an experimental treatment plan), or other types of activity patterns that are recognized within collected data. As discussed throughout, the computer system 120 can identify the attributes by processing the various types of data collected for participants in previously completed research studies (e.g., demographic data, genomics data, EHR data, survey response data, passively sensed data, sensor data, etc.).

The process 1400 can include determining one or more parameters for a program (1406). The computer system 120 can determine parameters for a program based on the set of attributes shared by members of the group of subjects using one or more machine learning models. The machine learning models can be trained to predict parameters of programs including the types of data to be collected. For instance, the computer system 120 can determine a research question to be investigated in a study based on applying machine learning models that are trained to identify patterns within previously collected study data. As an example, if a large percentage of participants within the database 122 that previously participated in an insomnia study are also identified to have heart disease, then the computer system 120 can generate a research question for investigating the impact of heart disease on insomnia (based on the correlation identified by machine learning models within the participant data).

In other instances, the computer system 120 can determine the presentation method of displaying content to participants in a new study based on attributes indicating actions performed by participants after previously being provided with content in previous studies. For example, machine learning models can identify the most effective presentation method by evaluating interaction data of participants collected during previously conducted studies to identify the type of content that is mostly likely to illicit a response from a participant. In this example, the machine learning models can evaluate, for example, the average time for a participant to provide an input after being provided with content, the types of actions performed by participants after being provided with content, or user preferences specified in feedback elicited from participants during a study.

In other instances, examples of parameters determined by the computer system 120 using machine learning models can include the type of data to collect during a study, the number of participants to include in a cohort for the study, the types of participants to include in a cohort (e.g., demographic information, medical and diagnostic history, activity pattern information), the actions requested to be performed by subjects (e.g., frequency of providing feedback, the manner in which feedback is provided), design information for surveys to be used during a study (e.g., survey format, survey presentation, types of questions included in the survey), among others. In each of these examples, patterns detected in historical data can be evaluated to identify opportunities to conduct more effective research studies. In this way, the system is capable of identifying research improvement opportunities without requiring a researcher to explicitly specify how such improvements can or should be made.

The process 1400 can include providing data indicating the one or more parameters through an interface (1408). The computer system 120 provides data indicating the one or more parameters through an interface that is presented to a researcher. For example, as shown in FIG. 1, the parameters can be provided through the interface 114 of a study management application that the researcher uses to define a cohort for a new study. As another example, in FIG. 2, the interface 202 includes an interface element 202D that identifies parameters represented by additional research topics of interests given participant data 122A and historical study data 122B stored in database 122.

In some implementations, the set of attributes shared by members of the group of subjects includes an attribute identifying a disease condition. For example, the attribute can indicate that participants that previously participated in a study were all previously diagnosed with high blood pressure. In such implementations, the one or more parameters for the program includes a parameter specifying evaluation criteria associated with the disease condition. For example, the parameter can identify a blood pressure test to be performed for participants in a study for evaluating overall cardiovascular health.

In some implementations, the set of attributes shared by members of the group of subjects includes an attribute identifying a behavioral pattern. For example, the attribute can indicate a particular action that participants have performed in response to receiving a program notification on a mobile device (e.g., dismissing the notification, selecting the notification and performing a specified action, viewing the notification but not performing a specific action response to the notification). In such implementations, the one or more parameters for the program includes a parameter specifying a survey question corresponding to the behavioral pattern to be provided to members of the group of subjects. For example, the parameter can specify a survey format that is identified to be most frequently completed by participants after a notification to complete the survey has been provided to participants. In this example, the survey format can specify, for instance, the types of survey questions included, the types of inputs to be provided by subjects, or the data fields that are included in the survey.

In some implementations, the one or more parameters for the program includes a parameter specifying selection criteria for the program. For example, the parameter can include criteria for candidates to be included in a cohort to participate in a research study. As discussed throughout, examples of selection criteria specify demographic criteria (e.g., age range, gender), disease conditions (e.g., diagnoses), experience or expertise (e.g., a number of previously participated research studies), among other factors. In such implementations, the process 1400 can further include determining, from among the group of subjects, a subset of subjects as having attributes that satisfy the selection criteria. For instance, the computer system 120 can determine a subset of candidates that have attributes satisfying the selection criteria specified for a program. The process 1400 can also include providing, through the interface, data indicating the subset of subjects. For example, as shown in FIG. 1, the server 1400 can identify the subset of candidates through the interface 114.

In some implementations, the log data includes a set of historical actions performed by members of the group of subjects. For example, the set of historical actions can include actions performed by participants in response to being provided with content associated with a program (e.g., a notification to perform a requested action), survey responses and/or other feedback submitted by participants, or other actions performed by participants during participation in a previously completed research study. In such implementations, the one or more parameters for the program are determined by performing additional steps. The steps operations can include determining, using the one or more trained machine learning models, a set of future actions likely to be performed by members of the groups of subjects. The computer system 120 can use machine learning models to predict similar actions that a participant is likely to perform in a subsequent research studies based on frequently performed actions performed in prior similar research studies. For example, if a participant failed to submit written feedback in a research study evaluating a chronic condition, then the parameter may specify that the participant is unlikely to submit written feedback in a subsequent research study.

As another example, if a participant has a history of withdrawing from prior research studies (e.g., due to failure to comply with participant requirements), then the parameter may specify a high likelihood of the participant not completing a new research study. The additional steps can also include identifying one or more operations to be performed during the program to evaluate the set of future actions. For example, if a participant is identified to most likely respond to a certain type of notification, the one or more operations can include using the certain type of notification to provide program content to the participant. As another example, if a participant is unlikely to provide required feedback information to a researcher, the one or more operations can include instructions to provide additional reminders to the participants to improve the likelihood that the participant provides the required feedback information.

In some implementations, the log data includes sensor data collected by computing devices associated with members of the group of subjects during participation in the set of previously completed programs. For example, the sensor data can include physiological data (e.g., heart rate data, blood pressure data, step count, floors climbed, etc.), interaction data collected by a mobile device (e.g., screen activity time, applications frequently accessed, messages sent, etc.), or other types of activity information during participation in prior research studies. In such implementations, the one or more parameters for the program are determined by performing additional steps. The additional operations can include determining a physiological parameter that is (i) included in the sensor data collected by computing devices associated with members of the group of subjects and (ii) was monitored for members of the group of subjects during participation in the set of previously completed programs. For example, the physiological parameter can be a measured heart rate for participants that participated in a research study evaluating long-term effects of exercise activity on cardiovascular health. The additional steps can also include identifying one or more operations to be performed during the program to evaluate the physiological parameter. For example, the operation can include monitoring and/or evaluating heart rate to identify health risks, such as comparing a heart rate measured for a participant to baseline heart rate to determine an abnormally high or abnormally low heart rate, identifying an irregular heart rate pattern, or evaluating a measured heart rate in relation to exercise activity presently being performed by a participant.

Figure 15:
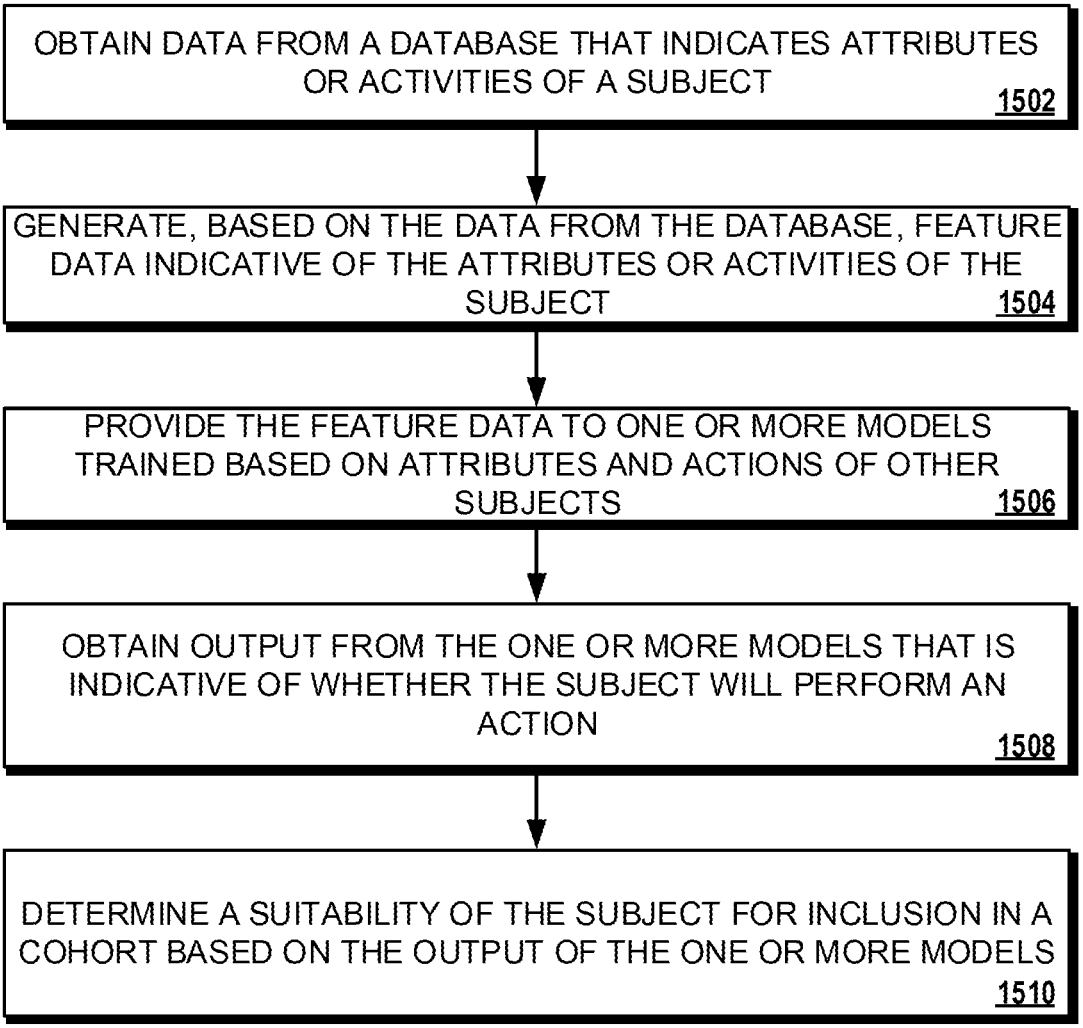
FIG. 15 illustrates an example of a process that can be used to predict how an individual will act, for example, whether the individual will perform the actions needed to participate in a research study.

FIG. 15 illustrates an example of a process 1500 that can be used to predict how an individual will act. The process 1500 can be performed by one or more computing devices, such as one or more server computers, one or more client devices, or a combination of server and client devices. As an example, the process 1500 may be performed by the computer system 120.

The predictions generated using the process 1500 can be used to improve selection of cohort members so that engagement and retention in a research study are enhanced. For example, the process 1500 can be used to predict whether a candidate (or group of candidates) will successfully complete the requirements of a particular research study being designed. Similarly, the same techniques can be used to predict the likelihood that members of a cohort in an active, ongoing study will remain engaged and be retained in participation.

The predictions can trigger the computer system 120 to take actions to improve the likelihood of success of the cohort and the study overall. For example, if individuals are predicted to have a low likelihood of performing an action needed for a study, the computer system 120 may recommend to a researcher to remove or change that action, or even to replace it with a substitute action predicted to be more likely to be performed by the individuals. As another example, if an individual is predicted to have a low likelihood of completing a study, the system 120 can remove that person from consideration for the cohort or can warn a researcher of the low likelihood. If a member of a cohort is predicted to have low engagement or a low completion likelihood, the computer system 120 can take actions to improve the likelihood, such as to change communication with the individual (e.g., changing the frequency or type of communications to improve responsiveness), alert the researcher, etc.)

The process 1500 can include obtaining data from a database 122 indicating attributes or activities of a subject (1502). This can include obtaining information as discussed above for step 1104 of FIG. 11. In some implementations, the subjects described in the database 122 can be a diverse set of people. In some cases, the information can be included for hundreds, thousands, tens of thousands, hundreds of thousands, or millions of people. The individuals described in the database 122 can be people who have participated in research studies in the past and/or have indicated in participating in the future. In some cases, the database 122 may include information about people treated by a hospital system, people who are part of a longitudinal data collection campaign, or other groups of people.

The attributes indicated in the database 122 can include any of various types of information that describe or characterize the state of the subject, and the attributes can be derived from many different sources. The attributes can describe, for example, physical characteristics (e.g., weight, age, maintenance status, health status, physiological measures, genomics data, proteomics data, etc.). A wide range of electronic health records (EHR) and electronic medical records (EMR) can be included, allowing an indication of medications of individuals (e.g., currently used, previously used, prescribed, etc.), diseases or conditions that individuals have been diagnosed with, blood test results and other medical test results, etc. The attributes can be self-reported by a subject, provided by a third party (e.g., an administrator, a coach, a technician, a doctor, a researcher, a supervisor, etc.), provided by one or more devices (e.g., medical equipment, phones, wearable devices, devices that interact with the subject or monitor the subject, etc.).

The process 1500 can include generating, based on the data from the database 122, feature data indicative of the attributes or activities of the subject (1504). The feature data can include feature scores (e.g., a vector of values) that specify attributes or activities of the subject. The attributes can be current attributes or former attributes, and so can reflect the progress or change experienced by the subject over time. Similarly, the activities indicated can be current or former activities, such as a set of activities performed to enhance the subject's capability (e.g., training actions, tasks attempted or performed and associated outcomes, etc.). Some feature scores may be based on user interaction with a device, such as user input to a graphical user interface, responses to questions, entered text. Other feature scores may be based on data collected in other ways.

The feature scores can be based on sensor data that is acquired by one or more sensors during one or more activities of the subject or that indicates one or more attributes of the subject. For example, the sensor data can indicate measurements or detection of attributes and activities of the subject, and the feature scores can be the measured or detected values or other values derived from them (e.g., sensor measurements that have been normalized, quantized, rounded, combined, or otherwise adjusted, or classifications based on the measurements). Examples of sensors that can provide data include accelerometers, proximity sensors, temperature sensors, pressure sensors, optical sensors, cameras, GPS receivers, and so on. Examples of sensing devices that can measure physiological parameters include oximeters, glucometers, electrocardiogram sensors, heart rate sensors, electroencephalogram sensors, electromyogram sensors, and respiration rate sensors.

The set of feature scores can include a value for each of multiple predetermined feature types. The feature types can be a predetermined set of data types that have been previously determined by the computer system, for example, as part of analyzing data in the database 122 and constructing the one or more models. The computer system can store data indicating the set of features types (e.g., data types or types of measures to be generated) that correspond to each model. For example, different models for different types of subjects may use feature scores representing different types of information about subjects.

The feature scores may include data converted to an input format that the model is configured to accept (e.g., binary values, integers, or other values in a predetermined representation). The feature scores may indicate attributes of the person such as, for example, physiological attributes, such as height, weight, blood pressure, health status, and psychological attributes.

To derive the appropriate set of feature scores, the computer system 120 can select one or more models that are appropriate for the type of prediction to be made. For each model, stored data can indicate the feature types to be used with the model, such as the types of information to be provided as input and the format for providing the data to the model (e.g., binary values, integers, floating point values, an appropriate level of precision, etc.). Once the computer system 120 selects a model to use, the computer system 120 can access the data specifying the input feature types for that model and generate them in the format the model is designed to accept.

In general, as part of generating predictive models, the computer system 120 can assess the predictive ability of different data types to indicate likelihoods of future behavior. From this analysis, the computer system can select a subset of the available types of data about subjects to use as features providing inputs to the predictive models. The subset can be a proper subset, e.g., fewer than all of the available types of data. The analysis can be performed at a fine-grained level, for example, with a different set of feature types used for each type of action to be predicted (e.g., response to a survey, replying to a text message, retention in a study, providing sleep data etc.). Indeed, the computer system 120 can train different models for types of predictions, with each model having a corresponding set of feature types representing a subset of the types of information available in the database 122.

The set of feature scores derived from the database 122 can include information about different attributes and/or activities of the subject over time. For example, the feature scores may indicate the activities or attributes of the subject at each of multiple points in time. For example, different instances of activities (e.g., training activities, attempts to perform a task, etc.) can each be provided so they can be used in making predictions. Similarly, the values or measures indicative of different subject attributes at different times can also be provided. In some cases, information about different points in time, e.g., time series data for a subject, can be provided by concatenating multiple sets of feature values, each representing attributes and activities at different times, into a single input feature vector or input data set for a model. As another example, multiple sets of feature values can be provide to a model separately, e.g., sequentially as a sequence of multiple feature vectors, and the model can include a memory capability to retain information from the processing of one input vector to the next. A recurrent neural network, such as one including long short-term memory (LSTM) blocks, or other model can be used for this purpose.

The system 120 can automatically determine which behaviors to predict (and thus which model(s) to use) based on the design of the study, e.g., study parameters such as the study duration, types of data collected, activities involved, etc. This way, the system can identify or filter cohort members based on the activities or behaviors required over the course of the study, either in determining eligibility with respect to the cohort selection criteria or separate from the user-defined or formal selection criteria for the cohort.

The process 1500 can include providing the feature data to one or more models that are based on training data indicating attributes of different subjects and actions of the different subjects (1506). The one or more models can be one or more trained machine learning models. The one or more models can include at least one of a neural network, a support vector machine, a classifier, a regression model, a reinforcement learning model, a clustering model, a decision tree, a random forest model, a genetic algorithm, a Bayesian model, or a Gaussian mixture model. The feature data may be provided as a feature vector, e.g., a sequence of values where each value corresponds to an input slot (e.g., a portion of an input layer of a neural network) designated for a certain type of data.

The models can be trained based on the training data indicating (i) attributes of different subjects and (ii) actions of the different subjects. The trained machine learning models can be trained based on training data indicating actions of the different subjects during research studies in which the different subjects were enrolled. In particular, the actions indicated by the training data can be actions of the type for which the model(s) are trained to predict likelihoods. If the model is configured to predict retention in a cohort, the action data in the training data examples can include records of whether individuals were enrolled in and retained in cohorts of prior research studies. If the model is configured to predict whether an individual will complete a survey, the action data in the training data examples can include record whether individuals who were sent the survey (or another survey) completed the survey.

A wide variety of actions and outcomes can be predicted. For example, a model can be configured to predict whether an individual will provide a specific type of data (e.g., sleep data, diet data, exercise data, etc.), whether an individual will respond to a certain type of communication (e.g., email, SMS text message, mobile device notification, phone call, video conference, etc.), whether an individual will use a technological aid (e.g., a medical device, a cellular phone, a mobile application, etc.) in the manner needed in a study, whether an individual will continue to participate in a study for different durations of a study (e.g., 1 month, 3 months, 1 year, etc.), and so on.

The process 1500 can include obtaining an output from the one or more models that is indicative of whether the subject will perform an action (1508). The output may be expressed in any of various forms. For example, the output may be provided as a likelihood score or confidence score that the subject will perform the action. As another example, the output may be a classification. Models can be configured to predict likelihoods of a single action, or to provide output scores indicating likelihoods for each of multiple actions.

The output from the one or more models can be indicative of a prediction whether the subject will perform a predetermined action in the future, e.g., during a proposed or ongoing research study. As noted above, the model(s) can be based on data indicating whether the different subjects performed the predetermined action. The predetermined action may represent an overall outcome (e.g., an individual being engaged in and retained in a study until the study's completion) or more specific or discrete action (e.g., whether a user will provide a certain type of data or respond to a certain type of communication). For example, the particular predetermined action being predicted could be at least one of: completion of a research study; continuing a particular type of activity for at least a minimum amount of time; use of a medical device; use of a mobile device; use of a software interface; providing a particular type of data; a type or frequency of communication; responding to a request; performance of a physical activity; or compliance with a medication regimen. In some cases the system predicts whether positive outcomes will occur (e.g., completing a study, correct use of a medical device, etc.), in other cases the system predicts the likelihood or risk of negative outcomes (e.g., dropping out of a study, misusing a medical device, etc.).

The process 1500 can include determining a suitability of the subject for inclusion in a cohort based on the output from the one or more trained machine learning models (1510). If the subject is determined to be suitable, the computer system 120 can perform any various actions, such as indicate the determination or model output for a user, include the subject in a set of candidates for a cohort, include the subject in the cohort, initiate enrollment of the subject into the cohort (e.g., sending a communication to a device associated with the subject, initiate data tracking, etc.), and so on. If the subject is determined to not be suitable, the computer system 120 can also perform any of various actions, such as indicate the determination or model output for a user, exclude the subject from a set of candidates for a cohort, exclude the subject from the cohort, and so on.

Determining suitability of the subject can include evaluating the output of the model(s) and considering whether the output indicates that the individual satisfies criteria for the cohort. This criteria may include cohort selection criteria specified by a user or inferred by the computer system 120.

In some implementations, other criteria are used, separate from the selection criteria, to evaluate the output of the model(s). The criteria for evaluating the model output to determine suitability may include other standards or reference data used to ensure quality of a cohort. For example, even if an individual satisfies all of the cohort selection criteria, the individual may nevertheless not be suitable for the cohort due to the individual's low likelihood of completing the study or performing actions required during the study. Thus, despite matching the selection criteria for the cohort, the computer system 120 may exclude the individual from the cohort or warn the user of the low predicted likelihood.

In some implementations, the computer system 120 applies a threshold or other standard to the output of the machine learning model. For example, the computer system 120 can apply a minimum threshold (e.g., 50%, 70%, or some other value) and require individuals to have predicted likelihoods of at least the minimum threshold in order to be included in a cohort. Thus, determining the suitability of the subject for the cohort can include comparing the output from the one or more models to a predetermined threshold.

One example use case is to predict whether a person will successfully use a medical device needed during a study. Consider an example where participation in a study requires use of a moderately expensive medical device. There is a risk that some individuals may fail to use the device, misuse the device, break the device, or even sell the device, all of which would be outcomes that would not allow the needed data for the study to be generated. The database 122 includes records of various individuals and their participation in other studies, as well as personal devices that the individuals use. This provides examples of how different types of individuals have successfully and unsuccessfully used medical devices and other devices. From this information, models are trained to predict, given a set of attributes for a user, how likely the user is to properly use the medical device needed for the study. With this model, the computer system 120 can evaluate each candidate for the cohort individually and potentially limit membership in the cohort to those predicted to have at least a minimum likelihood of using the medical device properly in the study. Of course, the computer system 120 can provide the prediction results for review and action by a researcher, either in addition or as an alternative. This capability of the computer system 120 can avoid significant inefficiencies by avoiding selection and enrollment of people who would not actually participate correctly, and also avoiding the cost of medical devices that would likely be unused or misused.

Typically, models can be trained for each of the various study parameters and study elements that are likely to occur. For example, when a user selects the use of a glucometer or a blood pressure cuff for a study, the system 120 can already have predictive models generated, trained, and ready to predict likelihoods of successful use for individuals. Similarly, models trained to predict engagement and retention can be trained based on large and diverse sets of features, so that features of new studies can simply be indicated as input and no new model training is required each time a new set of study parameters is ready to be evaluated. Nevertheless, the system 120 can be configured to generate and train new models for specific types of predictions or specific studies, as needed.

The process 1500 can include providing output data indicating the prediction for the subject. For example, the computer system 120 can provide output data, for display on a user interface, that includes at least one of: a score based on the output from the one or more models; an indicator of the determined suitability of the subject; or a recommendation to include or exclude the subject from the cohort, wherein the recommendation is based on the determined suitability of the subject.

As noted above, the computer system can select an action, from among a plurality of candidate actions, based on the determined suitability or based on the output from the machine learning model. For example, the selected action can include at least one of: filtering a set of candidates such that the subject is included or excluded based on the determined suitability; providing a recommendation to include or exclude the subject from the cohort; or presenting or declining to present the subject as a candidate for the cohort.

The computer system 120 can access data indicating that a research study associated with the cohort specifies performance of the action by members of the cohort. Determining the suitability of the subject can be based on the data indicating that a research study associated with the cohort specifies performance of the action by members of the cohort.

The cohort selection criteria for the cohort can include a criterion related to performing the action. Determining the suitability of the subject for inclusion in the cohort comprises determining, based on the output from the one or more models, whether the user satisfies the cohort selection criteria.

In some cases, the cohort selection criteria for the cohort do not include a criterion related to performing the action. Nevertheless, to ensure a high-quality cohort and a high likelihood of engagement and retention, the system can determine, separate from considering eligibility according to the cohort selection criteria, whether the user is suitable for the cohort based on the output from the one or more models.

Figure 16:
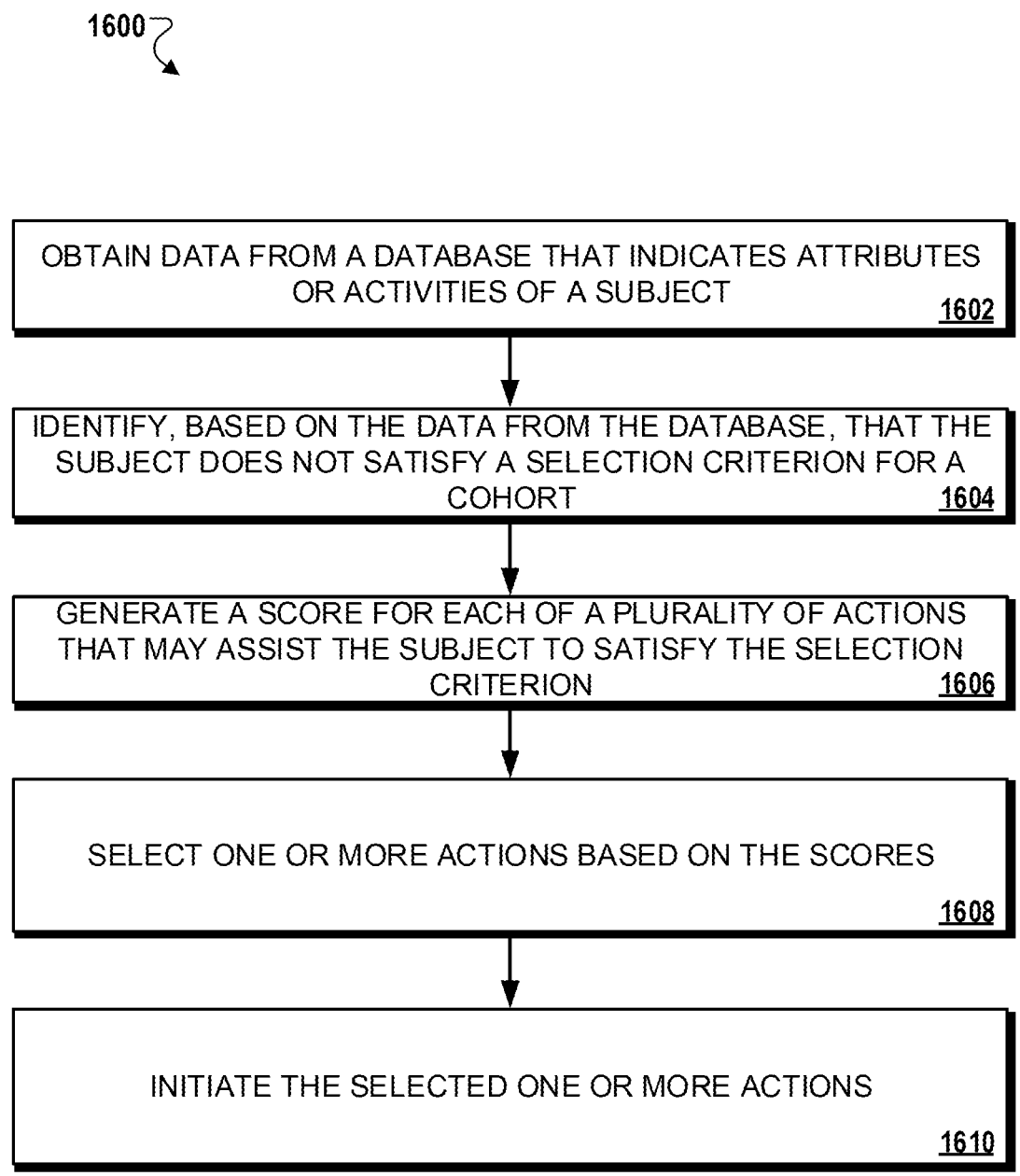
FIG. 16 illustrates an example of a process that can be used to customize interactions to fill gaps in eligibility for a cohort.

FIG. 16 illustrates an example of a process 1600 that can be used to customize interactions to fill gaps in eligibility for a cohort. The process 1600 can be performed by one or more computing devices, such as one or more server computers, one or more client devices, or a combination of server and client devices. As an example, the process 1600 may be performed by the computer system 120.

In the process of defining study parameters and/or selecting individuals for a cohort, there is often a need to expand the set of members in a cohort. Many individuals may not fully satisfy the cohort selection criteria, but could be made to meet the criteria with certain interventions. The process 1600 provides an example of how the computer system 120 can detect gaps (e.g., differences) between a subject's data profile in the database 122 and the cohort selection criteria and generate personalized interventions to bring the individual into eligibility.

In some cases, the computer system 120 can evaluate the size of gaps for individuals with respect to selection criteria and initiate interventions for those with the smallest gaps. For example, for some individuals, only a consent form or blood test may be needed. As another example, some individuals may become eligible simply by agreeing to share mobile phone movement data, phone usage data, or step tracking data. Other individuals may require more burdensome actions or changes and so may be omitted from the group that the system 120 choses for guiding into eligibility.

The computer system 120 can be configured to automatically select and intervene to improve the eligibility of "near-miss" candidates, e.g., individuals identified as having less than some threshold amount of elements still needed to reach eligibility or individuals predicted to have at least a minimum likelihood of reaching eligibility. For example, as a researcher designs a study and enters criteria, the computer system 120 may identify that additional eligible individuals are needed to complete the cohort (e.g., the number of matching individuals is less than a target number), and may select individuals and initiate communications to correct the lacking elements in individual's profiles. In other implementations, the computer system 120 may provide recommendations or options for a user to confirm that eligibility should be enhanced.

The process 1600 can include obtaining data from a database 122 indicating attributes or activities of a subject (1602). This can include obtaining information as discussed above for step 1104 of FIG. 11.

The process 1600 can include identifying, based on the data from the database 122, that the subject does not satisfy a selection criterion for a cohort (1604). For example, this can include comparing data from the database 122 about the individual with the selection criteria and identifying a selection criterion that is not satisfied.

The computer system 120 may evaluate the selection criterion that is not satisfied and predict whether the criterion is one that has at least a minimum likelihood of being changed. This can be based on data in the database 122 about other individuals and whether those individuals were able to acquire the needed attribute to satisfy the selection criterion. In some cases, this can include using a machine learning model to predict whether the current subject being considered is likely to acquire the needed attribute. For example, feature data indicating attributes of the subject can be provided to the trained model, and the model can provide an output likelihood score based on its training using data about individuals similar to the current subject.

The process 1600 can include generating a score for each of a plurality of actions to cause the subject to satisfy the selection criterion (1606). The scores can be based on data in the database 122 indicating actions of other subjects with respect to the selection criterion. For example, the scores can be outputs of one or more machine learning models trained based on the actions of other subjects. Another example is for the computer system 120 to analyze the data in the database 122 to determine a statistical measure or pattern indicating how other individuals have obtained or not obtained the attribute needed to satisfy the selection criterion.

The scores can be generated using one or more models that are based on data in the database 122 indicating the actions of the other subjects with respect to the selection criterion. This data may indicate whether other subjects responded to different communications or interventions to acquire the attribute needed to meet the selection criterion.

The one or more models can be trained machine learning models that have been trained to predict a likelihood of a response of an subject to one or more of the actions in the plurality of actions based on input data indicative of attributes or activities of the subject. The one or more machine learning models may have been trained based on data indicating progressions of one or more subjects from ineligibility for the selection criterion to eligibility for the selection criterion.

For example, the database 122 can include information about instances when the actions in the plurality of actions (e.g., a set of available interventions) have been initiated, and what the responses were from different individuals. The models can be trained based on actions of one or more subjects in response to one or more of the actions in the plurality of actions. This can include training with examples of both (i) those that did acquire the attribute or status needed to reach eligibility and (ii) those that did not acquire the attribute or status needed to reach eligibility.

The one or more models can include at least one of a neural network, a support vector machine, a classifier, a regression model, a reinforcement learning model, a clustering model, a decision tree, a random forest model, a genetic algorithm, a Bayesian model, or a Gaussian mixture model.

The process 1600 can include selecting one or more actions from among the plurality of actions based on the scores (1608). These actions can include different types of communications, such as initiating communications of different types or communications through different communication channels. The plurality of actions include requesting at least one of completion of a survey, an indication of consent, performance of a medical test, acquisition of a medical device, installation a software application, beginning a behavior, ending a behavior, access to mobile device data or sensor data, or records from a third-party data repository.

Naturally, the plurality of actions that the computer system 120 selects among will be different for different selection criteria. For example, the set of actions to remedy a lack of sleep data is different from the set of actions to remedy a lack of blood test information. Nevertheless, even for the same selection criterion, different actions may be selected for different individuals that do not meet that criterion. Consider the case of an individual that does not have a needed blood test result available. A set of actions to remedy this missing element may include asking the individual to take a new blood test, requesting access to the individuals EHR, requesting blood test information from the individual's doctor, asking the individual to enter blood test results, and so on. These requests may also be made in different ways, e.g., by mail, email, text message, through an application, in a doctor's appointment, etc. Different actions may be more likely to be effective for different people, and the predictive modeling and scoring uses the responses of other individuals to predict what actions will be most effective for the current subject.

After scoring the different actions, the computer system 120 can rank the actions according to the scores. The computer system 120 may then select the actions that have the highest rank (e.g., the top-ranked action) and/or select all actions that have at least a minimum likelihood of success (e.g., select actions having scores above a threshold).

The process 1600 can include initiating the selected one or more actions (1608). This can include generating and sending communications over a network to a device, such as a cellular phone, associated with the subject. The computer system 120 may also interact with other systems (e.g., devices for doctors, hospitals, etc.) to request access to needed data.

As discussed above, the computer system 120 can use the database 122 to identify which types of attributes are most easily changed, and so which individuals or sets of individuals are most likely to be brought into eligibility. The computer system 120 can select individuals having sets of non-satisfied selection criteria, recommend them to be guided into eligibility, and then create the personalized outreach to correct the deficiencies of each selected individual. In some implementations, the server system 120 identifies a set of candidates lacking a same item needed for the selection criteria. Although the computer system 120 may initiate requests for each of the individuals to correct the missing element, the computer system 120 may select different actions and different modes of communicating with the different individuals. For example, even to obtain the same information, some might be sent a survey through email, others might be asked to share their EHR data in a text message, and so on, even though the same type of data is ultimately needed for each individual.

The data collected by the computer system 120 and used in any of the examples and implementations discussed above, including the methods of FIGS. 11-16 and as used by the models discussed herein, can include a variety of types of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected and used by the computer system 120 (e.g., to generate feature values, to train models, to evaluate candidates for a cohort, to generate communications to cohort members or cohort candidates, etc.) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteom ics, phylogenomics, phylotranscriptom ics, phytom ics, postgenom ics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., Isopropyl$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

In the claims, the term "or" is generally intended to be inclusive, not exclusive. For example, the phrase "A or B" should be interpreted as encompassing (1) A only, (2) B only, and (3) A and B together. Thus, absent any modifying word or phrase to specify exclusivity (e.g., "either A or B" or "only one of A or B"), listed items are not mutually exclusive.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a cathode ray tube or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method performed by one or more computing devices, the method comprising:
receiving, by the one or more computing devices, data from a client device over a network, wherein the data indicates selection criteria for selecting a cohort of individuals to participate in a research study, the selection criteria comprising a first selection criterion and a second selection criterion, and wherein the first selection criterion and the second selection criterion are each specified by a user through an interface provided by the one or more computing devices;
identifying, by the one or more computing devices and based on the data received from the client device, a first set of candidates for participation in the research study, wherein the first set of candidates are classified as having attributes that satisfy both the first selection criterion and the second selection criterion;
identifying, by the one or more computing devices and based on the data received from the client device, multiple second sets of candidates for participation in the research study, wherein the second sets of candidates respectively satisfy different subsets of the selection criteria for the research study;
for each selection criterion of multiple of the selection criteria for the research study, determining, by the one or more computing devices, a measure of burden on candidates to acquire eligibility with respect to the selection criterion, wherein the measure of burden is based on an amount or difficulty of action by candidates that is needed for candidates to change status with respect to the selection criterion;
for each particular second set of candidates from among the second sets of candidates, determining, by the one or more computing devices, a score for the particular second set of candidates that is based on the determined measure of burden for each of one or more of the selection criteria that the candidates do not currently satisfy;
selecting, by the one or more computing devices, a proper subset of the second sets of candidates to be presented at the client device, wherein the proper subset is selected based at least on the determined scores for the second sets of candidates; and
providing, by the one or more computing devices, output data to the client device over the network, wherein the output data is configured to cause the client device to present a user interface comprising:
an interface element corresponding to the first set of candidates,
interface elements corresponding to the second sets of candidates in the selected proper subset without interface elements corresponding to second sets of candidates that were not selected,
data specifying, for each of the second sets of candidates in the selected proper subset, which of the selection criteria are not satisfied for the second set of candidates, and
one or more interactive controls to (i) add, to the cohort, individuals included in the first set of candidates or one or more of the second sets of candidates in the selected proper subset as selected by the user through user interaction with the one or more interface controls and (ii) cause a notification to be provided to computing devices of individuals added to the cohort.

2. The method of claim 1, comprising:
accessing, by the one or more computing devices, a database storing data indicating attributes of a plurality of individuals, wherein the data stored in the database comprises sensor data acquired from mobile devices respectively associated with the plurality of individuals; and
wherein the first set of candidates and the multiple second sets of candidates are each identified based at least in part on the sensor data stored in the database.

3. The method of claim 1, comprising:
determining, by the one or more computing devices and for each individual included in the first set of candidates and the multiple second sets of candidates, a prediction score indicating a probability of an individual achieving a predetermined outcome in relation to the research study, wherein the prediction score is determined using one or more machine learning models that have been trained based on attributes and activities of other individuals and data indicating whether the other individuals achieved the predetermined outcome.

4. The method of claim 1, wherein:
the interface is a user interface;
the one or more interface elements and the one or more interactive controls are presented in a first portion of the user interface;
attributes of individuals included in the first set of candidates and the selected proper subset of the second sets of candidates are presented in a second portion of the user interface; and
the method further comprises:
receiving, by the one or more computing devices, a user input corresponding to the one or more interactive controls that adds an individual included in the first set of candidates or the selected proper subset of the second sets of candidates to the cohort, and
in response to receiving the user input corresponding to the one or more interactive controls, providing, by the one or more computing devices and for display in the second portion of the user interface, a list of individuals that have been added to the cohort.

5. The method of claim 1, wherein the interface is an application programming interface.

6. The method of claim 1, comprising:
determining, by the one or more computing devices, a target number of individuals to include in the cohort;
determining, by the one or more computing devices, that a number of individuals included in the first set of candidates does not satisfy the target number of individuals; and
wherein the output data for the interface elements corresponding to the selected proper subset of the second sets of candidates is provided based on determining that the number of individuals included in the first set of candidates does not satisfy the target number of individuals.

7. The method of claim 1, further comprising:
obtaining, by the one or more computing devices, log data corresponding to each individual included in first set of candidates, wherein the log data comprises at least one of a health history, a demographic profile, health data collection patterns, or actions of individual when previously participating in a research study;
determining, for each individual included in the first set of candidates and based on the log data, a score representing a predicted likelihood that the individual will complete the research study if added to the cohort; and
providing, through the interface, data indicating the scores determined for individuals included in the first set of candidates.

8. The method of claim 1, wherein:
the output data comprises (i) a number of individuals included in the first set of candidates, and (ii) numbers of individuals included in the respective second sets of candidates in the selected proper subset.

9. The method of claim 1, further comprising:
determining, by the one or more computing devices, that a number of individuals included in the selected proper subset of the second sets of candidates does not satisfy a predetermined threshold number; and
providing, by the one or more computing devices and for output through the interface, a recommendation to change one of the selection criteria based on determining that the number of individuals included in the selected proper subset of the second sets of candidates does not satisfy the predetermined threshold number.

10. The method of claim 1, wherein the notification comprises a link that allows an individual to enroll in the research study.

11. The method of claim 1, further comprising:
providing, by the one or more computing devices, data indicating attributes of candidates in the first set of candidates and the second sets of candidates as input to one or more machine learning models that are trained to compute, for a particular set of attributes of an individual, a score representing a predicted likelihood that future actions of the individual during the research study will comply with participant requirements of the research study, wherein the score is computed based on one or more attributes in the particular set of attributes that are different from attributes assessed by the selection criteria;
obtaining, by the one or more computing devices and from the one or more machine learning models, data indicating a set of scores computed for individuals included in the first set of candidates and the second sets of candidates in the selected proper subset; and
wherein the output data is configured to cause the interface to present data specifying the set of scores computed for individuals included in the first set of candidates and the second sets of candidates in the selected proper subset.

12. The method of claim 1, further comprising:
for each of the second sets of candidates, determining, by the one or more computing devices, a size of the second set of candidates; and
wherein selecting the proper subset of the second sets of candidates is based on the respective sizes of the second sets of candidates.

13. The method of claim 1, wherein determining the measure of burden on candidates to acquire eligibility with respect to the selection criterion is based on an analysis, by the one or more computers, of a type of action by a candidate to change an attribute needed to satisfy the selection criterion.

14. The method of claim 1, wherein determining the measure of burden on candidates to acquire eligibility with respect to the selection criterion is based on records of data collected over time for multiple individuals, the records indicating an amount of the individuals changed an attribute needed to satisfy the selection criterion.

15. The method of claim 1, comprising accessing one or more models that have been trained, based on historical patterns of user activity, to predict likelihoods of actions performed by individuals in response to receiving input indicating attributes of the individuals;
   wherein determining the score for the particular second set of candidates comprises:
      predicting, using the one or more models, one or more likelihoods that the candidates in the particular second set of candidates will perform an action that brings the candidates into compliance with one or more of the selection criteria that the candidates do not currently satisfy.

16. The method of claim 15, wherein the action that brings the candidates included in the second set of candidates into compliance comprises obtaining a biological test associated with a selection criterion included in the selection criteria for the cohort of individuals to participate in the research study.

17. The method of claim 1, comprising:
   identifying, by the one or more computers, a particular selection criterion from among the selection criteria that is not satisfied by the candidates in at least one of the second sets of candidates, wherein the particular selection criterion represents a constraint for an attribute of participants in the research study;
   determining, by the one or more computers, a modified selection criterion that constrains the attribute while modifying the constraint of the particular selection criterion to encompass a larger set of candidates; and
   providing, by the one or more computers and to the client device, a recommendation to use the modified selection criterion in place of the particular selection criterion.

18. The method of claim 17, wherein the particular selection criterion specifies that a first range or set of values for the attribute is needed to satisfy the particular selection criterion;
   wherein the modified selection criterion specifies a second range or set of values for the attribute that is needed to satisfy the modified selection criterion, wherein the second range or set of values is larger than the first range or set of values.

19. The method of claim 17, comprising determining, by the one or more computers, a magnitude with which to modify the particular selection criterion based on assessing an amount of additional candidates that would satisfy the modified selection criterion resulting from the modification.

20. A system comprising:
   one or more computing devices; and
   one or more computer-readable media storing instructions that, when executed by the one or more computing devices, cause the one or more computing devices to perform operations comprising:
      receiving, by the one or more computing devices, data from a client device over a network, wherein the data indicates selection criteria for selecting a cohort of individuals to participate in a research study, the selection criteria comprising a first selection criterion and a second selection criterion, and wherein the first selection criterion and the second selection criterion are each specified by a user through an interface provided by the one or more computing devices;
      identifying, by the one or more computing devices and based on the data received from the client device, a first set of candidates for participation in the research study, wherein the first set of candidates are classified as having attributes that satisfy both the first selection criterion and the second selection criterion;
      identifying, by the one or more computing devices and based on the data received from the client device, multiple second sets of candidates for participation in the research study, wherein the second sets of candidates respectively satisfy different subsets of the selection criteria for the research study;
      for each selection criterion of multiple of the selection criteria for the research study, determining by the one or more computing devices, a measure of burden on candidates to acquire eligibility with respect to the selection criterion, wherein the measure of burden is based on an amount or difficulty of action by candidates that is needed for candidates to change status with respect to the selection criterion;
      for each particular second set of candidates from among the second sets of candidates, determining, by the one or more computing devices, a score for the particular second set of candidates that is based on the determined measure of burden for each of one or more of the selection criteria that the candidates do not currently satisfy;
      selecting, by the one or more computing devices, a proper subset of the second sets of candidates to be presented at the client device, wherein the proper subset is selected based at least on the determined scores for the second sets of candidates; and
      providing, by the one or more computing devices, output data to the client device over the network, wherein the output data is configured to cause the client device to present a user interface comprising:
         an interface element corresponding to the first set of candidates,
         interface elements corresponding to the second sets of candidates in the selected proper subset without interface elements corresponding to second sets of candidates that were not selected,
         data specifying, for each of the second sets of candidates in the selected proper subset, which of the selection criteria are not satisfied for the second set of candidates, and
         one or more interactive controls to (i) add, to the cohort, individuals included in the first set of candidates or one or more of the second sets of candidates in the selected proper subset as selected by the user through user interaction with the one or more interface controls and (ii) cause a notification to be provided to computing devices of individuals added to the cohort.

21. One or more non-transitory computer-readable media storing instructions that, when executed by one or more computing devices, cause the one or more computing devices to perform operations comprising:
   receiving, by the one or more computing devices, data from a client device over a network, wherein the data indicates selection criteria for selecting a cohort of individuals to participate in a research study, the selection criteria comprising a first selection criterion and a second selection criterion, and wherein the first selection criterion and the second selection criterion are each specified by a user through an interface provided by the one or more computing devices;
   identifying, by the one or more computing devices and based on the data received from the client device, a first set of candidates for participation in the research study, wherein the first set of candidates are classified as having attributes that satisfy both the first selection criterion and the second selection criterion;

identifying, by the one or more computing devices and based on the data received from the client device, multiple second sets of candidates for participation in the research study, wherein the second sets of candidates respectively satisfy different subsets of the selection criteria for the research study;

for each selection criterion of multiple of the selection criteria for the research study, determining, by the one or more computing devices, a measure of burden on candidates to acquire eligibility with respect to the selection criterion, wherein the measure of burden is based on an amount or difficulty of action by candidates that is needed for candidates to change status with respect to the selection criterion;

for each particular second set of candidates from among the second sets of candidates, determining, by the one or more computing devices, a score for the particular second set of candidates that is based on the determined measure of burden for each of one or more of the selection criteria that the candidates do not currently satisfy;

selecting, by the one or more computing devices, a proper subset of the second sets of candidates to be presented at the client device, wherein the proper subset is selected based at least on the determined scores for the second sets of candidates; and providing, by the one or more computing devices, output data to the client device over the network, wherein the output data is configured to cause the client device to present a user interface comprising:

an interface element corresponding to the first set of candidates, interface elements corresponding to the second sets of candidates in the selected proper subset without interface elements corresponding to second sets of candidates that were not selected, data specifying, for each of the second sets of candidates in the selected proper subset, which of the selection criteria are not satisfied for the second set of candidates, and one or more interactive controls to (i) add, to the cohort, individuals included in the first set of candidates or one or more of the second sets of candidates in the selected proper subset as selected by the user through user interaction with the one or more interface controls and (ii) cause a notification to be provided to computing devices of individuals added to the cohort.

* * * * *